US012642846B2

(12) United States Patent
Gao et al.

(10) Patent No.: US 12,642,846 B2
(45) Date of Patent: Jun. 2, 2026

(54) ZIKA/DENGUE VACCINE AND APPLICATION THEREOF

(71) Applicant: Institute of Microbiology, Chinese Academy of Sciences, Beijing (CN)

(72) Inventors: Fu Gao, Beijing (CN); Lianpan Dai, Beijing (CN); Jinghua Yan, Beijing (CN); Kun Xu, Beijing (CN); Yuxuan Han, Beijing (CN); Qihui Wang, Beijing (CN); Qingrui Huang, Beijing (CN); Jinhe Li, Beijing (CN)

(73) Assignee: INSTITUTE OF MICROBIOLOGY, CHINESE ACADEMY OF SCIENCES, Beijing (CN)

( * ) Notice: Subject to any disclaimer, the term of this patent is extended or adjusted under 35 U.S.C. 154(b) by 1057 days.

(21) Appl. No.: 17/775,094

(22) PCT Filed: Nov. 9, 2020

(86) PCT No.: PCT/CN2020/127614
§ 371 (c)(1),
(2) Date: May 6, 2022

(87) PCT Pub. No.: WO2021/089055
PCT Pub. Date: May 14, 2021

(65) Prior Publication Data
US 2024/0173395 A1        May 30, 2024

(30) Foreign Application Priority Data
Nov. 7, 2019    (CN) .......................... 201911082867.5

(51) Int. Cl.
| | |
|---|---|
| *A61K 39/12* | (2006.01) |
| *A61P 31/14* | (2006.01) |
| *C07K 14/005* | (2006.01) |
| *C12N 7/00* | (2006.01) |
| *C12N 15/86* | (2006.01) |
| *A61K 39/00* | (2006.01) |

(52) U.S. Cl.
CPC .............. *A61K 39/12* (2013.01); *A61P 31/14* (2018.01); *C07K 14/005* (2013.01); *C12N 7/00* (2013.01); *C12N 15/86* (2013.01); *A61K 2039/5254* (2013.01); *A61K 2039/53* (2013.01); *C12N 2710/10334* (2013.01); *C12N 2710/10343* (2013.01); *C12N 2770/24122* (2013.01); *C12N 2770/24134* (2013.01)

(58) Field of Classification Search
None
See application file for complete search history.

(56) References Cited

U.S. PATENT DOCUMENTS

2018/0340181 A1    11/2018    Chen et al.

FOREIGN PATENT DOCUMENTS

| | | |
|---|---|---|
| CN | 107073135 A | 8/2017 |
| JP | 2019520058 A | 7/2019 |
| JP | 2019523647 A | 8/2019 |
| WO | 2014166500 A2 | 10/2014 |
| WO | 2018011283 A1 | 1/2018 |
| WO | 2018176075 A1 | 10/2018 |
| WO | 2018237313 A1 | 12/2018 |
| WO | 2019043166 A1 | 3/2019 |

OTHER PUBLICATIONS

Pattnaik et al., Vaccines (Basel), May 31, 2020; 8(2):266, 19 pages (Year: 2020).*
Abbink et al., "Durability and correlates of vaccine protection against Zika virus in rhesus monkeys," Sci. Transl. Med. 9, eaao4163 (2017) Dec. 13, 2017, 8 pages.
Anez et al., Genbank KM204118.1, "Complete Genome Sequences of Dengue Virus Type 1 to 4 Strains Used for The Development of CBER/FDA RNA Reference Reagents and WHO International Standard Candidates for Nucleic Acid Testing," Genome Announc, 4(1), e01583-15 (2016), 4 pages.
Anez et al., Genbank KM204119.1, "Complete Genome Sequences of Dengue Virus Type 1 to 4 Strains Used for The Development of CBER/FDA RNA Reference Reagents and WHO International Standard Candidates for Nucleic Acid Testing," Genome Announc, 4(1), e01583-15 (2016), 4 pages.
Barba-Spaeth et al., "Structural basis of potent Zika-dengue virus antibody cross-neutralization," Nature, vol. 536, Aug. 4, 2016, 20 pages.
Beltramello et al., "The Human Immune Response to Dengue Virus is Dominated by Highly Cross-Reactive Antibodies Endowed With Neutralizing and Enhancing Activity," Cell Host & Microbe, 8, 271-283, Sep. 16, 2010, © 2010 Elsevier Inc., 13 pages.
Bennett et al., "Hybrid flagellin as a T cell independent vaccine scaffold," BMC Biotechnology, (2015) 15:71, 12 pages.
Cherrier et al., "Structural basis for the preferential recognition of immature flaviviruses by a fusion-loop antibody," The EMBO Journal (2009) 28, 3269-3276 © 2009 European Molecular Biology Organization, 8 pages.
Crill et al., "Localization and Characterization of Flavivirus Envelope Glycoprotein Cross-Reactive Epitopes," Journal of Virology, Dec. 2004, p. 13975-13986, 12 pages.

(Continued)

*Primary Examiner* — Stacy B Chen
(74) *Attorney, Agent, or Firm* — Umberg Zipser LLP; Priti Phukan

(57)        ABSTRACT

Provided in the present disclosure are a Zika/dengue vaccine and its application thereof. The present disclosure introduces a mutation into the E-protein FL fusion region of the Zika virus or dengue virus. Antigens with said mutations are unable to bind to antibodies that causes ADE. After immunization with the vaccine of the present disclosure acquired from the said antigens, production of FL epitope-induced antibodies can be prevented, thereby reducing or eliminating the ADE effect.

3 Claims, 25 Drawing Sheets

Specification includes a Sequence Listing.

(56) References Cited

OTHER PUBLICATIONS

Dai et al., "Structures of the Zika Virus Envelope Protein and Its Complex With a Flavivirus Broadly Protective Antibody," Cell Host & Microbe 19, 696-704, May 11, 2016 © Elsevier Inc., 10 pages.
Dejnirattisai et al., "A new class of highly potent, broadly neutralizing antibodies isolated from viremic patents infected with dengue virus," Nature Immunology, vol. 16, No. 2, Feb. 2015, 12 pages.
Dejnirattisai et al., "Cross-Reacting Antibodies Enhance Dengue Virus Infection in Humans," Science vol. 328, May 7, 2010, 5 pages.
Deng et al., "A Broadly Flavivirus Cross-Neutralizing Monoclonal Antibody that Recognizes a Novel Epitope within the Fusion Loop of E Protein," PLoS ONE, Jan. 2011, vol. 6, Issue 1, 8 pages.
Dowd et al., "Rapid development of a DNA vaccine for Zika virus," Science, 10.1126/science.aai3197 (2016), 10 pages.
Fowler et al., "Maternally Acquired Zika Antibodies Enhance Dengue Disease Severity in Mice," Cell Host & Microbe 24, 743-750, Nov. 14, 2018, © 2018 Elsevier Inc., 14 pages.
George et al., "Prior Exposure to Zika Virus Significantly Enhances Peak Dengue-2 Viremia in Rhesus Macaques," Scientific Reports, 7:10498, Sep. 5, 2017, 10 pages.
Haddow et al., Genbank JN860885.1, "Genetic characterization of zika virus strains: geographic expansion of the Asian lineage," PLoS Negl Trop Dis, 6(2), E1477, (2012) 4 pages.
Hassan, et al., "A Gorilla Adenovirus-Based Vaccine against Zika Virus Induces Durable Immunity and Confers Protection in Pregnancy," Cell Reports 28, 2634-2646, Sep. 3, 2019, 21 pages.
Katzelnick et al., "Antibody-dependent enhancement of severe dengue disease in humans," Science 358, 929-932, Nov. 17, 2017, 5 pages.
Lazear et al., "A Mouse Model of Zika Virus Pathogenesis," Cell Host & Microbe 19, 1-11, May 11, 2016, © 2016 Elsevier Inc., 12 pages.
Li et al., "Both structure and function of human monoclonal antibodies contribute to enhancement of Zika Virus Infectivity in vitro," Science China Life Sciences, Dec. 2017, vol. 60, No. 12:1396-1398, 3 pages.
Oliphant et al., "Antibody Recognition and Neutralization Determinants on Domains I and II of West Nile Virus Envelope Protein," Journal of Virology, vol. 80, No. 24, Dec. 2006, p. 12149-12159.
Rey et al., "The bright and the dark side of human antibody responses to flaviviruses: lessons for vaccine design," EMBO Reports, Dec. 27, 2017, 19 pages.
Richner et al., "Modified mRNA Vaccines Protect against Zika Virus Infection," Cell 168, Mar. 9, 2017, © 2017 Elsevier Inc., 1114-1125.
Slon-Campos et al., "A protective Zika virus E-dimer-based subunit vaccine engineered to abrogate antibody-dependent enhancement of dengue infection," Nature Immunology, vol. 20, Oct. 2019, 1291-1298.
Stettler et al., "Specificity, cross-reactivity, and function of antibodies elicited by Zika virus infection," Science, Aug. 19, 2016, vol. 353, Issue 6301, 5 pages.
Valiant et al., "Zika convalescent macaques display delayed induction of anmanestic cross-neutralizing antibody responses after dengue infection," Emerging Microbes & Infections (2018)7:130, 11 pages.

Wang et al., "Molecular determinants of human neutralizing antibodies isolated from a patient infected with Zika virus," Sci. Transl. Med. 8, 369ra179, Dec. 14, 2016, 10 pages.
Wang et al., "Monoclonal Antibodies against Zika Virus: Therapeutics and Their Implications for Vaccine Design," Journal of Virology, Oct. 2017, vol. 91, Issue 20, 6 pages.
Wang, et al., Genbank AF289029.1, "Determination and analysis of the complete genomic sequence of the dengue type 4 virus B5 strain isolated in China," J. Biochem. Mol. Biol. 17(2) 148-154, 2001, 4 pages.
Xu et al., "Recombinant Chimpanzee Adenovirus Vaccine AdC7-M/E Protects against Zika Virus Infection and Testis Damage," Journal of Virology, Mar. 2018, vol. 92, Issue 6, 16 pages.
Zhao et al., Genbank KF824903.1, "Direct Submission," Department of Virology, Beijing Institute of Microbiology and Epidemiology, 20 Dongda Street, Fengtai District, Beijing 10071, China, 4 pages. (2014).
Zhao et al., "Structural Basis of Zika Virus-Specific Antibody Protection," Cell 166, 1-12, Aug. 11, 2016, © 2016 Elsevier Inc., 13 pages.
Bittar et al., "Genome sequencing and genetic characterization of Culex Flavirirus (CxFV) provides new information about its genotypes," Virology Journal, 2016; 13:158; 8 pgs.
Extended European Search Report for Application No. 20884983.6 dated Jan. 9, 2024; 14 pgs.
Kuwata et al., "Isolation of Japanese encephalitis virus and a novel insect-specific flavivirus from mosquitoes collected in a cowshed in Japan," Arch Virol, 2015; 160:2151-2159.
First Office Action of Corresponding JP Application No. 2022-526316 issued Aug. 13, 2024.
Frontiers in Immunology, Sculpting humoral immunity through dengue vaccination to enhance protective immunity (2012) vol. 3, Article 334.
Crabtree et al., "polyprotein precursor [Kamiti River virus]—Protein—NCBI," Database GenBank [Online] National Institutes of Health, Database accession No. AY149904, Sep. 12, 2002; 3 pgs.
Crill et al., "Sculpting humoral immunity through dengue vaccination to enhance protective immunity," Frontiers in Immunology, Nov. 2012; 3:1-19.
Hoshino et al., "polyprotein, partial [Aedes flavivirus]—Protein—NCBI," Database GenBank [Online] National Institutes of Health, Database accession No. AB488421; Feb. 25, 2009; 1 page.
Hughes et al., "Manipulation of immunodominant dengue virus E protein epitopes reduces potential antibody-dependent enhancement," Virology Journal, Jun. 18, 2012; 9(1); 12 pgs.
Supplementary European Search Report for European Application No. 20884983 dated Nov. 8, 2023; 12 pgs.
Blitvich, B.J. et al., "GenBank, Accession No. NC_030400," GenBank Database, Aug. 13, 2018 (Aug. 13, 2018), 5 pages.
Bolling, B.G. et al., GenBank, Accession No. NC_001564, GenBank Database, Aug. 13, 2018 (Aug. 13, 2018), 5 pages.
Haddow, A.D. et al., "GenBank, Accession No. KC181923," GenBank Database, Apr. 24, 2013 (Apr. 24, 2013), 4 pages.
PCT International Search Report and Written Opinion, International Application No. PCT/CN2020/127614, International Filing Date Nov. 9, 2020, 9 pages.

* cited by examiner

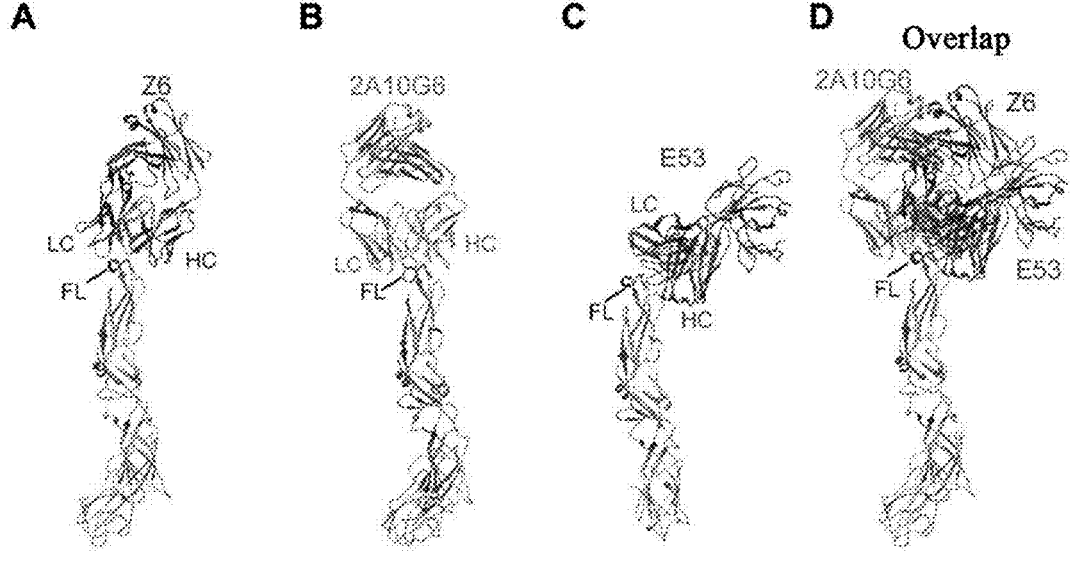

A     B     C     D     Overlap

FIG. 5

ZIKV sE contacts Z6

| ZIKV sE amino acid residue | Heavy chain of antibody contacts | Light chain of antibody contacts | Antibody Total Contacts |
|---|---|---|---|
| P75 | | 8 | 8 |
| T76 | | 15 | 15 |
| W101 | 59 | 25 | 84 |
| G102 | 1 | | 1 |
| G104 | | 4 | 4 |
| C105 | | 10 | 10 |
| G106 | | 34 | 34 |
| L107 | 1 | 12 | 13 |
| F108 | 41 | 6 | 47 |
| G109 | | 5 | 5 |
| K110 | | 7 | 7 |
| Total | 102 | 124 | 226 |

ZIKV sE contacts 2A10G6

| ZIKV sE amino acid residue | Heavy chain of antibody contacts | Light chain of antibody contacts | Antibody Total Contacts |
|---|---|---|---|
| T76 | 10 | | 10 |
| G77 | 6 | | 6 |
| W101 | 59 | 24 | 83 |
| G102 | | 6 | 6 |
| G104 | 3 | | 3 |
| C105 | 10 | | 10 |
| G106 | 17 | | 17 |
| L107 | 15 | | 15 |
| G108 | 14 | 33 | 47 |
| | 134 | 63 | 197 |

WNV sE contacts E53

| ZIKV sE amino acid residue | Heavy chain of antibody contacts | Light chain of antibody contacts | Antibody Total Contacts |
|---|---|---|---|
| C74 | 5 | | 5 |
| F75 | 8 | | 8 |
| T76 | 36 | | 36 |
| M77 | 32 | | 32 |
| G78 | 8 | | 8 |
| E79 | 18 | | 18 |
| G104 | 10 | | 10 |
| C105 | 6 | | 6 |
| G106 | 10 | 6 | 16 |
| L107 | 5 | 4 | 9 |
| G109 | 4 | | 4 |
| K110 | 15 | | 15 |
| Total | 155 | 9 | 164 |

The number represents the number of atom-to-atom contacts, analyzed by CCP4 software package (the threshold of distance is 4.5 Å)

FIG. 6

BALB/c mice

*Ifnar1$^{-/-}$* mice

| WT | HV1-18 | HV1-22 | HV1-26 | HV1-39 | HV1-4 | HV1-52 | HV1S 34*01 | IGHV 1S81 | HV2-6 | HV3-2 | HV3-6 | HV7-3 | HV8-8 | HV9-2-1 | HV9-3 |
|---|---|---|---|---|---|---|---|---|---|---|---|---|---|---|---|
| KV2-137 | 0 | 0 | 0 | 0 | 0 | 0 | 0 | 0.30 | 0 | 0 | 0 | 0 | 0 | 0 | 0 |
| KV3-12 | 0 | 0 | 0 | 0 | 0 | 0 | 0 | 0 | 0 | 0 | 0 | 2.99 | 0 | 0 | 0 |
| KV3-2 | 0.30 | 0 | 0 | 0 | 0 | 0 | 0 | 0 | 0 | 0 | 0 | 0 | 0 | 0 | 0 |
| KV3-4 | 0 | 0.90 | 0 | 0 | 0 | 0 | 0 | 0 | 0 | 0 | 0 | 0 | 0 | 2.99 | 0 |
| KV4-74 | 0 | 0.30 | 0 | 0 | 0 | 0 | 0 | 0 | 0 | 0 | 0 | 0 | 0 | 0 | 0 |
| KV5-43 | 0 | 0 | 0 | 0 | 0 | 0 | 0 | 0 | 0 | 2.40 | 0 | 0 | 0 | 0.30 | 0 |
| KV6-15 | 0 | 0 | 0 | 0.30 | 0 | 0.90 | 0 | 0 | 0 | 0 | 0 | 0 | 0 | 0 | 0 |
| KV6-23 | 0 | 7.49 | 0.60 | 0 | 0 | 0 | 0 | 0 | 0 | 0 | 0 | 0 | 0 | 0.90 | 0 |
| KV6-32 | 0 | 0 | 0 | 0 | 0.30 | 0 | 0 | 0 | 0 | 0 | 0 | 0 | 0 | 0 | 0 |
| KV8-30 | 0 | 0 | 0 | 0 | 0 | 0.30 | 0 | 0.30 | 0 | 0 | 0 | 0 | 0 | 0 | 0 |
| KV9-120 | 0 | 0 | 0 | 0 | 0 | 0 | 0 | 0 | 0 | 0 | 0 | 0 | 0 | 0 | 0.60 |
| KV9-124 | 0 | 0 | 0 | 0 | 0 | 0 | 0 | 0 | 0 | 0 | 0 | 0 | 1.20 | 0 | 0 |
| KV10-96 | 0.30 | 0 | 0 | 0 | 0.90 | 0 | 1.80 | 0 | 0 | 3.89 | 0.30 | 0.60 | 0 | 29.94 | 0.30 |
| KV11-125 | 0 | 0.30 | 0.30 | 0 | 0 | 0 | 0 | 0 | 0 | 0 | 0 | 0 | 0 | 0.30 | 0 |
| KV1-135 | 0 | 0 | 0 | 0 | 0 | 0 | 0 | 0 | 0 | 0 | 0 | 0 | 0 | 0 | 0.30 |
| KV12-44 | 0 | 0 | 0 | 0 | 0 | 0 | 0 | 0 | 0 | 0 | 0 | 0 | 0 | 0.30 | 0 |
| KV14-100 | 0 | 0.30 | 0 | 0 | 0 | 0 | 0 | 0 | 0 | 0 | 0 | 0 | 0 | 0 | 0 |
| KV14-111 | 0 | 14.37 | 2.40 | 0.30 | 0 | 0 | 0 | 0 | 0.30 | 0.60 | 0 | 0 | 0 | 1.20 | 0 |
| KV19-93 | 0 | 0 | 0 | 0 | 0 | 0 | 0 | 0 | 0.30 | 0 | 0 | 0 | 0 | 0 | 0.30 |
| LV1 | 0 | 0 | 0.30 | 0 | 0 | 0 | 0 | 0 | 0 | 0.30 | 0 | 0 | 0 | 0 | 0 |

FIG. 22

| MotB | IGHV 1-4 | IGHV 1-5 | IGHV 1-69 | IGHV 1-84 | IGHV 1-18 | IGHV 1-22 | IGHV 1-26 | IGHV 1S34·?21 | IGHV/ 1S12·1?01 | IGHV 1S13·0?01 | IGHV 2-3 | IGHV 2-8 | IGHV 3-2 | IGHV 3-6 | IGHV 4-1 | IGHV 5-8 | IGHV 5-9-3 | IGHV 5-12-1 | IGHV 6-6 | IGHV 7-3 | IGHV 6-8 | IGHV 9-2-1 | IGHV 9-3 |
|---|---|---|---|---|---|---|---|---|---|---|---|---|---|---|---|---|---|---|---|---|---|---|---|
| IGKV 1-110 | 0 | 0 | 0 | 0 | 0 | 0 | 0 | 0 | 0 | 0 | 0 | 0 | 0 | 0 | 0.85 | 0 | 0 | 0 | 0 | 0 | 0 | 0 | 0 |
| IGKV 1-117 | 0.43 | 0.43 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV 1-135 | 0 | 0 | 0 | 0 | 0 | 0 | 0 | 0 | 0 | 0 | 0 | 0 | 0 | 0 | 0 | 0 | 0 | 0 | 0 | 1.28 | 0 | 0 | 0 |
| IGKV 2-109 | 0 | 0 | 1.71 | 0 | 0 | 0 | 0 | 0 | 0 | 0 | 0 | 0 | 5.56 | 0 | 0 | 0.43 | 0 | 0 | 0 | 0 | 0.43 | 0 | 0 |
| IGKV 3-2 | 0 | 0 | 0 | 0 | 0 | 0 | 0 | 0 | 0 | 0 | 0 | 0 | 0 | 0 | 0 | 0 | 0 | 0 | 0 | 0 | 0 | 1.71 | 0 |
| IGKV 3-4 | 0 | 0 | 0 | 0 | 0 | 0 | 0 | 0 | 0 | 0 | 0 | 0 | 0 | 0 | 0 | 0 | 0 | 0 | 0 | 0 | 0 | 0.43 | 0 |
| IGKV 3-5 | 0 | 0 | 0 | 0 | 0 | 0 | 3.42 | 0 | 0 | 0 | 0.43 | 0 | 0 | 0 | 0 | 0 | 0 | 0 | 0 | 0 | 0 | 0 | 0 |
| IGKV 3-10 | 0 | 0 | 0 | 0 | 0 | 0 | 0 | 0 | 0 | 0 | 0.43 | 0 | 0 | 0 | 0 | 0 | 0 | 0 | 0 | 0 | 0 | 2.14 | 0.85 |
| IGKV 3-12 | 0 | 0 | 0 | 0 | 0 | 0 | 0 | 0 | 0 | 0 | 0 | 0 | 0 | 0 | 0 | 0 | 2.56 | 0 | 0 | 0 | 0 | 2.14 | 0.43 |
| IGKV 4-50 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2.56 |
| IGKV 4-55 | 0 | 0 | 0 | 0 | 0 | 0 | 0 | 0 | 0 | 0 | 0 | 0 | 0 | 0 | 0.43 | 0 | 0 | 4.27 | 0 | 2.14 | 0 | 0 | 0 |
| IGKV 4-57 | 0 | 0 | 0 | 5.13 | 0 | 0 | 0 | 0.43 | 0 | 0 | 0 | 0 | 0 | 0 | 0 | 0 | 0 | 0 | 0 | 0 | 0 | 0 | 0 |
| IGKV 4-61 | 0 | 0 | 0 | 0 | 0 | 0 | 0 | 0 | 0 | 0 | 0 | 0 | 0 | 0 | 0 | 0 | 0 | 0 | 0 | 1.28 | 0 | 0 | 0 |
| IGKV 4-72 | 0 | 0 | 0.43 | 0 | 0 | 0 | 0 | 0 | 0 | 0 | 0 | 0 | 0 | 0 | 0 | 0 | 0 | 0 | 0 | 0 | 0 | 0 | 0 |
| IGKV 5-43 | 0 | 0 | 0 | 0 | 0 | 0 | 0.43 | 0 | 0 | 0 | 0.43 | 0 | 0 | 0 | 0 | 0 | 0 | 0.43 | 0 | 0 | 0 | 0 | 0 |
| IGKV 5-48 | 0 | 0 | 0 | 0 | 0 | 0 | 0 | 0 | 0 | 0 | 0 | 0 | 0 | 8.41 | 0 | 0 | 0 | 0 | 0 | 0 | 0 | 0 | 0 |
| IGKV 6-15 | 0 | 0 | 0 | 0 | 0 | 0 | 0.43 | 0 | 0.43 | 0 | 0 | 0 | 0 | 0 | 0.43 | 0.43 | 0 | 0 | 0 | 0 | 0 | 0 | 0 |
| IGKV 6-17 | 0 | 0 | 0 | 0 | 0 | 0 | 0 | 0 | 0 | 0 | 0 | 0 | 0 | 0 | 0.43 | 0 | 0 | 0 | 0 | 0 | 0 | 0 | 0 |
| IGKV 6-20 | 0 | 0 | 0 | 0 | 0 | 0 | 0 | 0 | 0 | 0 | 0 | 0 | 0 | 0 | 0 | 0 | 0 | 0 | 0 | 0 | 0 | 1.28 | 0 |
| IGKV 6-25 | 0 | 0 | 0 | 0 | 0 | 0 | 0 | 0 | 0 | 0 | 0 | 0 | 0 | 0 | 0.85 | 0 | 0 | 0 | 0 | 0 | 0 | 0 | 0 |
| IGKV 6-32 | 0.85 | 0 | 0 | 0 | 0 | 0 | 0 | 0 | 0 | 0 | 0 | 0 | 0.85 | 0 | 0 | 0 | 0 | 0 | 0 | 0 | 0 | 0 | 0 |
| IGKV 8-24 | 0 | 0 | 0 | 0 | 0 | 0 | 0 | 0 | 0 | 19.2 | 0 | 0 | 0 | 0 | 0 | 0 | 0 | 0 | 0 | 0 | 0 | 0 | 0 |
| IGKV 8-27 | 0 | 0 | 0 | 0 | 0 | 0 | 0 | 0 | 0 | 0 | 0 | 0 | 0 | 0 | 0 | 0 | 0 | 0 | 0 | 0 | 0 | 0.85 | 0 |
| IGKV 8-30 | 0 | 0 | 0 | 0 | 0 | 0.43 | 0 | 2.56 | 0 | 0 | 0 | 0 | 0 | 0 | 0 | 0 | 0 | 0 | 0.43 | 0 | 0 | 0 | 0 |
| IGKV 10-94 | 0 | 0 | 0 | 0 | 0 | 0 | 0 | 0 | 0 | 0 | 0 | 0 | 0 | 0 | 0 | 0 | 0 | 0 | 0 | 0.43 | 0 | 0 | 0 |
| IGKV 10-96 | 0 | 0 | 0 | 0 | 0 | 0 | 0 | 0 | 0 | 0 | 0 | 0 | 0 | 0 | 0 | 0 | 0 | 0 | 0 | 0.43 | 0 | 0 | 0 |
| IGKV 11-125 | 0 | 0 | 0 | 0 | 0 | 0.43 | 0 | 0 | 0 | 0 | 0 | 0 | 0 | 0 | 0 | 0 | 0 | 0 | 0 | 0 | 0 | 0 | 0 |
| IGKV 12-41 | 0 | 0 | 0 | 0 | 1.71 | 0 | 0 | 3.85 | 0 | 0 | 0 | 0 | 0 | 0 | 0 | 0 | 0 | 0 | 0 | 0 | 0 | 0 | 0 |
| IGKV 14-111 | 0 | 0 | 0 | 0.43 | 0 | 0 | 0 | 0 | 0 | 0 | 0 | 0 | 0 | 0 | 0 | 0 | 0 | 0 | 0.43 | 0 | 0 | 0 | 0 |
| IGKV 14-130 | 0 | 0 | 0 | 0 | 0 | 0 | 0.43 | 1.71 | 0 | 0 | 0 | 0.85 | 0 | 0 | 0 | 0 | 0 | 0 | 0 | 0 | 0 | 0 | 0 |
| IGKV 15-103 | 0 | 0 | 0 | 0 | 0 | 0.43 | 0 | 0.85 | 0 | 0 | 0 | 0 | 0 | 0 | 0 | 0 | 0 | 0 | 0 | 0 | 0 | 0 | 0 |
| IGKV 17-127 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0.85 |

FIG. 23

| MutC | IGHV 1-4 | IGHV 1-9 | IGHV 1-15 | IGHV 1-18 | IGHV 1-22 | IGHV 1-26 | IGHV 1-31 | IGHV 1-39 | IGHV 1-52 | IGHV 1-55 | IGHV 1-63 | IGHV 1-69 | IGHV 1-77 | IGHV 1-84 | IGHV 1-87 | IGHV 1S29 | IGHV 1S34 | IGHV 1S81 | IGHV 1S127 | IGHV 1S139 | IGHV 2-2 | IGHV 2-5 |
|---|---|---|---|---|---|---|---|---|---|---|---|---|---|---|---|---|---|---|---|---|---|---|
| IGKV1-88 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV1-110 | 0 | 0.19 | 0 | 0 | 0 | 0 | 0 | 0 | 0 | 0 | 0 | 0.58 | 0 | 0 | 0 | 0 | 0 | 0 | 0 | 0 | 0 | 0.78 |
| IGKV1-117 | 0.39 | 0 | 0 | 0 | 0 | 0 | 0 | 0 | 0 | 0 | 0 | 0 | 0 | 0 | 0 | 0 | 0 | 0 | 0.19 | 0 | 0 | 0 |
| IGKV1-135 | 0 | 0 | 0 | 0 | 0.39 | 0.78 | 0 | 0 | 0 | 0 | 0.39 | 0 | 0 | 0 | 0 | 0 | 0.19 | 0 | 0 | 0 | 0 | 0 |
| IGKV2-137 | 0 | 0 | 0 | 0 | 0 | 0 | 0 | 0 | 0 | 0 | 0 | 0 | 0 | 0 | 0 | 0 | 0.19 | 0.18 | 0 | 0 | 0 | 0 |
| IGKV3-1 | 0 | 0 | 0 | 0 | 0 | 0 | 0 | 0 | 0.19 | 0 | 0 | 0 | 0 | 0 | 0 | 0 | 0 | 0.19 | 0 | 0 | 0 | 0 |
| IGKV3-5 | 0 | 0 | 0 | 0 | 0 | 0 | 0 | 0 | 0 | 0 | 0 | 0 | 0 | 0 | 0 | 0 | 0 | 0 | 0 | 0 | 0.19 | 0 |
| IGKV3-7 | 0 | 0 | 0 | 0 | 0 | 0 | 0 | 0 | 0 | 0 | 0 | 0 | 0 | 0 | 0 | 0 | 0 | 0 | 0 | 0 | 0.19 | 0 |
| IGKV3-10 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV3-12 | 0 | 0 | 0 | 0 | 0 | 0 | 0.18 | 0 | 0 | 0 | 0 | 0 | 0 | 0 | 0 | 0.18 | 0 | 0 | 0 | 0.78 | 0 | 0 |
| IGKV4-55 | 0 | 0 | 0 | 0 | 0 | 0 | 0 | 0.18 | 0 | 0 | 0 | 0 | 0 | 0 | 0 | 0 | 0 | 0 | 0 | 0 | 0 | 0.39 |
| IGKV4-57 | 0 | 0 | 0 | 0 | 0 | 0 | 0 | 0 | 0 | 0 | 0 | 0 | 0.78 | 0 | 0.19 | 0 | 1.17 | 0 | 0 | 0 | 0 | 0 |
| IGKV4-59 | 0 | 0 | 0 | 0 | 0 | 0 | 0.39 | 0 | 0 | 0 | 0 | 0 | 0 | 0 | 0 | 0 | 0 | 0 | 0 | 0 | 0 | 0 |
| IGKV4-61 | 0 | 0 | 0 | 0 | 0 | 0 | 0.39 | 0 | 0 | 0 | 0 | 0 | 0 | 0 | 0 | 0 | 0 | 0 | 0 | 0 | 0 | 0 |
| IGKV4-63 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV4-68 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV4-70 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV4-72 | 0 | 0 | 0 | 0 | 0 | 0 | 0 | 0.19 | 0 | 0 | 0 | 0 | 0 | 0 | 0 | 0.58 | 0.97 | 0 | 0 | 0 | 0 | 0 |
| IGKV4-74 | 0 | 0 | 0 | 0 | 0 | 0 | 0 | 0 | 0 | 0 | 0 | 0 | 0 | 0 | 0 | 0 | 0 | 0 | 0.19 | 0 | 0 | 0 |
| IGKV4-80 | 0 | 0 | 0 | 0 | 0 | 0 | 0.18 | 0 | 0 | 0 | 0 | 0 | 0 | 0 | 0 | 0 | 0 | 0 | 0 | 0 | 0 | 0 |
| IGKV5-45 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV5-48 | 0 | 0 | 0 | 0 | 0 | 0 | 0 | 0 | 0 | 0 | 0 | 0 | 0 | 0 | 0 | 0 | 0 | 0.19 | 0 | 0 | 0 | 0 |
| IGKV6-15 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV6-17 | 0 | 0 | 0 | 0 | 0.19 | 0 | 0 | 0 | 0 | 0 | 0 | 0 | 0 | 0 | 0 | 0 | 0 | 0.19 | 0 | 0.18 | 0 | 0 |
| IGKV6-20 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV6-23 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV6-32 | 2.33 | 0 | 0 | 0 | 0 | 0.19 | 0 | 0 | 0 | 0 | 0 | 0 | 0 | 0 | 0 | 0 | 0.39 | 0 | 0.19 | 0 | 0 | 0 |
| IGKV8-16 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV8-21 | 0 | 0.19 | 0 | 0 | 0 | 0 | 0 | 0 | 0.58 | 0 | 0 | 0 | 0 | 0 | 0 | 0 | 0 | 0 | 0 | 0 | 0 | 0 |
| IGKV8-24 | 0.58 | 0 | 0 | 3.88 | 0.19 | 0.19 | 0 | 0 | 0 | 0.19 | 0 | 0 | 0 | 0 | 0 | 0.39 | 0.39 | 0 | 0 | 0 | 0 | 0 |
| IGKV8-30 | 0.19 | 0 | 0 | 0 | 0.16 | 0.19 | 0 | 0 | 2.52 | 0 | 0 | 0.97 | 0 | 0 | 1.47 | 0 | 0 | 0 | 0.19 | 0 | 0 | 0 |
| IGKV9-120 | 0 | 0 | 0 | 0 | 0 | 0 | 0 | 0.19 | 0 | 0 | 0 | 0 | 0 | 0 | 0 | 0 | 0 | 0 | 0 | 0 | 0 | 0 |
| IGKV9-124 | 0 | 0 | 0 | 0 | 0 | 0 | 0 | 0 | 0 | 0 | 0 | 0 | 0 | 0 | 0 | 0.19 | 0 | 0 | 0 | 0 | 0 | 0 |
| IGKV10-94 | 0 | 0 | 0.19 | 0 | 0.39 | 0 | 0 | 0 | 0 | 0 | 0 | 0 | 0 | 0 | 0 | 0 | 0 | 0 | 0 | 0 | 0 | 0.19 |
| IGKV10-96 | 0 | 0.58 | 0 | 0 | 0 | 0 | 0 | 0.19 | 0 | 0 | 0 | 0 | 0 | 0 | 0.19 | 0 | 0 | 0 | 0 | 0.19 | 0 | 0 |
| IGKV11-125 | 0 | 0 | 0.78 | 0 | 1.36 | 0.19 | 0 | 0 | 0 | 0 | 0 | 0 | 0 | 0 | 0 | 0 | 0 | 0 | 0 | 0 | 0 | 0 |
| IGKV12-41 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV12-44 | 0 | 0 | 0 | 0 | 0 | 0 | 0 | 0 | 0 | 0 | 0 | 0 | 0 | 0 | 0 | 0 | 0.19 | 0 | 0 | 0 | 0 | 0 |
| IGKV12-89 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV13-84 | 0 | 0 | 0 | 0 | 0 | 0 | 0 | 0 | 0.97 | 0 | 0 | 0 | 0 | 0 | 0 | 0 | 0 | 0 | 0 | 0 | 0 | 0 |
| IGKV14-111 | 0 | 0 | 0 | 0 | 0.58 | 0 | 0 | 0 | 0 | 0 | 0 | 0 | 0 | 0 | 0 | 0 | 0 | 0 | 0 | 0 | 0 | 0 |
| IGKV15-103 | 0.19 | 0 | 0 | 1.94 | 0 | 0.78 | 0 | 0 | 0 | 0 | 0 | 0 | 0 | 0 | 0 | 0.97 | 0 | 0 | 0 | 0 | 0 | 0 |
| IGKV17-127 | 0 | 0 | 0 | 0 | 0 | 0 | 0 | 0 | 0 | 0 | 0.19 | 0 | 0 | 0 | 0 | 0 | 0 | 0.39 | 0 | 0 | 0 | 0 |
| IGKV19-93 | 0 | 0 | 0 | 0 | 0 | 0 | 0 | 0 | 0 | 0 | 0.19 | 0 | 0 | 0 | 0 | 0 | 0 | 0 | 0 | 0 | 0 | 0 |
| IGLV1 | 0 | 0 | 0 | 0 | 0 | 0.39 | 0 | 0 | 0 | 0 | 0.19 | 0 | 0 | 0 | 0 | 0 | 0 | 0 | 0 | 0 | 0 | 0 |

FIG. 24-1

| MutC | IGHV 2-5 | IGHV 3-6-8 | IGHV 2-9 | IGHV 2-9-2 | IGHV 3-2 | IGHV 3-5 | IGHV 3-6 | IGHV 4-1 | IGHV 5-17 | IGHV 5-6 | IGHV 5-9-3 | IGHV 5-9-4 | IGHV 6-6 | IGHV 8-8 | IGHV 9-2-1 | IGHV 9-3 | IGHV 9-4 | IGHV 10S3 | IGHV 14-1 | IGHV 14-3 | IGHV 14-4 |
|---|---|---|---|---|---|---|---|---|---|---|---|---|---|---|---|---|---|---|---|---|---|
| IGKV1-88 | 0 | 0 | 0 | 0 | 0 | 0 | 0 | 0 | 1.55 | 0 | 0 | 0 | 0 | 0 | 0 | 0.78 | 0 | 0 | 0 | 0 | 0 |
| IGKV1-110 | 0 | 0 | 0 | 0 | 0 | 0 | 0 | 0.78 | 3.3 | 0.39 | 0 | 0.19 | 0 | 0.58 | 0 | 0.78 | 0 | 0 | 0 | 0 | 0 |
| IGKV1-117 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV1-135 | 0 | 0 | 0.19 | 0 | 0 | 0 | 0 | 0 | 0 | 0 | 0 | 0 | 0 | 0 | 0 | 0 | 0 | 0 | 0 | 0 | 0 |
| IGKV2-137 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV3-1 | 0.19 | 0 | 0 | 0 | 0 | 0 | 0 | 0 | 0 | 0 | 0 | 0.19 | 0 | 0 | 0.39 | 0 | 0 | 0 | 0 | 0 | 0 |
| IGKV3-5 | 0.19 | 0 | 0 | 0 | 0 | 0 | 0 | 0 | 0 | 0 | 0 | 0 | 0 | 0 | 0 | 0 | 0 | 0 | 0 | 0.39 | 0 |
| IGKV3-7 | 0.39 | 0 | 0 | 0 | 0.78 | 0 | 0 | 0.19 | 0 | 0 | 0 | 0 | 0 | 0 | 0 | 0 | 0 | 0 | 0 | 0 | 0 |
| IGKV3-10 | 0 | 0 | 0 | 0 | 0 | 0 | 0 | 0 | 0 | 0 | 0 | 0 | 0 | 0 | 0.39 | 0 | 0.97 | 0 | 0 | 0 | 0 |
| IGKV3-12 | 0 | 0 | 0 | 0 | 0 | 0 | 0 | 0 | 0 | 0 | 0 | 0.19 | 0 | 0 | 1.17 | 4.27 | 0 | 0 | 0 | 0 | 0.19 |
| IGKV4-55 | 0 | 0 | 0.19 | 0 | 0 | 0 | 0 | 0 | 0 | 0.39 | 0 | 0 | 0.78 | 0 | 0 | 0 | 0 | 0 | 0 | 0 | 0 |
| IGKV4-57 | 0 | 0 | 0 | 0 | 0 | 0 | 0 | 0 | 0 | 0 | 0 | 0 | 0.78 | 0 | 0 | 0 | 0 | 0 | 0 | 0 | 0 |
| IGKV4-59 | 0 | 0 | 0 | 0 | 0 | 0 | 0 | 0 | 0 | 0 | 0 | 0 | 0 | 0 | 0 | 0 | 0 | 0 | 0 | 0 | 0.19 |
| IGKV4-61 | 0 | 0 | 0 | 0 | 0 | 0 | 0.19 | 0 | 0 | 0.19 | 0 | 0 | 0 | 0 | 0 | 0 | 0 | 0 | 0 | 0 | 0 |
| IGKV4-63 | 0 | 0 | 0 | 0 | 0 | 0 | 0 | 0 | 0 | 0.19 | 0 | 0.19 | 0.39 | 0 | 0 | 0 | 0 | 0 | 0 | 0 | 0 |
| IGKV4-68 | 0 | 0 | 0 | 0 | 0 | 0 | 0 | 0 | 0 | 0 | 0 | 0 | 0 | 0 | 0 | 0.39 | 0 | 0 | 0 | 0 | 0 |
| IGKV4-70 | 0 | 0 | 0 | 0 | 0 | 0 | 0 | 0 | 0 | 0 | 0 | 0 | 3.3 | 0 | 0 | 0.19 | 0 | 0 | 0 | 0 | 0 |
| IGKV4-72 | 0 | 0 | 0 | 0 | 0 | 0 | 0 | 0 | 0 | 0 | 0 | 0 | 0 | 0 | 0 | 0 | 0 | 0 | 0 | 0.19 | 0 |
| IGKV4-74 | 0 | 0 | 0 | 0 | 0 | 0 | 0 | 0 | 0 | 0 | 0 | 0 | 0 | 0 | 0 | 0.19 | 0 | 0.19 | 0 | 0 | 0 |
| IGKV4-80 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV5-45 | 0 | 0 | 0 | 0 | 0 | 0 | 0 | 0.39 | 0 | 0 | 0 | 0 | 0 | 0 | 0 | 0 | 0 | 0 | 0 | 0 | 0 |
| IGKV5-48 | 0 | 0 | 0 | 0 | 0 | 0 | 0 | 0 | 0 | 0 | 0 | 0.19 | 0 | 0 | 0 | 0 | 0 | 0 | 0 | 0 | 0 |
| IGKV6-15 | 0 | 0 | 0 | 0 | 0 | 0 | 0 | 0 | 0 | 0 | 0 | 0 | 0 | 0 | 0 | 0 | 0 | 0.19 | 0 | 0 | 0 |
| IGKV6-17 | 0 | 0 | 0 | 0 | 0 | 0 | 0 | 0 | 0 | 0 | 0 | 0 | 0 | 0 | 0 | 0.19 | 0 | 0 | 0 | 0 | 0 |
| IGKV6-20 | 1.94 | 0 | 0 | 0 | 0 | 0 | 0 | 0 | 0 | 0 | 0 | 0 | 0 | 0 | 0 | 0 | 0 | 0 | 0 | 0 | 0 |
| IGKV6-23 | 0 | 0 | 0.39 | 0 | 0 | 0 | 0 | 0 | 0 | 0.19 | 0 | 0 | 0 | 0 | 0.39 | 0.19 | 0 | 0 | 0 | 0 | 0 |
| IGKV6-32 | 0 | 0 | 0 | 0.19 | 0 | 0 | 0.19 | 0 | 0 | 0 | 0 | 0 | 0 | 0.19 | 0 | 0 | 0 | 0 | 0.19 | 0.19 | 0 |
| IGKV8-19 | 0 | 0 | 0 | 0 | 0 | 0 | 0 | 0 | 0 | 0 | 0 | 0 | 0 | 0.19 | 0 | 0 | 0 | 0 | 0 | 0 | 0 |
| IGKV8-21 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV8-24 | 0 | 0 | 0 | 0 | 0 | 0 | 0.19 | 0 | 0.78 | 0 | 0 | 0 | 0 | 0 | 0 | 0 | 0 | 0 | 0 | 0 | 0 |
| IGKV8-30 | 0 | 0 | 0 | 0 | 0 | 0 | 0.19 | 0 | 0 | 0 | 0 | 0 | 0 | 0 | 0.19 | 4.08 | 0 | 0 | 0.58 | 0 | 0.19 |
| IGKV9-120 | 0 | 0 | 0 | 0 | 0 | 0 | 0 | 0 | 0 | 0 | 0 | 0 | 0 | 0 | 0 | 0.19 | 0 | 0 | 0 | 0 | 0 |
| IGKV9-124 | 0 | 0 | 0 | 0 | 0 | 0 | 0 | 0 | 0 | 0 | 0 | 0 | 0 | 0.19 | 0 | 0 | 0 | 0 | 0 | 0 | 0 |
| IGKV10-94 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV10-96 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV11-125 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV12-41 | 0 | 0 | 0 | 0 | 0 | 0 | 0 | 0 | 0 | 0 | 0 | 0 | 0 | 0.19 | 0 | 0 | 0 | 1.17 | 0 | 0 | 0 |
| IGKV12-44 | 0 | 0 | 0 | 0 | 0 | 0 | 0 | 0 | 2.33 | 0.58 | 0 | 0 | 0 | 0 | 0 | 0 | 0 | 1.17 | 0 | 0 | 0 |
| IGKV12-89 | 0 | 0 | 0 | 0 | 0 | 4.27 | 0 | 0 | 0 | 0 | 0 | 0 | 0 | 0 | 0 | 0 | 0 | 0 | 0 | 0 | 0 |
| IGKV13-84 | 0 | 0 | 0 | 0 | 0 | 0 | 0 | 0 | 0 | 0 | 0 | 0 | 0 | 0 | 0 | 0 | 0 | 0 | 0 | 0 | 0 |
| IGKV14-111 | 0 | 0 | 0.19 | 0 | 0 | 0 | 0 | 0 | 0 | 0 | 0 | 0.19 | 0 | 0 | 0 | 0 | 0 | 0 | 0 | 0.19 | 0 |
| IGKV15-103 | 0 | 0 | 0 | 0 | 0 | 0 | 0.19 | 0 | 0 | 0 | 0 | 0 | 0 | 0 | 0 | 0 | 0 | 0 | 0 | 0.19 | 0 |
| IGKV17-127 | 0 | 0.19 | 0 | 0 | 0 | 0 | 0 | 0 | 0 | 0 | 0 | 0 | 0 | 0 | 0 | 0 | 0 | 0 | 0 | 0 | 0 |
| IGKV19-93 | 0 | 0 | 0 | 0 | 0 | 0 | 0.78 | 0 | 0 | 0 | 0.39 | 0 | 0 | 0 | 0 | 0.19 | 0 | 0 | 0 | 0 | 0 |
| IGLV1 | 0 | 0.19 | 0 | 0 | 0 | 0 | 0 | 0 | 0 | 0 | 0 | 0 | 0 | 0 | 0 | 0 | 0 | 0 | 0 | 0 | 0 |

FIG. 24-2

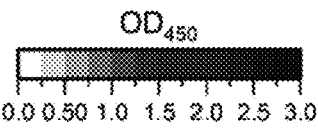
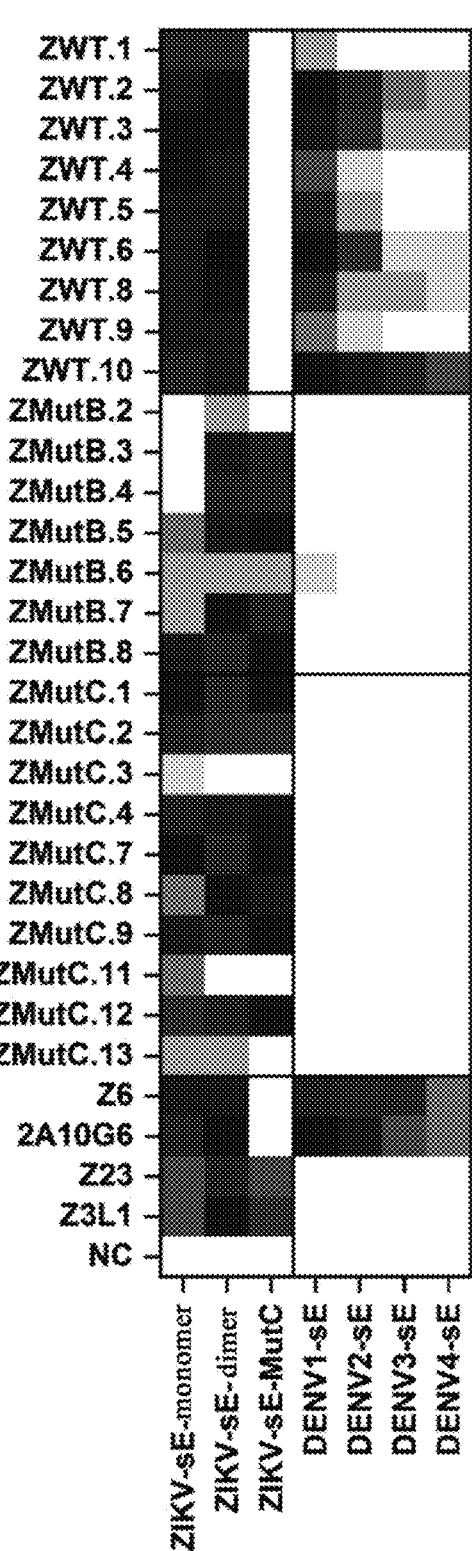
FIG. 25

A

Heavy chain sE_MutC dimer

Z3L1 binding with sE WT/MutC

A MutCoverlapped with Z6/ZIKV sE    B MutC overlapped with 2A10G6/ZIKV sE    C MutC overlapped with E53/WNV sE

ZIKA/DENGUE VACCINE AND APPLICATION THEREOF

CROSS-REFERENCE TO RELATED APPLICATIONS

This application is a U.S. National-Stage entry under 35 U.S.C. § 371 based on International Application No. PCT/CN2020/127614, filed November 9, 220, which was published under PCT Article 21(2) and which claims the priority to Chinese Patent Application No. 201911082867.5, filed Nov. 7, 2019, the entire content of which are incorporated in their entirety by reference.

SEQUENCE LISTING

The content of the ASCII text file of the sequence listing named Sequence_Listing.txt, which is 62.8 KB in size, was created on Sep. 30, 2022 and electronically submitted via EFS-Web along with the present application, and is incorporated by reference in its entirety.

TECHNICAL FIELD

The present disclosure relates to the field of biotechnology, specifically, to a field of Zika/dengue vaccine and its application thereof.

BACKGROUND

Zika virus (ZIKV) is a mosquito-borne virus, belonging to the genus Flavivirus of the family Flaviviridae. The ZIKV outbreak in the Americas in 2015-2016 spreaded to 84 countries around the world, including China. However, no vaccines and drugs are available so far. Although the global incidence of ZIKV infection has now weakened, ZIKV still poses a threat to people living in endemic areas. Therefore, development of a ZIKV vaccine is urgent.

DENV virus (dengue virus, DENV) has four serotypes and is also a mosquito-borne virus belonging to the genus Flavivirus of the family Flaviviridae.

The structures of ZIKV virus and DENV virus are relatively similar, both of which are icosahedral spherical structures with an envelope. The surface of the envelope contains an envelope (Envelope, E) protein. The internal viral genome is a single-stranded positive-stranded RNA, about 11kb in length, with only one open reading frame. The translated polyprotein can be cleaved into 3 structural proteins (C, prM, and E) and 7 non-structural proteins (NS1, NS2A, NS2B, NS3, NS4A, NS4B, and NS5).

The E protein is about 53 kD in size and is the main protein on the surface of ZIKV and DENV, which mediates entry of a virus into cells via membrane fusion. Thus, it is an important target for activating neutralizing antibodies. At the same time, E protein is also an important target protein when designing vaccines. The E protein has 504 amino acids and exists as a dimer. Each monomer has three domains, DI, DII, and DIII, respectively. The head of DII (98-109 amino acids) contains a highly conserved fusion loop (FL), in which the sequences of the FL region in both ZIKV virus and DENV virus are completely identical, being D98-R99-G100-W101-G102-N103-G104-C105-G106-L107-F108-G109. The FL region plays a key role in the membrane fusion process of virus invasion. During virus infection, immune cells will produce a large number of antibodies against FL.

The size of prM protein is about 26kD, which assists in the correct folding of the E protein. The transmembrane region at the 3' end of prM/E serves as an endoplasmic reticulum retention signal to assist prM and E to form a heterodimer. One of the main functions of the prM protein is to maintain the stability of the E protein. In immature virus particles, the pr polypeptide is located at the tip of the E protein, forming a pr-E spike, which hides the fusion peptide of the E protein. At this time, prM is not easily to be contacted with and cleaved by furin due to steric hindrance. After that, the acidic environment in the Golgi body induces a rearrangement reaction that exposes the cleavage site of furin, and the prM protein is cleaved by furin into the M protein. At this time, the cleaved pr polypeptide is not immediately dissociated from the virion. Instead, the pr polypeptide needs to be exposed to a neutral pH cellular environment before it is released and presents a mature virion.

Since the genetic composition and antigenic properties of ZIKV are very similar to those of the four serotypes of dengue virus (DENV) with amino acid similarity of about 56%, the antibodies induced by ZIKV infection will have strong cross-reactivity to DENV This is also a factor to be considered in the issue of vaccine safety. There are substantial evidences showing that pre-existing antibodies following ZIKV infection can enhance a subsequent DENV infection due to cross-reactivity with DENV (Fowler et al., 2018; George et al., 2017; Li et al., 2017; Richner et al., 2017; Stettler et al., 2016; Valiant et al., 2018). This phenomenon is called antibody-dependent enhancement (ADE). ADE refers to an antibody enhances viral infection when the antibody is insufficient to neutralize the virus or at a sub-neutralizing concentration (Beltramello et al., 2010; Dejnirattisai et al., 2010). Although epidemiological investigations are still insufficient, pre-existing ZIKV antibodies from human beings, monkeys, and mice have all been shown to enhance DENV infection in cellular experiments (George et al., 2017; Richner et al., 2017; Stettler et al., 2016; Valiant et al., 2018). In addition, it is confirmed in monkey and mouse models that symptoms of DENV infection can be exacerbated by antibodies obtained from ZIKV infection, from vaccine immunization, or by a fetus from the mother (Fowler et al., 2018; George et al., 2017; Richner et al., 2017; Stettler et al., 2016). Therefore, it should be considered that ZIKV vaccine may have an ADE effect on future DENV infection after immunization during ZIKV vaccine design.

Antibodies that elicit ADE responses are mainly induced by the FL fusion region of the virus (Beltramello et al., 2010; Dejnirattisai et al., 2010). In *Flavivirus* infections, such antibodies account for a large proportion of the total induced antibodies. These antibodies often cross-react between different serotypes due to highly conserved epitopes. Most of the antibodies also have low neutralizing activity, which easily lead to ADE reaction. However, most of the antibodies with high neutralizing activity bind to other epitopes of the E protein. A series of ZIKV neutralizing monoclonal antibodies targeting Domain I (DI), Domain II (DII) and Domain III (DIII) or quaternary epitopes of the E protein have been identified (Barba-Spaeth et al., 2016; Stettler et al., 2016; Wang et al., 2017; Wang et al., 2016; Zhao et al., 2016). Therefore, an ideal ZIKV vaccine design strategy is to transfer the hot spot epitopes of the immune response from the FL region to other neutralizing epitopes.

Antibodies are absorbed by cells through binding to virions and then binding to the Fe γ receptor protein on the surface of myeloid cells, which subsequently promote viral infection. Since DENV has four serotypes, ADE is likely to occur when someone is infected with DENV a second time with a different serotype, which explains the more severe disease phenomenon in human beings after DENV infection (Katzelnick et al., 2017). ADE is used to explain the application limitations of the only currently approved DENV vaccine, Dengvaxia®, which is recommended only for use in DENV seropositive individuals, while an injection of the vaccine can actually exacerbate the risk of dengue infection for seronegative individuals (Rey et al., 2018; Slon-Campos et al., 2019). Therefore, it is also a challenge to avoid ADE during DENV vaccine development.

The disclosure in the background is merely to enhance the understanding of the general background and should not be perceived as an acknowledgement or any form of indication that the disclosure forms the prior art known to those of ordinary skill in the art.

SUMMARY

The application aims to provide a Zika/dengue vaccine and its application to avoid ADE effect. The present application has obtained the epitope information of an antibody that causes ADE effect using crystal structure analysis and other structural and functional analysis. The present application provides antigens, for which some mutations are introduced into the E-protein FL fusion region of either a Zika virus or a dengue virus. Antigens with said mutations are unable to bind to antibodies that causes ADE (FLE antibody). One embodiment of the present application also provides a vaccine, which can avoid the production of antibodies induced by the FL epitope after immunization, thereby reducing or eliminating the ADE effect.

In order to achieve the purpose, the examples provides an antigen, having an E protein FL fusion region of Zika virus or dengue virus, wherein the E protein FL fusion region comprises one of the following mutations:

(1) one or two of D98 and N103 site mutations in combination with a three-site mutation of G106, L107 and F108;

(2) one of G106, L107, and F108 site mutations or their combinations; and (3) a single-site mutation of W101.

(1) one or two of D98 and N103 site mutations in combination with a three-site mutation of G106, L107 and F108 is any one of the following: a five-site mutation of D98, N103, G106, L107, and F108; a four-site mutation of D98, G106, L107, and F108; and a four-site mutation of N103, G106, L107, and F108.

(2) one of G106, L107, and F108 site mutations or their combinations is any one of the following: a single-site mutation selected from the group consisting of G106, L107, and F108 site mutations; a double-site mutation selected from any two of G106, L107, and F108 site mutations; a three-site mutation of G106, L107, and F108.

D98 site mutation refers to the substitution of an aspartic acid (D) at position 98 of E protein with any amino acid except aspartic acid;

N103 site mutation refers to the substitution of an asparagine (N) at position 103 of E protein with any amino acid except asparagine;

G106 site mutation refers to the substitution of a glycine (G) at position 106 of the E protein with any amino acid except glycine;

L107 site mutation refers to the substitution of leucine (L) at position 107 of protein E with any amino acid except leucine;

F108 site mutation refers to the substitution of phenylalanine (F) at position 108 of protein E with any amino acid except phenylalanine;

W101 site mutation refers to the substitution of tryptophan (W) at position 101 of E protein with any amino acid except tryptophan.

D98 site, W101 site, N103 site, G106 site, L107 site or F108 site is located in the E protein FL fusion region. The FL (fusion region) sequence of genus *Flavivirus* is highly conservative, and the FL sequences of ZIKV virus and DENV virus are completely identical as D98-R99-G100-W101-G102-N103-G104-C105-G106-L107-F108-G109. In one aspect, the numbering of D98, W101, N103, G106, L107 and F108 sites refers to the position in the E protein sequences of Zika virus and dengue virus. Specifically, examples can be refered to the 98, 101, 103, 106, 107 and 108 sites of E protein of the Zika virus shown in SEQ ID NO. 1 (e.g. ZIKV FSS13025 strain, GenBank: JN860885.1).

In a possible embodiment of the above antigen, the mutation of the E protein FL fusion region is a five-site mutation of D98, N103, G106, 107 and F108;

or, the mutation in the E protein FL fusion region is a three-site mutation of G106, L107 and F108;

or, the mutation in the E protein FL fusion region is a double-site mutation of G106 and L107;

or, the mutation in the E protein FL fusion region is a double-site mutation of G106 and F108;

or, the mutation in the E protein FL fusion region is a double-site mutation of L107 and F108;

or, the mutation in the E protein FL fusion region is a single-site mutation of G106;

or, the mutation in the E protein FL fusion region is a single-site mutation of L107;

or, the mutation in the E protein FL fusion region is a single-site mutation of F108;

or, the mutation in the E protein FL fusion region is a single-site mutation of W101.

In a possible embodiment of the above antigen, the mutation of the E protein FL fusion region is selected from any one or a combination of the following groups consisting of different mutation forms:

| Mutation site | Mutation form |
| --- | --- |
| Five-site mutations of D98/N103/G106/L107/F108 | D98N/N103T/G106F/L107E/F108W |
| | D98N/N103T/G106F/L107K/F108W |
| | D98N/N103T/G106L/L107E/F108W |
| Three site mutations of G106/L107/F108 | G106F/L107E/F108W |
| | G106F/L107K/F108W |
| | G106L/L107E/F108W |
| Double site mutations of G106/L107 | G106L/L107E |
| | G106L/L107K |
| | G106F/L107E |
| | G106F/L107K |
| | G106F/L107R |
| Double site mutations of G106/F108 | G106F/F108W |
| | G106L/F108W |
| | G106F/F108H |
| | G106Y/F108W |
| | G106W/F108Y |
| Double site mutations of L107/F108 | L107E/F108W |
| | L107K/F108W |
| | L107R/F108W |
| | L107D/F108W |
| | L107K/F108Y |
| Single site mutation of G106 | G106L |
| | G106F |

5

-continued

| Mutation site | Mutation form |
|---|---|
| | G106W |
| | G106Y |
| | G106I |
| Single site mutation | L107E |
| of L107 | L107K |
| | L107R |
| | L107D |
| | L107T |
| Single site mutation | F108W |
| of F108 | F108H |
| | F108Y |
| | F108P |
| | F108A |
| Single site mutation of W101 | W101A |
| | W101R |
| | W101N |
| | W101D |
| | W101C |
| | W101Q |
| | W101E |
| | W101G |
| | W101H |
| | W101I |
| | W10IL |
| | W101K |
| | W101M |
| | W101F |
| | W101P |
| | W101S |
| | W101T |
| | W101Y |
| | W101V |

In the above table,

D98N mutation refers to the substitution of aspartic acid (D) at position 98 of E protein with asparagine (N).

N103T mutation refers to the substitution of asparagine (N) at position 103 of E protein with threonine (T).

G106F mutation refers to the substitution of glycine (G) at position 106 of E protein with phenylalanine (F);

G106L mutation refers to the substitution of glycine (G) at position 106 of E protein with leucine (L).

L107E mutation refers to the substitution of leucine (L) at position 107 of E protein with glutamic acid (E);

L107K mutation refers to the substitution of leucine (L) at position 107 of E protein with lysine (K).

F108W mutation refers to the substitution of phenylalanine (F) at position 108 of the E protein with tryptophan (W).

Mutations of amino acids are deduced for the rest, and the type of the amino acid represented by a single letter is the general understanding of those skilled in the art.

In a possible embodiment, the antigen comprises the E protein FL fusion region of Zika virus, the antigen further comprises a full sequence or a partial sequence of M protein of Zika virus; preferably, the antigen further comprises a full sequence of M protein of Zika virus;

when the antigen comprises the E protein FL fusion region of dengue virus, the antigen further comprises a full sequence or a partial sequence of M protein of dengue virus; preferably, the antigen further comprises a full sequence of M protein of dengue virus.

M protein is formed when prM structural protein is cleaved by furin. The full sequence or the partial sequence of M protein refers to 0.5%-100%, 50-100%, 60-100%, 70-100%, 80-100%, 90-100% sequence similarity of the M protein, the sequence can be either a sequence selected continuously from the M protein or a combination of fragments selected separately from the M protein.

In a possible embodiment, the antigen comprises the E protein FL fusion region of Zika virus, the antigen further comprises a full sequence or a partial sequence of prM protein of Zika virus; preferably, the antigen further comprises a full sequence of prM protein of Zika virus;

when the antigen comprises the E protein FL fusion region of dengue virus, the antigen further comprises a full sequence or a partial sequence of prM protein of dengue virus; preferably, the antigen further comprises a full sequence of prM protein of dengue virus.

The prM protein is a structural protein of Zika virus or dengue virus, with a size of about 26 kD, and is used for assisting in the correct folding of the E protein. The full sequence or the partial sequence of prM protein refers to 0.5%-100%, 50-100%, 60-100%, 70-100%, 80-100%, 90-100% sequence similarity of the prM protein, the sequence can be either a sequence selected continuously from the prM protein or a combination of fragments selected separately from the prM protein.

In a possible embodiment, the antigen comprises the E protein FL fusion region of Zika virus, the antigen further comprises a full sequence or a partial sequence of E protein of Zika virus; preferably, the antigen further comprises a full sequence of E protein of Zika virus;

when the antigen comprises the E protein FL fusion region of dengue virus, the antigen further comprises a full sequence or a partial sequence of E protein of dengue virus; preferably, the antigen further comprises a full sequence of E protein of dengue virus.

The full sequence or the partial sequence of E protein refers to 0.5%-100%, 50-100%, 60-100%, 70-100%, 80-100%, 90-100% sequence similarity of the E protein, the sequence can be either a sequence selected continuously from the E protein, or a combination of fragments selected separately from the E protein.

The E protein, prM protein, and M protein sequences of Zika virus can be obtained according to the full sequences of Zika virus strain disclosed in NCBI and the prior art. The E protein, prM protein, M protein sequences of dengue virus can be obtained according to the full sequences of four serotypes of dengue virus strain disclosed in NCBI and the prior art.

In a possible embodiment of the above antigen, the Zika virus includes all Zika virus strains, such as ZIKV FSS13025 strain (GenBank: JN860885.1) and ZIKK SMGC-1 strain.

In a possible embodiment of the above antigen, the dengue virus includes four serotypes of dengue virus strains, such as DENV1 (Hawaii strain, GenBank: KM204119), DENV2 (New Guinea C strain, GenBank: KM204118.1), DENV3 (YNO2 strain, GenBank: KF824903) and DENV4 (B5 strain, Guangzhou, China, GenBank: AF289029).

One embodiment of the present disclosure also provides an antigen binding epitope of E protein FL fusion region of Zika virus, wherein the E protein FL fusion region of Zika virus is the amino acid sequence of D98-R99-G100-W101-G102-N103-G104-C105-G106-L107-F108-G109, which comprises one of the following mutations:

(1) one or two of D98 and N103 site mutations in combination with a three-site mutation of G106, L107 and F108;

(2) one of G106, L107, and F108 site mutations or their combinations; and (3) a single-site mutation of W101.

One embodiment of the present disclosure also provides a Zika virus antigen comprising the above-mentioned antigen binding epitope.

In a possible embodiment, the above-mentioned Zika virus antigen also comprises one or more of the following sequences:

a full sequence or a partial sequence of Zika virus E protein;

a full sequence or a partial sequence of Zika virus M protein;

a full sequence or a partial sequence of Zika virus prM protein.

One embodiment of the present disclosure also provides an antigen binding epitope of E protein FL fusion region of dengue virus, wherein the E protein FL fusion region of dengue virus is the amino acid sequence of D98-R99-G100-W101-G102-N103-G104-C105-G106-L107-F108-G109, which comprises one of the following mutations:

(1) one or two of D98 and N103 site mutations in combination with a three-site mutation of G106, L107 and F108;

(2) one of G106, L107, and F108 site mutations or their combinations; and (3) a single-site mutation of W101.

One embodiment of the present disclosure also provides a dengue virus antigen comprising the above-mentioned antigen binding epitope.

In a possible embodiment, the above-mentioned dengue virus antigen also comprises one or more of the following sequences:

a full sequence or a partial sequence of dengue virus E protein;

a full sequence or a partial sequence of dengue virus M protein;

a full sequence or a partial sequence of dengue virus prM protein.

One embodiment of the present disclosure also provides an antibody that obtained from the above-mentioned antigen, the above-mentioned Zika virus antigen, and the above-mentioned dengue virus antigen.

One embodiment of the present disclosure also provides a polynucleotide encoding the above-mentioned antigen, the above-mentioned antigen binding epitope, the above-mentioned Zika virus antigen, and the above-mentioned dengue virus antigen.

One embodiment of the present disclosure also provides an expression cassette, recombinant vector, transgenic cell line, recombinant bacteria, adenovirus, lentivirus or viral particle comprising the above-mentioned polynucleotide.

One embodiment of the present disclosure also provides an mRNA encoding the above-mentioned antigen, the above-mentioned antigen binding epitope, the above-mentioned Zika virus antigen, and the above-mentioned dengue virus antigen.

One embodiment of the present disclosure also provides a vaccine, that comprises the above-mentioned antigen, the above-mentioned Zika virus antigen, the above-mentioned dengue virus antigen, the above-mentioned polynucleotide, the above-mentioned expression cassette, recombinant vector, transgenic cell line, recombinant bacteria, adenovirus viruses, lentiviruses or virus particles, or the above-mentioned mRNA as active ingredients.

In a possible embodiment of the above vaccine, the vaccine is one or more of an inactivated vaccine, an attenuated vaccine, a DNA vaccine, an mRNA vaccine, an adenovirus vaccine, other viral vector vaccines, a subunit vaccine or viral particles.

In a possible embodiment of the above vaccine, the vaccine is an adenovirus vaccine.

In a possible embodiment of the above vaccine, the vaccine further comprises a pharmaceutically or veterinarily acceptable vehicle, diluent, adjuvant or excipient.

One embodiment of the present disclosure also provides use of the above-mentioned antigens, the above-mentioned antigen binding epitopes, the above-mentioned antibodies, the above-mentioned polynucleotides, the above-mentioned expression cassettes, recombinant vectors, transgenic cell lines, recombinant bacteria, adenoviruses, lentiviruses or virus particles, or the above-mentioned mRNAs in the manufacture of a vaccine for preventing and/or treating infections of viruses of genus *Flavivirus*.

One embodiment of the present disclosure also provides use of the above-mentioned antigens, the above-mentioned antigen binding epitopes, the above-mentioned antibodies, the above-mentioned polynucleotides, the above-mentioned expression cassettes, recombinant vectors, transgenic cell lines, recombinant bacteria, adenoviruses, lentiviruses or virus particles, or the above-mentioned mRNAs in the manufacture of detection reagents or kits for detecting infections of viruses of genus *Flavivirus*.

Beneficial Effects (1) Firstly, the present application has obtained the epitope information of an antibody that causes ADE effect based on crystal structure analysis and other structural and functional analysis. For the antigen provided in the examples of the present application, one of the following mutations is introduced into the E protein FL fusion region of Zika virus or dengue virus: i. one or two of D98 and N103 site mutations in combination with a three-site mutation of G106, L107 and F108; ii. one of G106, L107, and F108 site mutations or their combinations; iii. a single-site mutation of W101.

Antigens with said mutations are unable to bind to antibodies that causes ADE (FLE antibody). One embodiment of the present application also provides a vaccine, which can avoid the production of antibodies induced by the FL epitope after immunization, thereby reducing or eliminating the ADE effect.

(2) Secondly, the antigens provided in the examples of the present application cannot bind to the antibody (FLE antibody) that causes ADE. However, the binding ability of the antigen to antibodies targeting other epitopes is not affected. The present application provides examples of several adenovirus vaccines of Zika virus obtained from said antigens, and proves that the obtained recombinant adenovirus vaccine does not reduce the immunogenicity of the antigen, and can still activate the neutralizing antibodies. Moreover, adenovirus vaccines of Zika virus plays a role of protection in virus challenge assay of mice; it can well protect mice against viremia and infection of tissues and organs, and reduce or even eliminate the ADE effect of four serotypes of DENV virus after immunization.

Also, the prevent application proves that the mutated E protein maintains its dimer form with only the amino acid side chain of FL has been changed, which does not change the epitopes of other neutralizing antibodies. Single-cell sequencing of germinal center (GC) B cells is used to analyze the antibody responses induced by recombinant adenovirus vaccine in mice, which demonstrates that recombinant adenovirus vaccines with mutated FL regions significantly reduced FL epitope-induced antibodies compared to vaccines with wild-type FL regions, since the dominant epitope of the antigen has been transferred. This well explains the mechanism how the vaccine obtained from the antigen of the present application is able to eliminate the ADE effect.

(3) The present application also takes the expression plasmids of several adenoviruses of dengue virus as an example, and proves that none of the obtained antigens can bind to the antibody (FLE antibody) that causes ADE. This demonstrates that after immunization with the dengue virus vaccine obtained by the antigen of the present application, the production of antibodies induced by the FL epitope can be avoided, thereby reducing or eliminating the ADE effect caused by the subsequent DENV virus infection.

(4) The vaccines obtained from the antigens provided by the present application can be various informs, such as nucleic acid vaccines, mRNA vaccines, adenovirus vector vaccines, other virus vector vaccines, virus-like particles, virus attenuated vaccines or inactivated vaccines based on the antigenic sequences, chimeric vaccines with other backbones, and the like, which can be used to prepare Zika and quadrivalent dengue vaccines that eliminate the effect of ADE.

BRIEF DESCRIPTION OF THE DRAWINGS

One or more examples are exemplified by the figures in the corresponding drawings, and these exemplified descriptions do not constitute limitations on the examples. The term "exemplified" used herein means "serving as an instance, example, or illustration". Any examples described herein as "exemplified" is not necessarily to be interpreted as preferred or advantageous over other examples.

FIG. 5 shows the complex structure of different antibodies and E protein of the genus *Flavivirus*, wherein, A is the complex structure of Z6 antibody and ZIKV E protein, B is the complex structure of 2A10G6 antibody and ZIKV E protein, C is the complex structure of E53 antibody and WNV E protein, and D is an overlap of the structure of the three antibodies and ZIKV E protein.

FIG. 6 shows the amino acid site analysis of ZIKV E protein binding to Z6 antibody, ZIKV E protein binding to 2A10G6 antibody, and WNV E protein binding to E53 antibody.

FIG. 22 shows the result of paired HV and LV in antibody profile induced by immunization of BALB/c mice with AdC7-M/E-WT vaccine.

FIG. 23 shows the result of paired HV and LV in antibody profiles induced by immunization of BALB/c mice with AdC7-M/E-MutB vaccine.

FIG. 24-1 shows the result of paired HV and LV in the antibody profile induced by immunization of BALB/c mice with AdC7-M/E-MutC vaccine.

FIG. 24-2 shows the result of paired HV and LV in the antibody profile induced by immunization of BALB/c mice with AdC7-M/E-MutC vaccine.

FIG. 25 shows the result of identification of antibodies induced by immunization of BALB/c mice with ZIKV recombinant adenovirus vaccine and the binding ability to different ZIKV E proteins and DENV E proteins.

FIG. 28-1 shows the result of the comparison of the sequence similarity between the monoclonal antibody induced in mice immunized by AdC7-M/E-WT vaccine and the reported FLE monoclonal antibody.

FIG. 28-2 shows the result of the comparison of the sequence similarity between the monoclonal antibody induced in mice immunized by AdC7-M/E-WT vaccine and the reported FLE monoclonal antibody.

FIG. 35 A, B and C is a Z6 antibody and ZIKV sE protein, a 2A10G6 antibody and ZIKV sE protein (PDB: 5JHL), a E53 antibody and WNV sE protein (PDB: 3I50), respectively.

DETAILED DESCRIPTION

Figure 1:
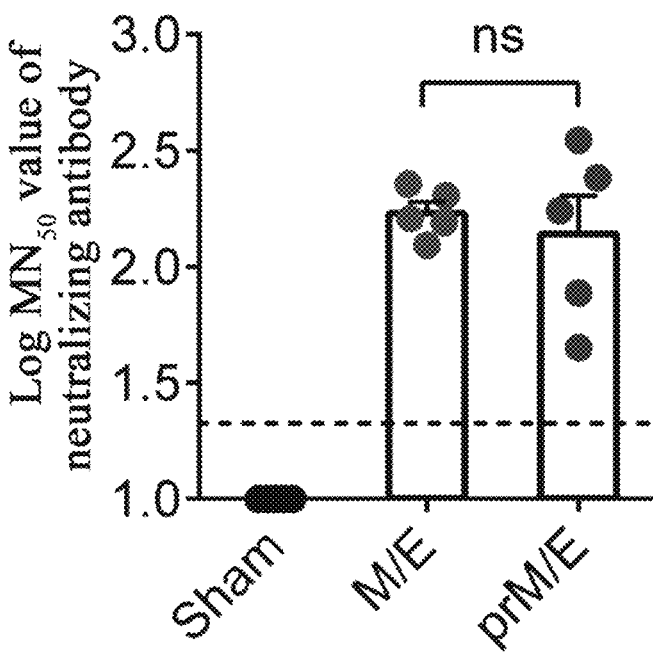
FIG. 1 shows the result of neutralization test in mice immunized with wild-type recombinant adenovirus vaccines AdC7-M/E-WT and AdC7-prM/E-WT.

In order to more clearly illustrate the objects, technical solutions and advantages of the examples of the present disclosure, the technical solutions in the examples of the present disclosure will be clearly and completely described in the following. It is obvious that the described examples are a part of the examples of the present disclosure, but not all of them. All other examples obtained by an ordinary skilled person in the art based on the examples of the present disclosure without creative efforts shall be within the scope of the present disclosure. Unless specifically stated otherwise, the term "comprising" or variations thereof such as "including" or "having" and the like used throughout the specification and claims will be understood to include the stated element or component, and other elements or other components are not excluded.

In addition, in order to better illustrate the present disclosure, numerous specific details are given in the following detailed description. It will be understood by those skilled in the art that the present disclosure may be implemented without certain specific details. In some examples, materials, elements, methods, means, etc. that are well known to those skilled in the art are not described in detail, so as to highlight the subject of the present disclosure.

Example 1 Detection of Humoral Immune Responses in Mice Induced by Recombinant Chimpanzee Adenovirus Vaccine Constructed with ZIKV Wild-Type M/E and prM/E Antigens The M/E antigen of ZIKV FSS13025 virus strain (GenBank: JN860885.1) was constructed into type 7 chimpanzee adenovirus vector. After packaging, culture and purification of the adenovirus, the recombinant adenovirus vaccine AdC7-M/E-WT was obtained (the recombinant adenovirus vaccine AdC7-M/E-WT: Xu et al. (2018) Journal of virology. vol. 92, 6 e01722-17. 26 February as the construction control). Experimental results show that it had a good protective effect on mice. It has been reported in literatures that the adenovirus vaccine constructed with ZIKV prM/E antigen also has protective effect. Therefore, the prM/E antigen of ZIKV-SMGC-1 virus strain was constructed into type 7 chimpanzee adenovirus vector, and the recombinant adenovirus AdC7-prM/E-WT was obtained after packaging (Recombinant adenovirus AdC7-prM/E-WT was constructed according to Hassan, Ahmed O et al. (2019) Cell reports, vol. 28, 10: 2634-2646.e4.), as a control for subsequent experiments.

Evaluation of humoral immune responses in mice induced by recombinant adenovirus vaccines AdC7-M/E-WT and AdC7-prM/E-WT:

15 BALB/c mice were randomly divided into 3 groups and immunized with $1.6 \times 10^{11}$ vp (virus particles) of AdC7-M/E-WT adenovirus vaccine, AdC7-prM/E-WT adenovirus vaccine and PBS, respectively. After 4 weeks, the blood was collected. The blood was centrifuged to obtain serum. The serum was inactivated by heating at 56° C. for 30 minutes, and the neutralizing antibody titer of the serum was detected by a micro-neutralization assay.

The process of the micro-neutralization assay was as follows: VERO cells were plated in a 96-well plate one day in advance. The serum was diluted with gradient in 1% FBS (Gibco, 10270-106) in DMEM medium (Invitrogen, C11995500BT) using a 96-well plate the next day. The virus was also diluted with 1% FBS in DMEM medium. The serum and the virus solution were mixed. 100 FFU ZIKV-SMGC-1 was added to each well, and incubated at 37° C. for 2 hours. The supernatant of the medium was removed from the VERO cell plate. A mixture of serum and virus was added, and cultured for 2 hours. After that, DMEM containing 10% FBS was supplemented. The cells were cultured in a 37° C. incubator for 4 days. After 4 days, the cell culture plate was taken out. All supernatant was discarded. The precipitate was washed once with PBS. 150 μl methanol was added for fixation, which was placed in −20° C. refrigerator for 15-20 minutes, and then washed twice with PBS. 2% nonfat milk (blocking solution) in PBS was used for blocking for 30 minutes at room temperature, and then primary antibody was added. The primary antibody was Z6 antibody that binds to ZIKV E protein, diluted to a working concentration of 5 g/mL with blocking solution, incubated at room temperature for 2 hours, and then washed 3 times with PBST. After that, secondary antibody was added. The secondary antibody was a goat anti-human antibody conjugated to HRP (Proteintech, SA00001-17), which was diluted 1500-fold with blocking solution, incubated at room temperature for 2 hours, and then washed 4 times with PBST. 50 μl of TMB chromogenic solution (Biyuntian, P0209) was added, which was incubated at room temperature, and reacted for about 20 minutes. The color change was monitored, and 50 μl of 2 M hydrochloric acid was added to stop the reaction. The OD450 absorbance value was read on a microplate reader. GraphPad Prism software was used to perform nonlinear fitting on the data to calculate the corresponding serum dilution ratio of neutralizing 50% of the cell infection, as the neutralization titer value ($MN_{50}$). When the serum at the lowest dilution ratio was still unable to neutralize 50% of the cell infection, the $MN_{50}$ of the sample was defined as half of the lowest dilution.

The results of the neutralization assay were shown in FIG. 1. The group immunized with PBS was the negative control group, Sham group (represented by Sham in the figure), and no neutralizing antibodies can be detected in the serum of this group. The log $MN_{50}$ average value of neutralizing antibodies can be detected in mice in both AdC7-M/E-WT group (indicated by M/E in the figure) and the AdC7-prM/E-WT group (indicated by prM/E in the figure), which were between 2 and 2.5. There was no significant difference between the two groups in statistical analysis, indicating that the recombinant adenovirus vaccines AdC7-M/E-WT and AdC7-prM/E-WT both induce mice to produce relatively high levels of neutralizing antibodies.

Example 2 In Vitro Experiments to Detect the ADE of DENV in Serums from Mice Immunized with Wild-Type Recombinant Adenovirus Vaccine AdC7-M/E-WT and AdC7-prM/E-WT Since the fusion loop (FL) sequence of the envelope (E) protein of viruses of genus *Flavivirus* is highly conserved, infection with ZIKV or immunization with a vaccine expressing the ZIKV E protein can induce the production of antibodies that cross-react with DENV, resulting in an antibody-dependent enhanced response to DENV (ADE) (Stettler, K., et al. (2016) Science: science. aaf8505.). Therefore, it was tested whether the serums from mice immunized with the recombinant adenovirus vaccines AdC7-M/E-WT and AdC7-prM/E-WT could produce ADE against DENV.

Serum (obtained from mice immunized with recombinant adenovirus vaccine in Example 1) was gradiently diluted with RPMI-1640 medium (Invitrogen, C11875500BT) containing 1% FBS. The diluted samples were added to a 96-well plate, 10 μl per well. Then, the corresponding DENV (DENV2, GenBank: KM204118.1; DENV3, GenBank: KF824903; DENV4, GenBank: AF289029; DENV1 was a virus strain that isolated from a sample of an infected patient in Shenzhen Third People's Hospital) was added to each well and incubated in a 37° C. cell incubator for 1 hour.

The cultured K562 cells expressing FcγRIIA receptors on the cell surface were centrifuged at 800 g for 5 minutes, resuspended in RPMI-1640 medium containing 1% FBS, and then counted. After that, the cell density was adjusted to $3 \times 10^6$ cells per ml, added to the mixture comprising virus and serum in 10 μl per well, and incubated in a 37° C. cell incubator for 2 hours. 100 μl of RPMI-1640 medium containing 2% FBS was supplemented to each well, and the incubation was continued in a 37° C. cell incubator for 4 days. After 4 days, the cells were transferred to a 96-well plate, and centrifuged at 800 g for 5 minutes. The supernatant was removed. The precipitate was washed once with PBS, and the cells were collected by centrifugation. 100 μl of Fixation and Permeabilization solution (BD, 554722) was added to each well of the 96-well plate, and placed in a refrigerator at 4° C. for 20 minutes. Then, the cells were harvested by centrifugation at 800 g for 5 minutes and washed twice with 1×Perm/Wash buffer (BD, 554723). 50 μl of FITC-labeled Z6 antibody (Z6-FITC) was added to each well, and placed in a refrigerator at 4° C. for 1 hour. The cells were harvested by centrifugation and washed twice with 1×Perm/Wash buffer. The cells were resuspended in PBS (200 μl per well). The proportion of virus-infected positive cells was detected by flow cytometry.

Figure 2:
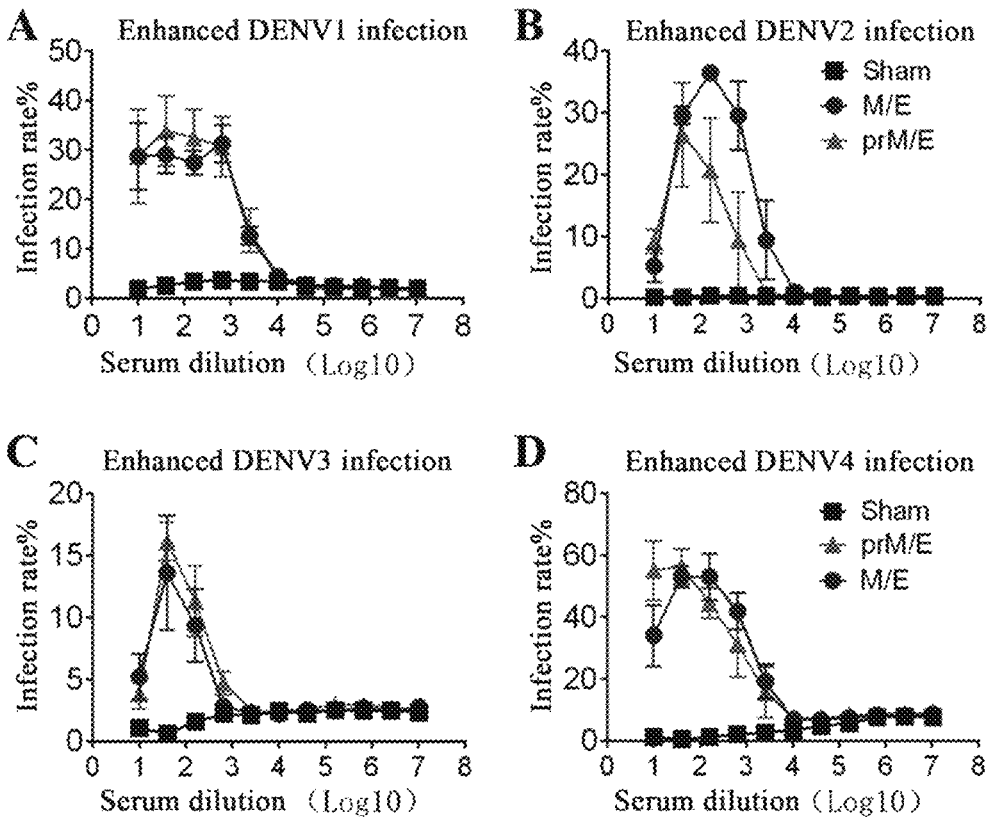
FIG. 2 shows the experimental result of enhancing DENV-infected cells by immunizing mouse serum with wild-type recombinant adenovirus vaccines AdC7-M/E-WT and AdC7-prM/E-WT.

The results were shown in FIG. 2, K562 cell expressing the FcγRIIA receptor on the cell surface were used as a cell infection model in the experiment. Serums from mice immunized with recombinant adenovirus vaccines in group of AdC7-M/E-WT (indicated by M/E in the figure) and in group of AdC7-prM/E-WT (indicated by prM/E in the figure) showed enhanced effects on DENV-infected K562 cells, and the serum of the control group Sham group (indicated by Sham in the figure) had no ADE. It was speculated that the serums from mice immunized with recombinant adenovirus vaccines AdC7-M/E-WT and AdC7-prM/E-WT have cross-reaction with ZIKV and DENV. Some of the antibodies in the serum can bind to DENV, thereby inducing ADE response.

Example 3 In Vitro Experiments to Detect the ADE of Monoclonal Antibodies Against DENV1-4

Z6 antibody is a monoclonal antibody binding to ZIKV E protein which was obtained from B cells isolated from the blood of a patient with ZIKV infection by sequencing the antibody sequence, recombinant expressing and purifying. Previous experiments have shown that it mainly bound to the FL epitope of ZIKV E protein (Wang, Qihui, et al. Science translational medicine 8.369(2016):369ra179.). Since the FL sequences of ZIKV and DENV were very conservative and Z6 antibody had low neutralizing activity (Wang, Qihui, et al. Science translational medicine 8.369 (2016):369ra179.), it was speculated that the Z6 antibody was likely to cause ADE to DENV, while the use of recombinant chimpanzee adenovirus vaccines AdC7-M/E-WT and AdC7-prM/E-WT constructed with ZIKV wild-type M/E and prM/E antigens were very likely to activate the production of antibodies targeting the FL epitope, thereby leading to ADE.

Figure 3:
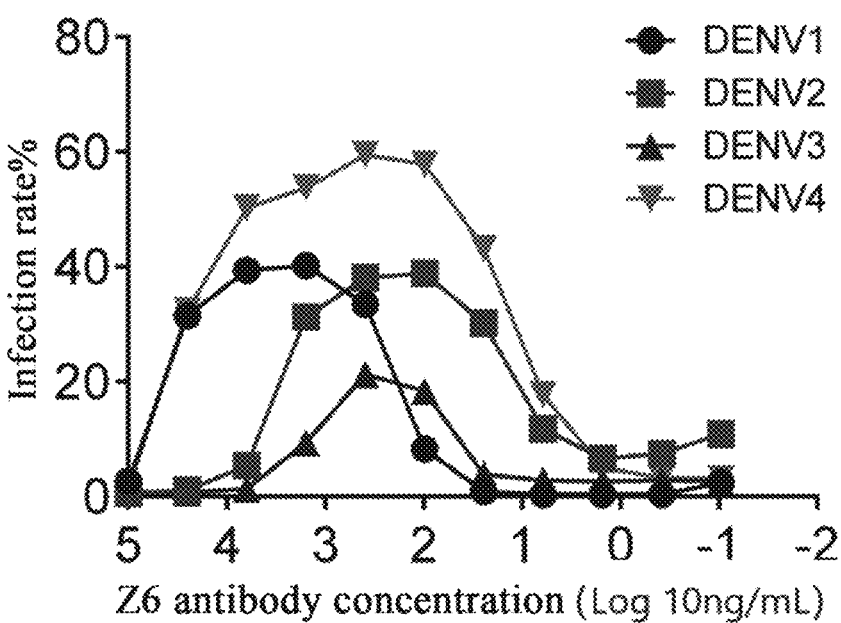
FIG. 3 shows that Z6 antibody has a certain degree of ADE on the cells of four serotypes infected with DENV.

It was tested whether the Z6 antibody will produce an ADE effect to DENV. The results were shown in FIG. 3. The results in FIG. 3 show that the Z6 antibody had a certain degree of ADE against the four serotypes of DENV. The Z6 antibody with lower neutralizing activity cross-reacted with DENV. Presumably, it was likely to cause ADE by binding to the FL epitope of DENV E protein, which will be further studied.

Example 4 Analysis of the Complex Structure of ZIKV E Protein and Z6 Antibody

Literatures had reported two complex structures of antibodies and antigens of the FL epitope of genus *Flavivirus*, namely the structure of 2A10G6 antibody and ZIKV soluble E protein (sE) (Dai, Lianpan, et al. Cell Host & Microbe (2016): S1931312816301494.), and the structure of E53 antibody and WNV E protein (Cherier, Mickael V, et al. The EMBO Journal 28.20 (2009): 3269-3276.). 2A10G6 was a *Flavivirus* broad-spectrum neutralizing antibody that can neutralize DENV1-4, WNV, YFV and ZIKV, which bound to the FL and be loop of ZIKV E protein (Dai, Lianpan, et al. Cell Host & Microbe (2016): S1931 312 816 301 494.).

In order to further analyze the antibody binding mechanism of ZIKV FL epitope, we obtained the complex structure of the Fab fragment of Z6 antibody and ZIKV E protein with a resolution of 3 A by combining data analysis with protein crystallization and X-ray diffraction methods. The results were shown in FIG. 4. The data collection and optimized parameters of the complex structures were shown in Table 1.

Figure 4:
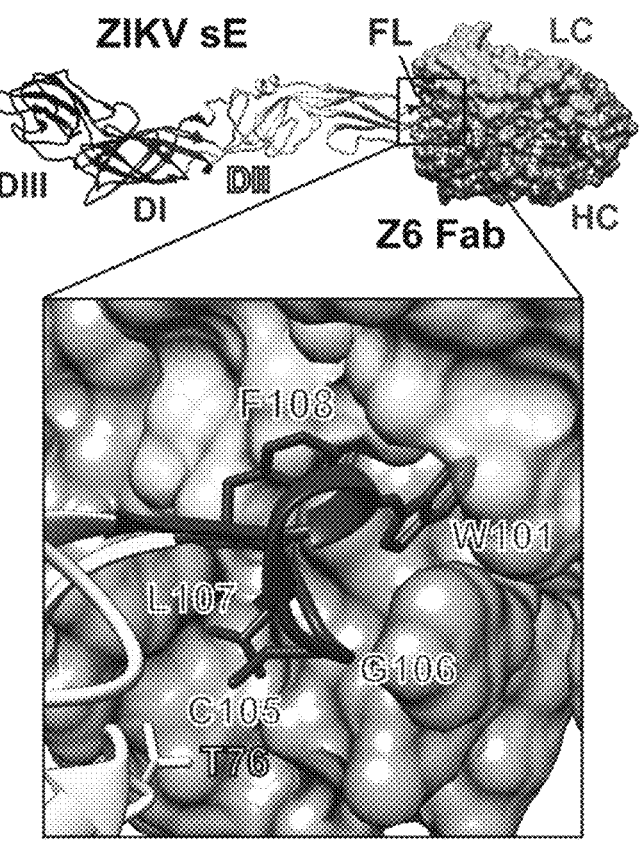
FIG. 4 shows the structure of a complex comprising Fab fragment of Z6 antibody and ZIKV E protein.

It can be seen from FIG. 4 that, similar to the 2A10G6 antibody, the Z6 antibody bound to the top of DII of the E protein at an almost vertical angle, and interacted with the FL and be loop of the E protein. However, the difference was that both the heavy and light chains of Z6 interact with the ZIKV E protein, while 2A10G6 focused more on the binding of the heavy chain. The results were shown in FIG. 5. By analyzing the binding amino acid sites, as the results shown in FIG. 6, it was found that the Z6 antibody had more interactions with W101, G106, L107 and F108 of ZIKV E protein. These four amino acid sites also play a key role in binding 2A10G6 antibody. Although the interaction between E53 and E protein was independent of W101, it also has relatively more contacts with G106 and L107.

Therefore, it was predicted that the modification of an immunogen at these 4 amino acid sites can avoid the production of the FL epitope-induced antibody, thereby reducing or eliminating the ADE on DENV.

It had been reported that ZIKV vaccine based on M/E antigen had a good protective effect (Abbink, Peter, et al. Science Translational Medicine 9.420 (2017).). Therefore, we choose M/E antigen for subsequent mutation design.

In addition, it had been reported in the literature that the ZIKV vaccine based on prM/E antigen also had a good protective effect (Dowd et al, Science, 2016, Vol 354, Issue 6309). Our previous data also proved that the mutation design based on M/E antigen had a similar effect with that based on the prM/E antigen. Thus, the experimental results of the mutation design based on the prM/E antigen in the examples of the present disclosure will not be repeated herein. The mutation design for the M/E antigen in the examples of the present disclosure is also applicable to the prM/E antigen.

TABLE 1

| Data collection and optimized parameters for ZIKV sE-Z6 complexes | |
| --- | --- |
| Parameter | ZIKV sE-Z6 |
| Data collection | |
| Space group | C2 |
| Wavelength (Å) | 0.97853 |
| Cell parameter | |
| a, b, c(Å) | 158.25, 153.67, 115.20 |
| α, β, γ(°) | 90.00, 125.49, 90.00 |
| Resolution (Å) | 50.00-3.00 (3.11-3.00) |
| Observed reflection | 238923 |
| Integrity (%) | 99.8 (100.0) |
| Redundancy | 11.7 (11.2) |
| Rpim (%) | 9.4 (59.6) |
| I/σ | 7.8 (1.0) |
| Refinement | |
| Rwork/Rfree(%) | 24.56/27.03 |
| No. atoms | |
| Protein | 12474 |
| Ligand | 0 |
| Water | 0 |
| B-factor | |
| Protein | 80.68 |
| Ligand | |
| Water | |
| r.m.s. deviation | |
| Bond length (Å) | 0.004 |
| Bond angle(°) | 1.038 |
| Ramachandran plot | |
| Favoured(%) | 97.97 |
| Allowed(%) | 2.03 |
| Outliers(%) | 0 |

Values in the parentheses indicate the highest resolution of the shell

Figure 7:
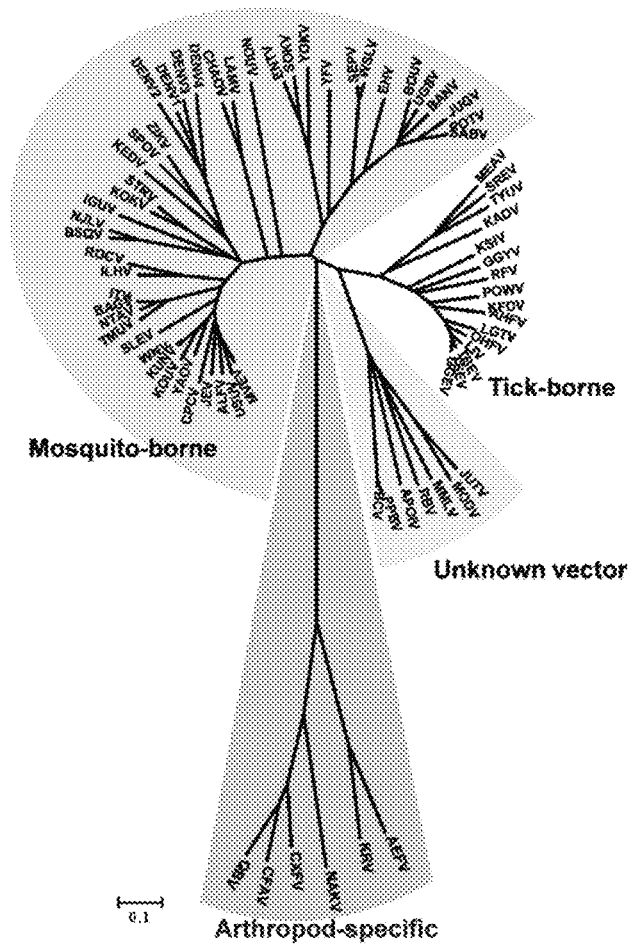
FIG. 7 shows a phylogenetic tree of genus *Flavivirus*.

Example 5 Construction of Chimeric Virus Antigen Protein Using the FL of a Virus of Genus *Flavivirus* with a Large Evolutionary Distance By aligning the amino acid sequences of the E protein FL epitope of viruses of genus *Flavivirus*, we found that the FL sequences of most viruses were conservative. However, there were still some viral FL sequences with large evolutionary distances, which differ from ZIKV FL sequences. In order to disrupt the ZIKV FL epitope without affecting normal protein folding and display of other neutralizing epitopes, we used the amino acid sequence of the FL of a virus that is evolutionarily distant from ZIKV in the genus *Flavivirus* (the *Flavivirus* phylogenetic tree as shown in FIG. 7) to construct a chimeric virus antigen protein. It was speculated that it can better maintain the overall conformation of the antigen and reduce the impact on epitopes other than the mutation site.

Figure 8:
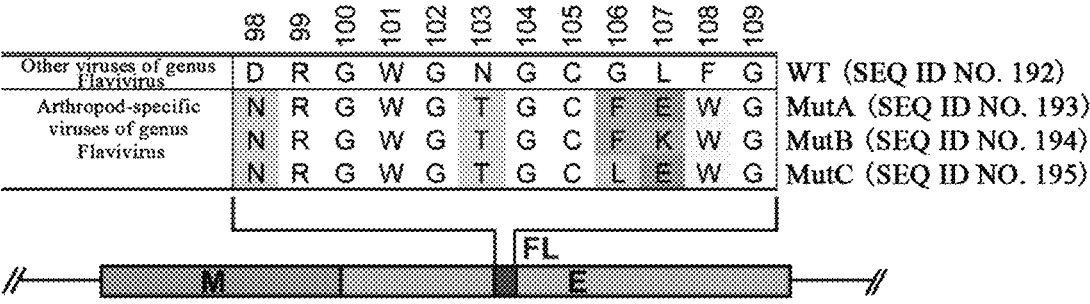
FIG. 8 shows the mutation sites and sequences of ZIKV M/E MutA/B/C mutants.

We designed mutants of ZIKV M/E antigens with the E protein FL sequences of these viruses as a reference. M and E were full-length, and the mutated site and sequence of the FL fusion region were shown in FIG. 8, in which MutA was derived from AEFV (*Aedes* flavivirus, GenBank: KC181923.1), and the mutation sites were D98N, N103T, G106F, L107E and F108W;

MutB was derived from CFAV (Cell fusing agent virus, GenBank: NC_001564.2), and the mutation sites were D98N, N103T, G106F, L107K and F108W;

MutC was derived from NAKV (Nakiwogo virus, GenBank: NC_030400.1), and the mutation sites were D98N, N103T, G106L, L107E and F108W.

The primers used in the construction of the pCAGGS-M/E-MutA/B/C plasmids were shown in Table 2. Taking the construction of MutA as an example, the plasmid pCAGGS-M/E-WT was used as a template, and WT-F and mutA-R were used as primers to obtain the product mutA-1 by PCR. Plasmid pCAGGS-M/E-WT was used as a template, and WT-R and mutA-F were used as primers, to obtain the product mutA-2 by PCR. Then, mutA-1 and mutA-2 were mixed in a molar ratio of 1:1 as a template, and WT-F and WT-R were used as primers for PCR to obtain the PCR product mutA. The pCAGGS plasmid was restricted with XhoI and EcoRI to obtain a linear plasmid with double cohesive ends. The digested linear plasmid and the PCR product mutA were mixed in a molar ratio of 1:5. The In-Fusion kit was used for recombination. The recombinant product was transformed into DH5a competent cells, which was spread on an ampicillin-resistant plate and cultured at 37° C. After that, the clones were picked for PCR identification and sequencing identification, and then the plasmid (pCAGGS-M/E-MutA) was extracted for subsequent experiments.

TABLE 2

| The primers used in the construction of pCAGGS-M/E-MutA/B/C | |
| --- | --- |
| Name of primer | Primer sequence (5'-3') |
| WT-F | TTTTGGCAAAGAATTCGCCG (SEQ ID NO. 2) |
| WT-R | GATCTGCTAGCTCGAGTCAAGCGCTCACAGCTGTGGACAGA (SEQ ID NO. 3) |
| mutA-R | GTGTAAGAGGACCCTGGTGAACAGGGGCTGGGGAACAGGCT GCTTCGAATGGGGA (SEQ ID NO. 4) |
| mutA-F | GTGAACAGGGGCTGGGGAACAGGCTGCTTCGAATGGGGAAA GGGCTCCCTGGTG (SEQ ID NO. 5) |
| mutB-R | GTGTAAGAGGACCCTGGTGAACAGGGGCTGGGGAACAGGCT GCTTCAAGTGGGGA (SEQ ID NO. 6) |

TABLE 2-continued

The primers used in the construction of pCAGGS-
M/E-MutA/B/C

| Name of primer | Primer sequence (5'-3') |
| --- | --- |
| mutB-F | GTGAACAGGGGCTGGGGAACAGGCTGCTTCAAGTGGGGAAA GGGCTCCCTGGTG (SEQ ID NO. 7) |
| mutC-R | GTGTAAGAGGACCCTGGTGAACAGGGGCTGGGGAACAGGCT GCCTGGAATGGGGA (SEQ ID NO. 8) |
| mutC-F | GTGAACAGGGGCTGGGGAACAGGCTGCCTGGAATGGGGAAA GGGCTCCCTGGTG (SEQ ID NO. 9) |

Example 6 Detection of M/E-MutA/B/C Antigen Activity 293T cells were transfected with wild-type plasmid pCAGGS-M/E-WT and mutant plasmids pCAGGS-M/E-MutA, pCAGGS-M/E-MutB and pCAGGS-M/E-MutC, respectively. After 48 hours, cells were collected, digested into single cells, fixed and permeabilized, incubated with ZIKV E-binding antibody, incubated with Goat Anti-Human FITC secondary antibody, and finally detected the positive proportion of samples by flow cytometry. The results were shown in FIG. 9.

Z3L1, Z20 and Z23 were ZIKV-specific antibodies with high neutralizing activity, which bind to DI, DII and DIII of ZIKV E protein, respectively (Wang, Qihui, et al. (2016) Science translational medicine 8.369:369 ra179.).

Figure 9:
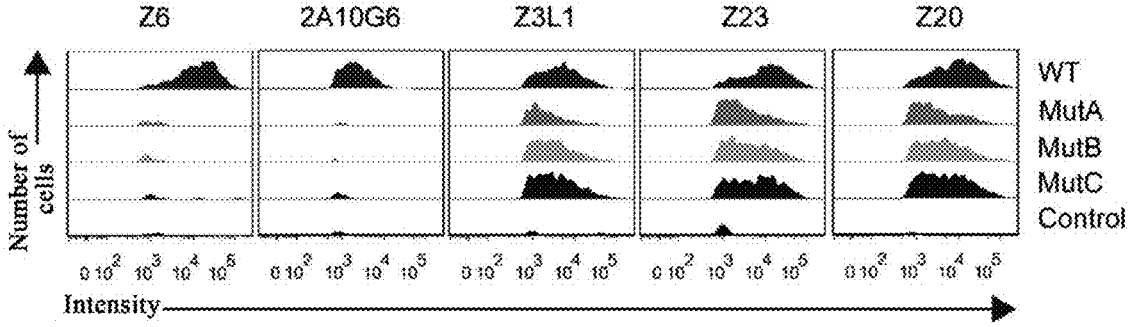
FIG. 9 shows the results of M/E-MutA/B/C antigen activity detected by flow cytometry.

As can be seen from FIG. 9, the antibodies (Z6 and 2A10G6) that bind to the FL epitope of the ZIKV E protein can bind to cells expressing the wild-type M/E-WT antigen, but none of them bound to cells expressing the 3 mutant antigens. The Z3L1, Z23 and Z20 antibodies with high neutralizing activity that bound to non-FL epitopes bind both to cells expressing the wild-type M/E-WT antigen and to cells expressing the 3 mutant antigens, indicating that the FL epitopes on M/E-MutA, M/E-MutB and M/E-MutC antigens were destructed, so that it was impossible for the corresponding antibodies to bind. However, the epitopes bound by other strong ZIKV neutralizing antibodies did not change, and the corresponding antibodies were still able to bind.

That is, M/E-MutA, M/E-MutB and M/E-MutC antigens can induce less or no antibodies that bind to DENV FL, thereby reducing ADE on DENV At the same time, M/E-MutA, M/E-MutB and M/E-MutC antigens do not affect other antibody epitopes.

Example 7 Construction of Recombinant Chimpanzee Adenovirus Vaccines AdC7-M/E-MutB and AdC7-M/E-MutC Using M/E-MutB and M/E-MutC Antigens of ZIKV It can be seen from FIG. 9 that the intensity of the positive cells of MutB and MutC was slightly higher than that of MutA. Therefore, the subsequent experiments were mainly carried out with MutB and MutC.

Figure 10:
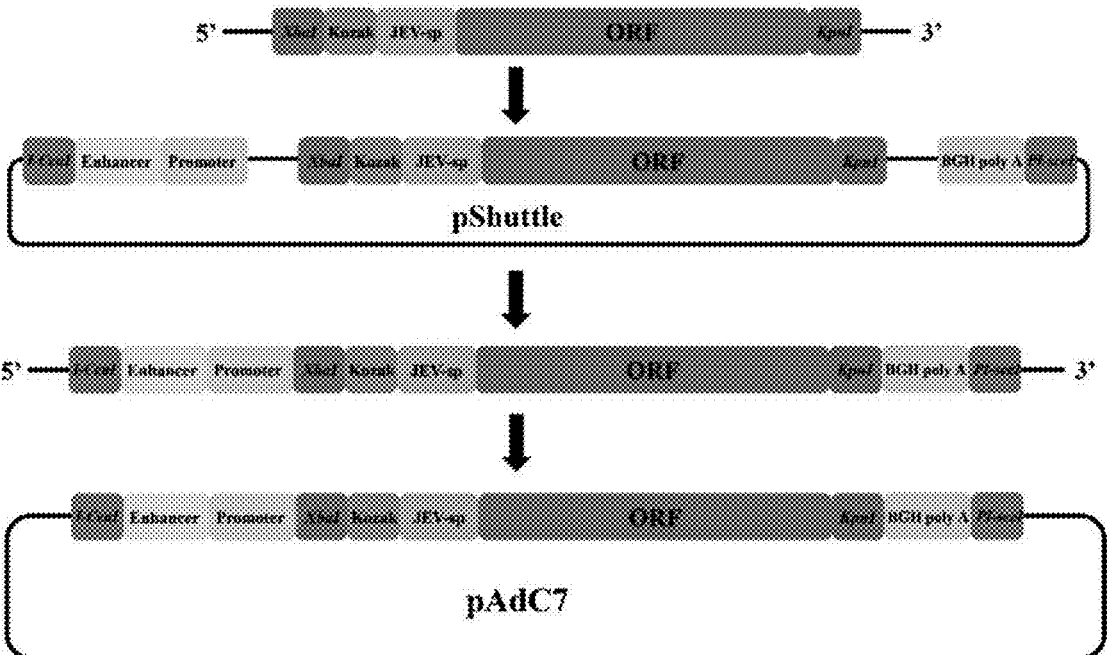
FIG. 10 shows the construction process of pAdC7-M/E-MutB/MutC recombinant plasmid.

First, the M/E-MutB and M/E-MutC antigens were cloned into the pshuttle vector. Plasmid pCAGGS-M/E-MutB or pCAGGS-M/E-MutC was used as template, and to_pshuttle-F and to_pshuttle-R were used as primers to carry out PCR reaction to obtain PCR product to_pshuttle-mutB and PCR product to_pshuttle-mutC. The pshuttle plasmid was restricted with XbaI (Thermo, FD0684) and KpnI (Thermo, FD0524) to obtain a linear plasmid with double cohesive ends. The digested linear plasmid was mixed with the PCR product to_pshuttle-mutB or to_pshuttle-mutC in a molar ratio of 1:5. The In-Fusion kit was used for recombination. The recombinant product was transformed into DH5a competent cells, spread on kanamycin-resistant plate, and cultured at 37° C. After that, the clones were picked for PCR identification and sequencing identification, and then the plasmid was extracted. Then the cassettes expressing M/E-MutB and M/E-MutC on pshuttle plasmids were constructed into AdC7 vector. For the above construction steps, see: Xu, Kun et al. (2018) Journal of virology. vol. 92, 6 e01722-17. 26 February The PCR products to_AdC7-MutB and to_AdC7-MutC were obtained by PCR reaction with plasmid pshuttle-M/E-MutB or MutC as template and to_AdC7-F and to_AdC7-R as primers. The AdC7 plasmid was restricted with PI-SceI (NEB, R0696S) and I-CeuI (NEB, R0699S) to obtain a linear plasmid with double cohesive ends. The digested linear plasmid was mixed with the PCR product to_AdC7-MutB or to_AdC7-MutC in a molar ratio of 1:5. The In-Fusion kit was used for recombination. The recombinant product was transformed into stbl2 competent cells, spread on ampicillin-resistant cells, and cultured at 30° C. After that, the clones were picked for PCR identification and sequencing identification, and then the plasmid was extracted. The construction flow of the recombinant plasmid was shown in FIG. 10. The primer sequences used were shown in Table 3.

TABLE 3

Primers for construction of chimpanzee adenovirus
ZIKV mutant vaccine with MutB and MutC antigens

| Name of primer | Primer sequence (5'-3') |
| --- | --- |
| to_ pshuttle-F | AAACGGGCCCTCTAGAGCCACCATGGGCAAGAGGAGC (SEQ ID NO. 10) |
| to_ pshuttle-R | TTTAACTTAAGCTTGGTACCTCAAGCGCTCACAGCTG TGG (SEQ ID NO. 11) |
| to AdC7-F | GTATAACTATAACGGTCCTAAGGTAGCGAA (SEQ ID NO. 12) |
| to AdC7-R | TCATTACCTCTTTCTCCGCACCCGACATAG (SEQ ID NO. 13) |

The pAdC7-M/E-MutB and pAdC7-M/E-MutC plasmids were linearized with PacI (NEB, R0547S) restriction endonuclease, and then heated in a constant temperature bath at 65° C. for 20 min to inactivate the endonuclease. Plasmids were transfected into HEK293 cells using Fugene-6 Transfection Reagent (Promega, E2691), cultured in a 37° C. incubator for at least 7 days, and then checked by microscopy every day for the appearance of plaques. All cells and supernatant were collected as the first-generation recombinant adenovirus when plaque cells fell off. The culture can be scaled up in sequence according to the ratio of 1:10, until the culture reaches 40 plates of cells. All cells were collected, and the cells were lysed by freezing and thawing 3 times to release the virus. After that, cesium chloride was used for density gradient centrifugation. Polyacrylamide gel (Bio-Gel P-6 DG Media, BIO-RAD, 1500738) was used for desalting and purification. OD260 of the sample was detected by NANODROP. The concentration of the sample was the value of OD260 multiplied by $1.1 \times 10^{12}$, with the unit being vp (viral particle)/ml. Aliquots were stored in $-80°$ C.

Example 8 Evaluation of Humoral Immune Response in BALB/c Mice Induced by Recombinant Adenovirus Vaccines AdC7-M/E-MutB and AdC7-M/E-MutC 24 BALB/c mice were randomly divided into 4 groups and immunized by intramuscular injection with 3 recombinant adenovirus vaccines, namely AdC7-M/E-WT, AdC7-M/E-MutB and AdC7-M/E-MutC. The dose of adenovirus vaccine immunization was $1.6 \times 10^{11}$ vp. 1 group of mice was immunized with PBS as a negative control. After 4 weeks, blood was collected to separate serum, and the neutralizing antibody titer in serum was detected by microneutralization assay.

Figure 11:
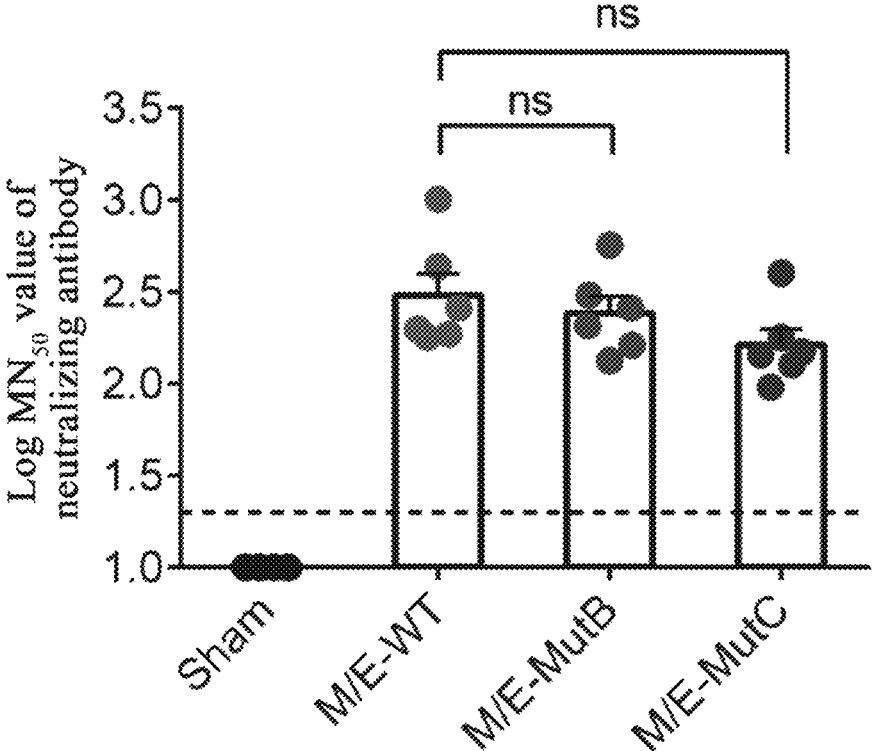
FIG. 11 shows the neutralizing antibody titers of BALB/c mice serum after immunization with ZIKV recombinant adenovirus vaccine.

The results were shown in FIG. 11. Both wild-type AdC7-M/E-WT and mutant adenovirus vaccines AdC7-M/E-MutB and AdC7-M/E-MutC can induce neutralizing antibodies in mice. Log($MN_{50}$) values ranged from 2.0 to 2.5, and there was no significant difference in neutralizing antibody titers between the AdC7-M/E-MutB and AdC7-M/E-MutC groups and the AdC7-M/E-WT group, indicating that the mutation did not significantly reduce the immunogenicity of the antigen, which could still activate the production of neutralizing antibodies. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

Example 9 Evaluation of Humoral Immune Response in Ifnar1$^{-/-}$ Mice Induced by AdC7-M/E-MutB and AdC7-M/E-MutC Vaccines Since ZIKV infection in BALB/c mice did not cause mouse death and obvious disease symptoms, in order to better verify the effect of the vaccine, we selected the immunodeficient Ifnar1$^{-/-}$ mouse as the infection model of ZIKV (Lazear, Helen M et al. (2016), vol. 19,5: 720-30.). Humoral immune responses in Ifnar1$^{-/-}$ mice induced by AdC7-M/E-MutB and AdC7-M/E-MutC Vaccines were evaluated.

Ifnar1$^{-/-}$ mice were randomly divided into 4 groups and respectively injected with AdC7-M/E-WT, AdC7-M/E-MutB and AdC7-M/E-MutC adenovirus vaccines by intramuscular injection. The dose for immunization with the adenovirus vaccine was $1.6 \times 10^{11}$ vp, and 1 group of mice was immunized with PBS as a negative control. After 28 days, blood was collected to separate serum, and the titer level of neutralizing ZIKV antibody in the serum of Ifnar1$^{-/-}$ mice was detected by microneutralization assay. The results were shown in FIG. 12.

Figure 12:
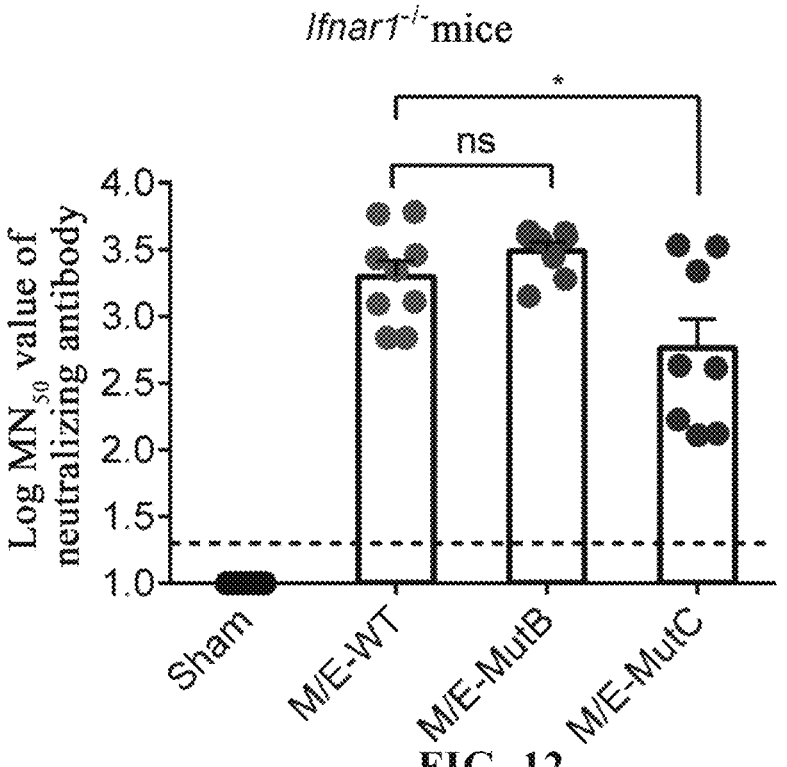
FIG. 12 shows the neutralizing antibody titers of Ifnar1$^{-/-}$ mice serum after immunization with ZIKV recombinant adenovirus vaccine.

As can be seen from FIG. 12, both AdC7-M/E-MutB and AdC7-M/E-MutC vaccines can induce higher levels of neutralizing antibody differences in mice. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

Example 10 Challenge Protection Experiment after Immunization of Ifnar1$^{-/-}$ Mice The Ifnar1$^{-/-}$ mice immunized in Example 9 were challenged with ZIKV virus on Day 30 after immunization, by intraperitoneally injecting and $5 \times 10^6$ PFU ZIKV (SMGC-1 strain). The results were shown in FIG. 13.

Figure 13:
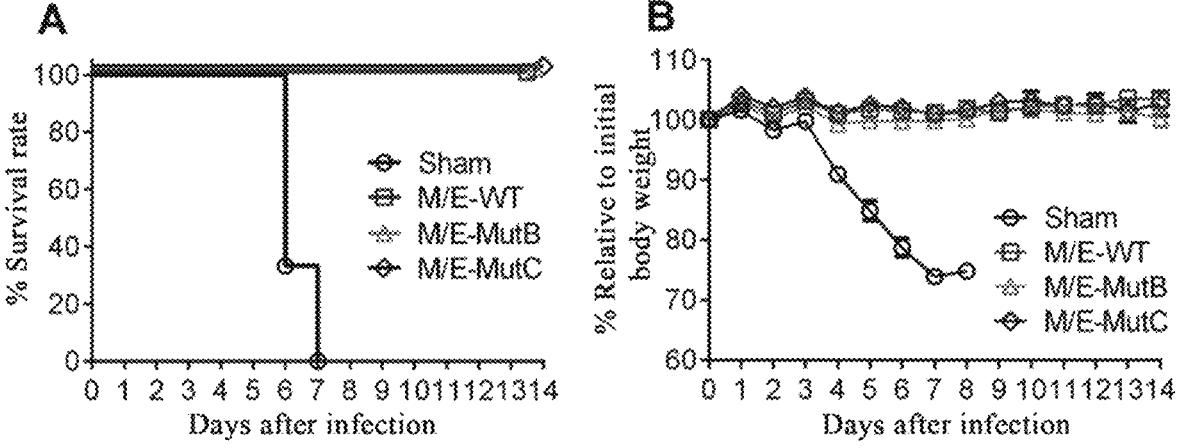
FIG. 13 shows the results of mortality rate and body weight changes in Ifnar1$^{-/-}$ mice immunized with ZIKV recombinant adenovirus vaccine after challenge assay.

It can be seen from FIG. 13 that the body weight of the sham group gradually decreased on Day 4 after the challenge (Panel B in FIG. 13), and all the mice in the sham group died on Day 6 and Day 7 (Panel A in FIG. 13). However, mice immunized with AdC7-M/E-WT, AdC7-M/E-MutB and AdC7-M/E-MutC did not suffer a weight loss after challenge (Panel B in FIG. 13). None of the three groups of mice died (Panel A in FIG. 13). It was indicated that the AdC7-M/E-MutB and AdC7-M/E-MutC vaccines could exhibit a complete protective effect during mice challenge, which was the same as the wild-type AdC7-M/E-WT vaccine. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

To test whether AdC7-M/E-MutB and AdC7-M/E-MutC vaccines can protect mice against viremia induced by viral infection, in this experiment, the blood of mice on Day 3 and Day 6 after the challenge were collected to separated serum. After that, RNA was extracted using MagaBio Plus Viral RNA Kit (Bori Technology, BSC58S1B), and then FastKing One-Step Reverse Transcription-Fluorescence Quantitation Kit (Tiangen Biochemical Technology, FP314) was used for viral RNA Quantification. The probe and the primer sequences used in quantification were

TABLE 4

| Probe and primer sequences used for RT-PCR quantification of ZIKV-SMGC-1 nucleic acid | |
|---|---|
| Name | Sequence (5'-3') |
| ZIKV-probe | FAM - CCACACCTCTGCCGGCACAC - TAMRA (SEQ ID NO. 14) |
| ZIKV-F | TTGGCTGGCCTATCAGGTTG (SEQ ID NO. 15) |
| ZIKV-R | CACCTCGGTTTGAGCACTCT (SEQ ID NO. 16) |

Figure 14:
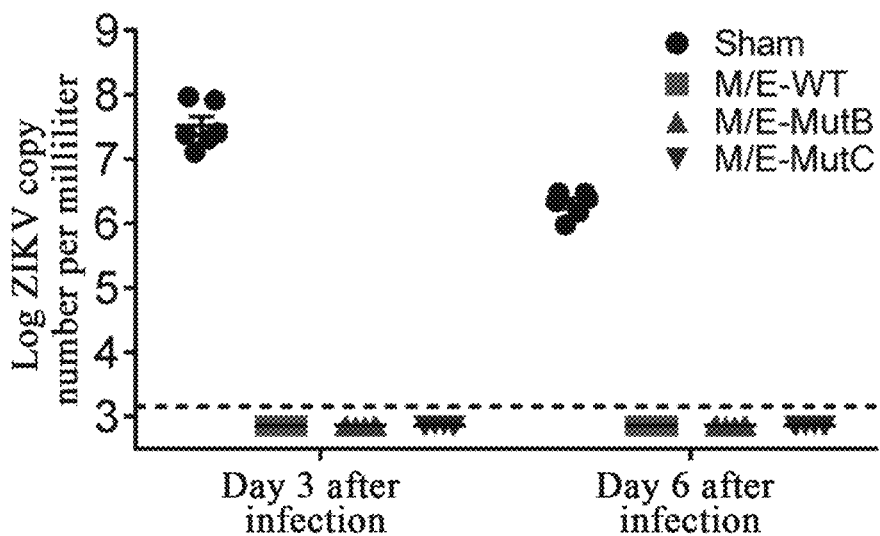
FIG. 14 shows the experimental result of ZIKV recombinant adenovirus vaccine protecting Ifnar1$^{-/-}$ mice against viremia caused by ZIKV infection.

It can be seen from FIG. 14 that higher viral loads can be detected in the mice in the Sham group on Day 3 and Day 6 after infection, while no virus was detectable in the serums from mice immunized with AdC7-M/E-WT, AdC7-M/E-MutB and AdC7-M/E-MutC adenovirus vaccine on Day 3 and Day 6 after infection, which indicated that AdC7-M/E-MutB and AdC7-M/E-MutC vaccines can protect mice against viremia comparable to that of wild-type AdC7-M/E-WT vaccine. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

Example 11 Detection of Sterilizing Immune Effect of ZIKV Vaccine

The above experiments demonstrated that immunization of mice with AdC7-M/E-MutB and AdC7-M/E-MutC vaccines could provide protection against viremia and death caused by ZIKV infection. Further experiments were designed to detect whether AdC7-M/E-MutB and AdC7-M/E-MutC vaccines could provide sterilizing immunity. The specific steps were as follows.

Ifnar1$^{-/-}$ mice were randomly divided into 4 groups and immunized by intramuscular injection with 3 recombinant adenovirus vaccines, namely AdC7-M/E-WT, AdC7-M/E-MutB and AdC7-M/E-MutC. The dose of adenovirus vaccine immunization was 1.6×10$^{11}$ vp. 1 group of mice was immunized with PBS as a negative control. On day 28 after immunization, blood was collected to separate serum. On the 30th day after immunization, 5×10$^4$ FFU of ZIKV (SMGC-1 strain) was intraperitoneally injected. Blood was collected again on day 6 after ZIKV was challenged. After that, parts of liver, spleen, testis, brain and spinal cord were dissected on the same day. The dissected tissues and organs were added to PBS solution, then ground with a grinder (Tiangen Biochemical Technology, OSE-Y30). The supernatant was removed by centrifugation. RNA was extracted using MagaBio Plus virus RNA kit, and then ZIKV RNA was detected by RT-PCR. The results were shown in FIG. 15.

Figure 15:
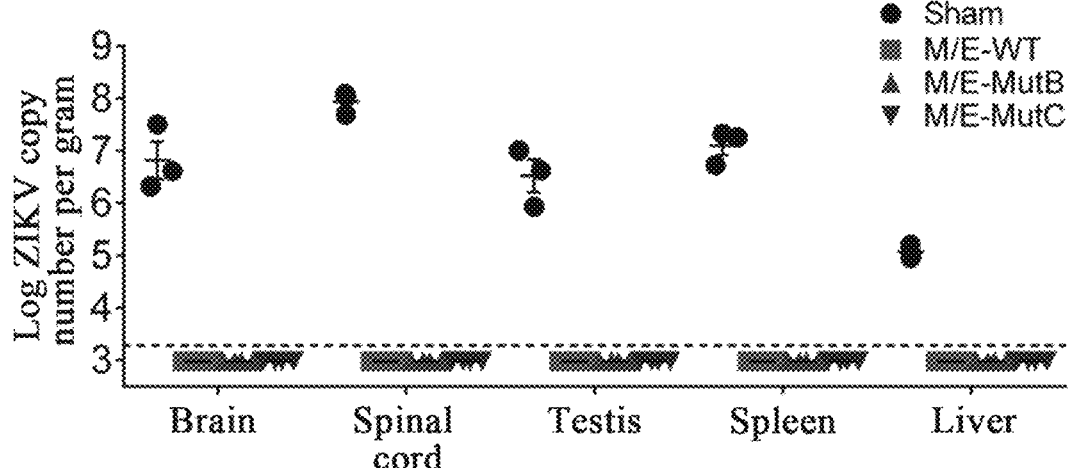
FIG. 15 shows the experimental result of ZIKV recombinant adenovirus vaccine protecting Ifnar1$^{-/-}$ mice against ZIKV-infected tissues and organs after challenge assay.

As can be seen from FIG. 15, a certain amount of virus was detected in the 5 organs of the mice in the Sham group, while no virus was detected in all tissues and organs of the 3 groups of mice immunized with AdC7-M/E-WT, AdC7-M/E-MutB and AdC7-M/E-MutC adenovirus vaccines. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

Serum neutralizing antibody titers were detected on day 28 after immunization and on day 7 after challenge using a microneutralization assay. The results were shown in FIG. 16.

Figure 16:
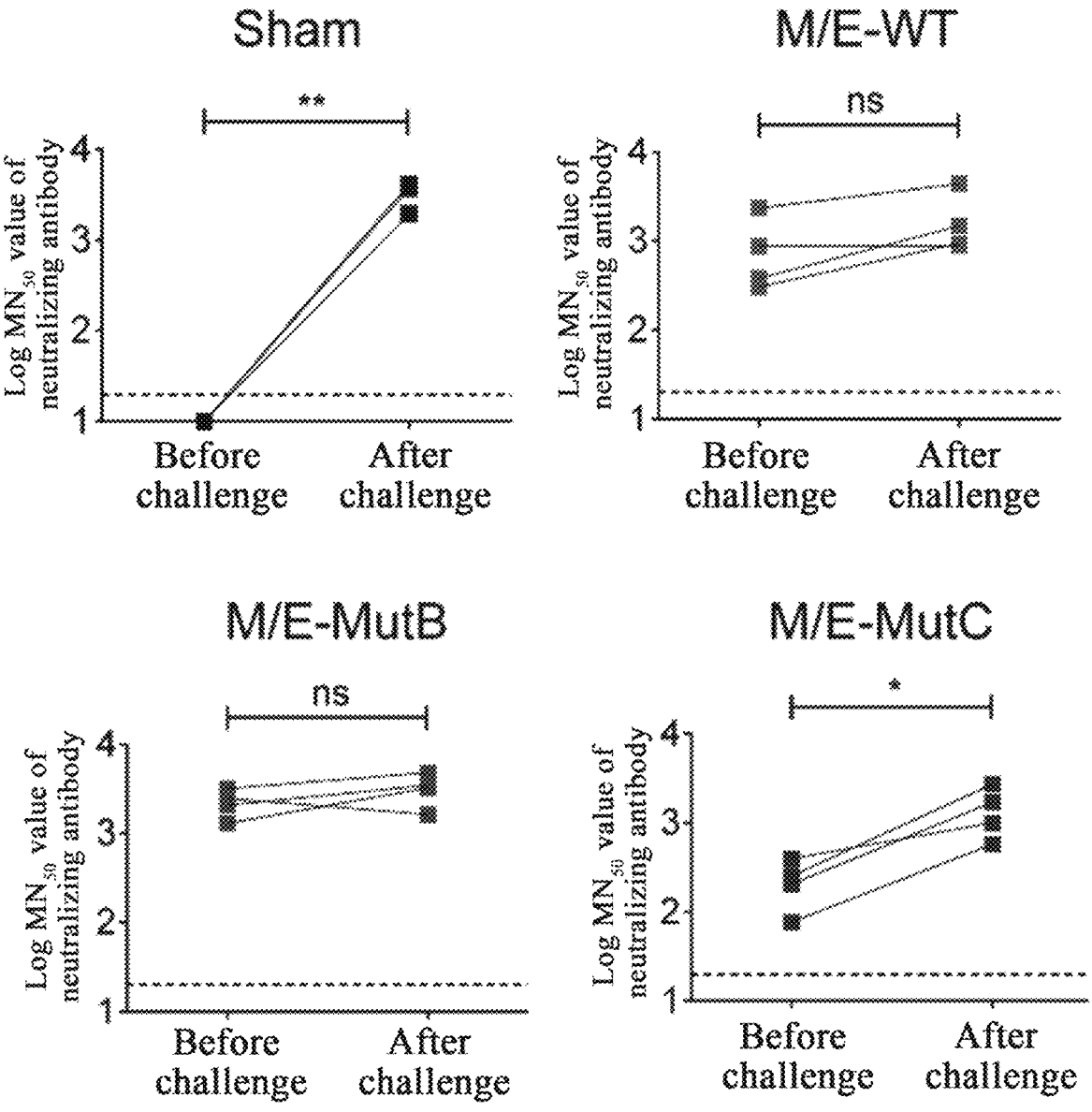
FIG. 16 shows the result of the change in neutralizing antibody titers of serum of Ifnar1$^{-/-}$ mice immunized with ZIKV recombinant adenovirus vaccine before and after the challenge assay.

As can be seen from FIG. 16, no neutralizing antibody could be detected in the Sham group before the challenge, and a relatively high titer of neutralizing antibody can be detected in each mouse in the Sham group on day 7 after the challenge. The two groups immunized with AdC7-M/E-WT and AdC7-M/E-MutB vaccines had no significant difference in serum neutralizing antibody titers before and after challenge, and maintained at almost the same level, indicating that AdC7-M/E-WT vaccine as well as AdC7-M/E-MutB, and AdC7-M/E-MutC vaccines can provide complete immunity to challenge virus, in which AdC7-M/E-MutB vaccine showing complete sterilizing immunity was slightly better than AdC7-M/E-MutC vaccine. Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group. FIG. 16 sequentially showed the results of the Sham group, the M/E-WT group, the M/E-MutB group, and the M/E-MutC group from left to right.

Example 12 Detection of Cross-Reaction to DENV in Serum of BALB/c Mice Immunized with ZIKV Vaccine One of the main reasons that ZIKV infection leads to ADE to DENV is that the FL epitope of the E protein of ZIKV and DENV is relatively conservative, so that some antibodies induced by ZIKV that cross-react with DENV (Stettler, K., et al. Science (2016): science.aaf8505.). Therefore, we further detected the cross-reaction between the serum of BALB/c mice immunized with AdC7-M/E-WT, AdC7-M/

E-MutB and AdC7-M/E-MutC adenovirus vaccines and the four serotypes of DENV by ELISA experiments. The result was shown in FIG. 17.

Figure 17:
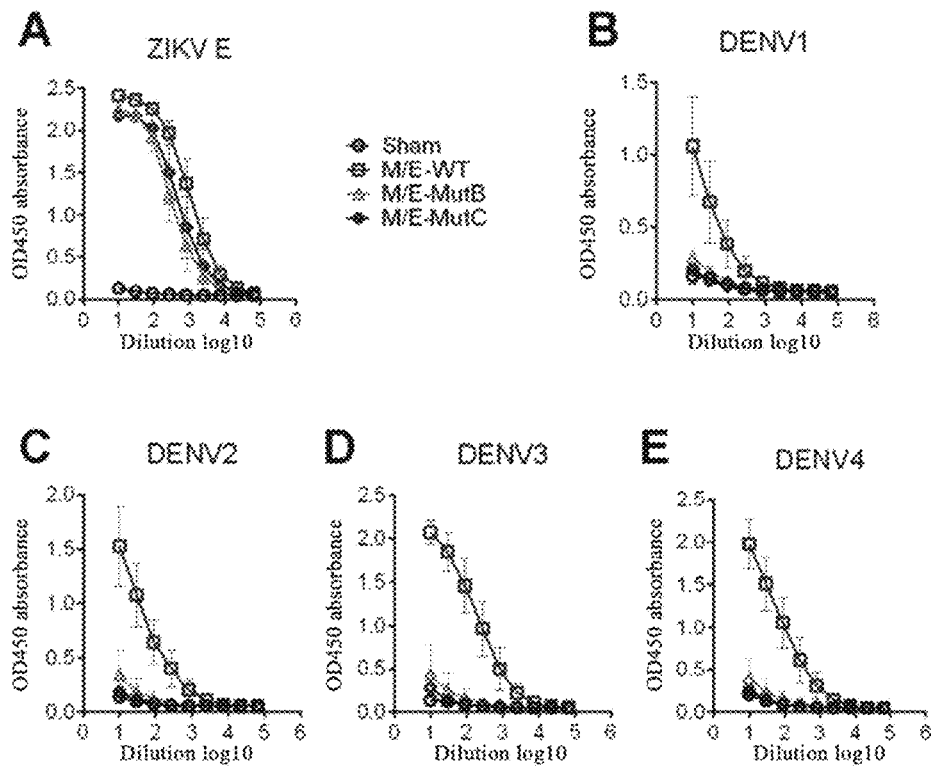
FIG. 17 shows the experiment result of cross-reaction of four serotypes of DENV by immunizing the serum of BALB/c mice with ZIKV recombinant adenovirus vaccine.

It can be seen from FIG. 17 that the serum of BALB/c mice immunized with AdC7-M/E-WT, AdC7-M/E-MutB and AdC7-M/E-MutC vaccine groups had strong binding ability to ZIKV E protein. However, their binding abilities to DENV E protein of four serotypes were different. The serums from mice in M/E-MutB group and M/E-MutC group had very low binding ability to DENV E protein of four serotypes, while the binding abilities of serums from mice in M/E-WT group to the four serotypes of DENV E protein remained at a high level. This indicated that the mutant disrupts the E protein FL epitope and reduced the amount of antibodies induced by this epitope, thus showing a weakened binding ability of the serums from mice immunized with AdC7-M/E-MutB and AdC7-M/E-MutC adenovirus vaccine to bind DENV E protein.

Among others, as shown in the figure, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group. Panel A in FIG. 17 showed the results of binding ability of mouse serum to Zika virus (ZIKV) E protein. Panel B showed the result of binding ability of mouse serum to serotype 1 dengue virus (DENV1) E protein. Panel C was the result of binding ability between mouse serum and serotype 2 dengue virus (DENV2) E protein. Panel D showed the result of binding ability between mouse serum and serotype 3 dengue virus (DENV3) E protein. Panel E showed the result of binding ability between mouse serum and serotype 4 dengue virus (DENV4) E protein.

Example 13 In Vitro Experiments to Detect the ADE to DENV of Serum from BALB/c Mice Immunized with ZIKV Vaccine The experimental results of Example 12 demonstrated that the AdC7-M/E-MutB and AdC7-M/E-MutC vaccines reduced the induction of cross-antibodies against DENV. We further designed experiments to demonstrate whether the AdC7-M/E-MutB and AdC7-M/E-MutC vaccines could reduce ADE to DENV The specific steps were as follows.

The serums of the immunized BALB/c mice in Example 8 were diluted in gradient, incubated with DENV1, DENV2, DENV3 and DENV4, respectively, and then K562 cells were added. After 4 days of culture, FITC-labeled Z6 antibody was used for staining, followed by flow cytometry to detect the proportion of positive cells. The results were shown in FIG. 18.

DENV virus could not infect K562 cells without antibody mediation. As can be seen from FIG. 18, since the serum of the Sham group did not contain antibodies that could bind to DENV, the infection rate of the detected samples was at the background level. The serums from the mice in the M/E-WT group could mediate four serotypes of DENV virus to infect K562 cells. The infection rates of both groups of the M/E-MutB and M/E-MutC samples were significantly lower than those of the M/E-WT group, showing a weakened or even eliminated ADE to DENV. This indicates that AdC7-M/E-MutB and AdC7-M/E-MutC vaccines achieved a good effect of reducing ADE.

Among others, as shown in the figure, Sham referred to the PBS-immunized group, M/E-WT referred to the AdC7-M/E-WT vaccine group, M/E-MutB referred to the AdC7-

M/E-MutB vaccine group, and M/E-MutC referred to the AdC7-M/E-MutC-immunized vaccine group.

Figure 18:
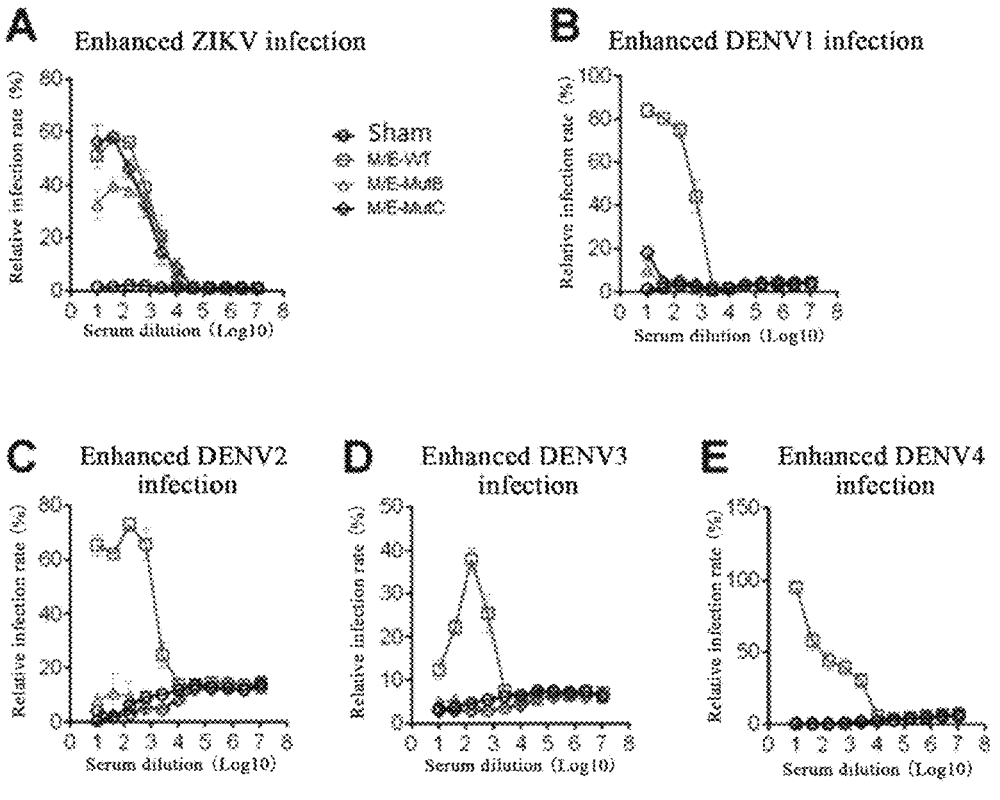
FIG. 18 shows the result of ADE experiment on cells infected with four serotypes of DENV by immunizing the serum of BALB/c mice with ZIKV recombinant adenovirus vaccine.

In FIG. 18, Panel A shows the detection of enhancement on ZIKV infection of K562 cells by mouse serum. Panel B shows the detection of enhancement on DENV1 infection of K562 cells by mouse serum. Panel C shows the detection of enhancement on DENV2 infection of K562 cells by mouse serum. Panel D shows the detection of enhancement on DENV3 infection of K562 cells by mouse serum. Panel E shows the detection of enhancement on DENV4 infection of K562 cells by mouse serum.

The above series of in vitro experiments had proved that AdC7-M/E-MutB and AdC7-M/E-MutC adenovirus vaccines could reduce or even eliminate the ADE to DENV after immunization.

Example 14 In Vivo Experiments to Detect the ADE to DENV in Serum from BALB/c Mice Immunized with ZIKV Vaccine To further demonstrate whether AdC7-M/E-MutB and AdC7-M/E-MutC vaccines can reduce ADE to DENV under physiological conditions, we used a model based on Ifn$\alpha$/$\beta$r$^{-/-}$Ifn$\gamma$r$^{-/-}$ mice to validate ADE effect on DENV First, 80 BALB/c mice were randomly divided into 4 groups of 20 mice each and immunized with AdC7-M/E-WT, AdC7-M/E-MutB and AdC7-M/E-MutC adenovirus vaccine and PBS, respectively. The dose of adenovirus vaccine immunization was 1.6×10$^{11}$ vp each mouse. Blood was collected after 4 weeks to separate serum, which was heated at 56° C. for 30 minutes, and the serums from 20 mice in each group were mixed together for subsequent passive immunization of Ifn$\alpha$/$\beta$r$^{-/-}$Ifn$\gamma$r$^{-/-}$ mice. Ifn$\alpha$/$\beta$r$^{-/-}$Ifn$\gamma$r$^{-/-}$ mice were randomly divided into 4 groups and intraperitoneally injected with serums from BALB/c mice immunized with AdC7-M/E-WT, AdC7-M/E-MutB and AdC7-M/E-MutC adenovirus vaccine or PBS, respectively (serums were diluted with PBS at a ratio of 1:10, and each mouse was injected with 200 µl of the diluted serum). DENV2 virus was injected subcutaneously at 5000 FFU per mouse 24 hours later, and each mouse was weighed before injection. After that, the status, survival and body weight of the mice were observed every day, and the results were shown in FIG. 19.

Figure 19:
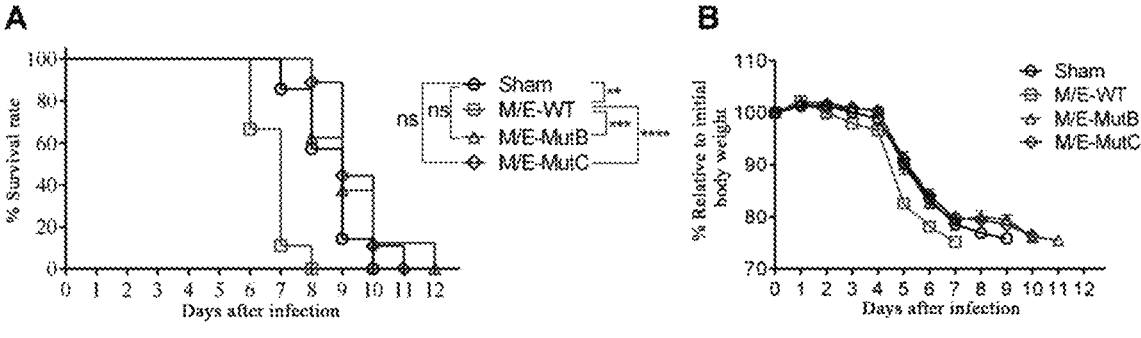
FIG. 19 shows the result of in vivo experiments to detect the effect of ZIKV recombinant adenovirus vaccine on the pathogenicity of infection-enhanced Ifnα/βr$^{-/-}$Ifnγr$^{-/-}$ mice.

As can be seen from FIG. 19, compared with the mice in the Sham group, the mice in the M/E-WT group died earlier, indicating that the serum of the mice immunized with the AdC7-M/E-WT vaccine enhanced the incidence of DENV Additionally, the time and trend of death of mice in the M/E-MutB and M/E-MutC groups were consistent with those in the Sham group (panel A in FIG. 19), indicating that mutations to the ZIKV E protein reduced the production of antibodies that led to ADE effect against DENV, such that the performance of mice in M/E-MutB and M/E-MutC groups were similar to that in the Sham group. The change trend of body weight also showed that the weight of the mice in the M/E-WT group decreased faster, while the change trend of the weight of the mice in the M/E-MutB and M/E-MutC groups was consistent with that of the Sham group (Panel B in FIG. 19). These in vivo results clearly demonstrated that AdC7-M/E-MutB and AdC7-M/E-MutC vaccines could significantly reduce ADE against DENV after immunization of wild-type vaccine.

Among others, as shown in FIG. 19, Sham referred to the PBS-immunized group, M/E-WT referred to the AdC7-M/E-WT vaccine group, M/E-MutB referred to the AdC7-M/E-MutB vaccine group, and M/E-MutC referred to the AdC7-M/E-MutC-immunized vaccine group.

Example 15 Profile Analysis of Antibodies Induced by ZIKV Vaccine in BALB/c Mice Since the FL-replaced ZIKV vaccine induced protective immunity while reducing the ADE response to DENV, we further analyzed the B-cell profile of ZIKV E in mice to explain how the mutated vaccine affected antibody responses.

Figure 20:
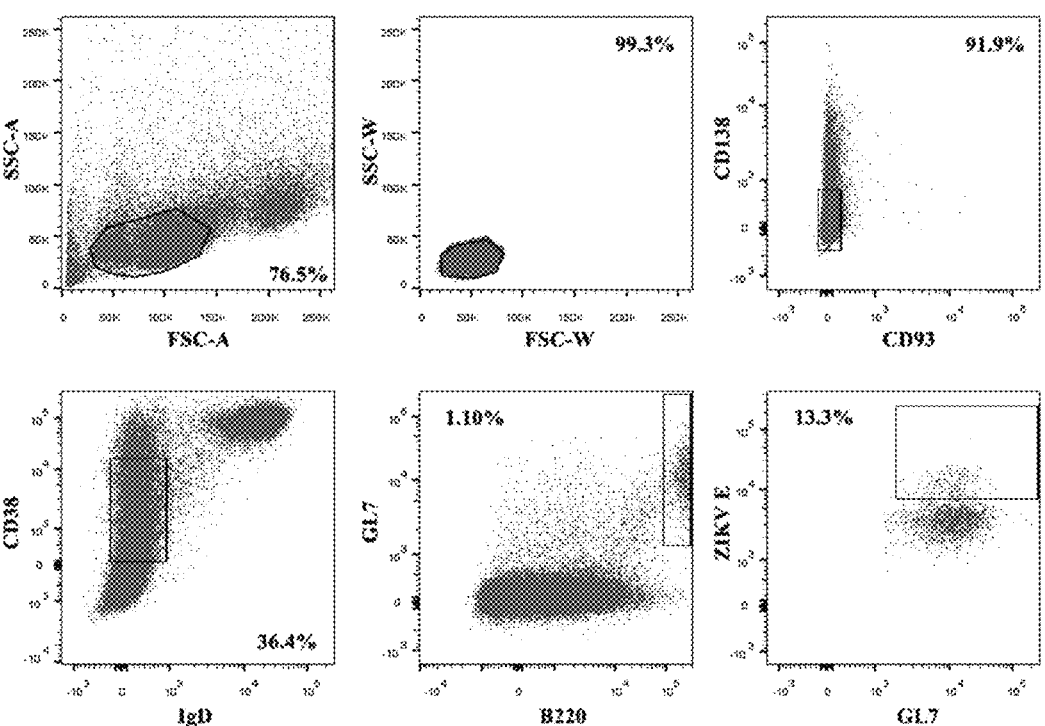
FIG. 20 shows the conditions for sorting GC B cells that bind to ZIKV E protein from 5 lymph node cells of BALB/c mice immunized with ZIKV recombinant adenovirus vaccine by flow cytometry.

BALB/c mice were randomly divided into 3 groups, and were immunized with AdC7-M/E-WT adenovirus vaccine (WT group), AdC7-M/E-MutB adenovirus vaccine (MutB group) and AdC7-M/E-MutC adenovirus vaccine (MutC group) by intramuscular injection, 1.6×10$^{11}$ vp per mouse. On day 20 after immunization, the lymph nodes were dissected out and placed in 1640 medium containing 1% FBS. The lymph nodes of all mice in each vaccine group were mixed together, ground using the rough side of a glass slide, and followed by filtration with a 0.45 m filter. Lymphocytes were centrifuged at 400 g for 15 minutes at 4° C., the supernatant was discarded and the precipitate was resuspended in 1 ml of FACS buffer. FACS buffer was a PBS solution comprising 0.5% FBS. After resuspension, it was transferred to a 1.5 ml EP tube, centrifuged at 400 g for 10 minutes at 4° C. The supernatant was discarded. The cells were resuspended in 200 µl FACS buffer. 4 g biotin-labeled mixture of ZIKV E monomeric protein and dimeric protein were added, and incubated at 4° C. for 30 min in the dark. Then, 1 ml of FACS buffer was added, mixed well, and centrifuged to precipitate cells. After that, 1 ml of FACS buffer was added to wash again, and then antibody was added for staining. The antibody was diluted with FACS buffer. Each 200 µl of antibody solution contained: FITC—GL7, 2 µl (BD, 553666); PE—CD138, 4 µl (BD, 553714); PE/CY7—CD38, 4 µl (BioLegend, 102718); APC—CD93, 4 µl (BioLegend, 136510); BV421—B220, 16 µl (BioLegend, 103240); BV510—IgD, 2 µl (BD, 563110); BV711, 4 µl (BD, 563262). 200 µl of antibody solution was added to each sample, which was incubated at 4° C. for 30 min in the dark, and then washed twice with FACS buffer. 2 ml of FCAS buffer was added. The cells were resuspended, filtered with a 0.45 m filter, and transferred to a flow tube. The sorting conditions were GL-7+ B220hi CD38lo IgD– CD93– CD138–+ (as shown in FIG. 20). GC B cells that reacted with ZIKV E were sorted, which were then used for library construction before sequencing.

We used single-cell sequencing technology to obtain single-cell paired B cell receptor (BCR) sequences. Chromium Single Cell V(D)J Enrichment Kit, Mouse B Cell, 96 rxns (10×genomics, PN-1000072) kit was used for library construction before sequencing. Then, high-throughput sequencing was performed to analyze the full-length sequence of the V(D)J fragment of light chain and heavy chain in each cell. The results were shown in FIG. 21 and Table 5.

Figure 21:
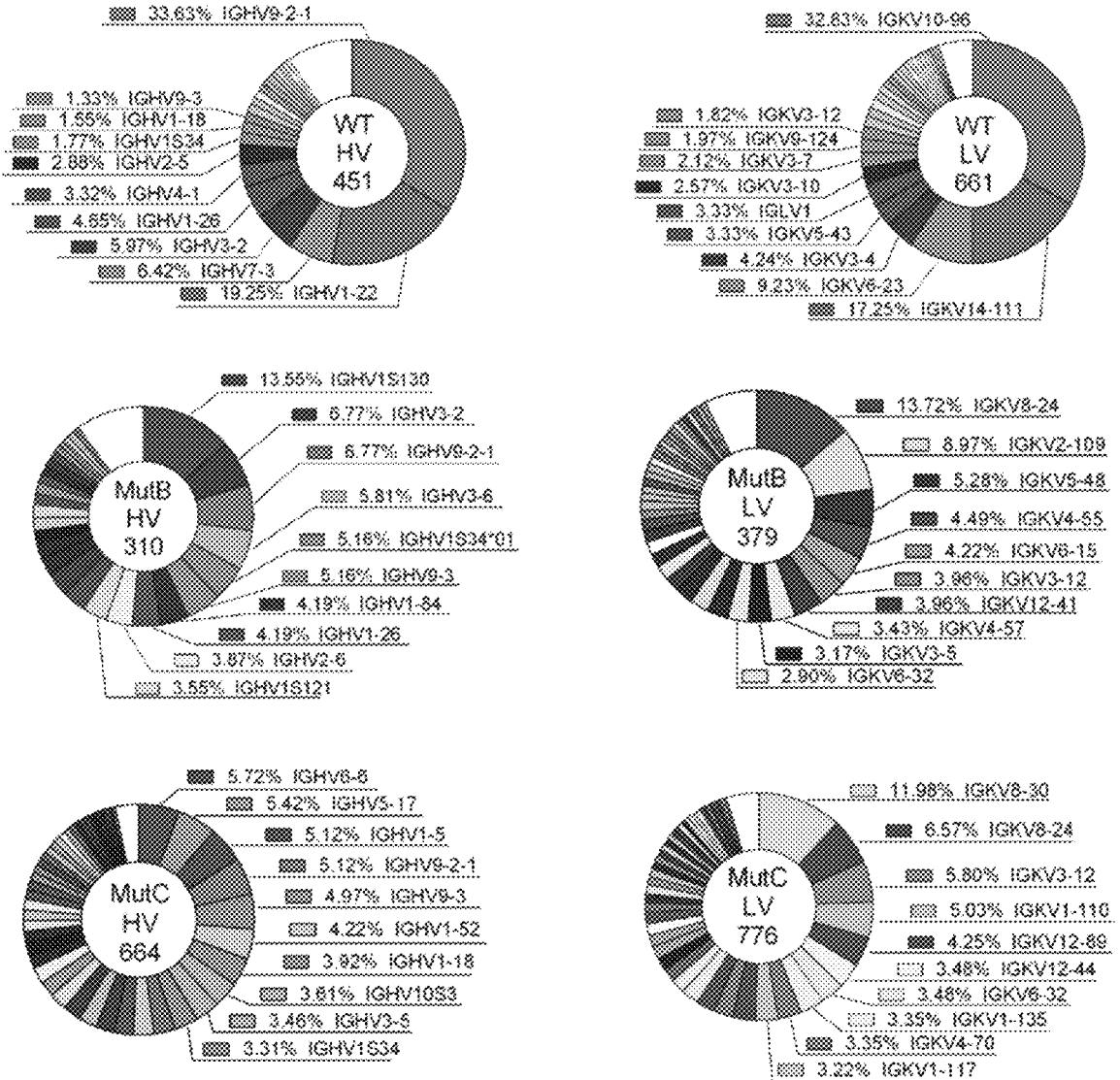
FIG. 21 shows the profiling result of GC B cell antibody binding to ZIKV E protein in BALB/c mice immunized with ZIKV recombinant adenovirus vaccine.

As can be seen from FIG. 21 and Table 5, 451 heavy chain variable region sequences and 661 light chain variable region sequences were obtained from the WT group samples, which could be matched to 334 pairs. 310 heavy chain variable region sequences and 379 light chain variable region sequences were obtained from the MutB group samples, which could be matched to 234 pairs. 664 heavy chain variable region sequences and 776 light chain variable region sequences were obtained from the MutC group samples, which could be matched to 515 pairs. Among others, in FIG. 21 and Table 5, WT referred to the group immunized with AdC7-M/E-WT vaccine, MutB referred to the group immunized with AdC7-M/E-MutB vaccine, and MutC referred to the group immunized with AdC7-M/E-MutC vaccine.

TABLE 5

| Summary of BCR sequencing data | | | |
|---|---|---|---|
| | WT | MutB | MutC |
| The number of cells entered | ~2500 | ~750 | ~3000 |
| Number of cells in which Ig sequences are detected | 490 | 321 | 621 |
| Average number of read pairs per cell | 72054 | 125947 | 63305 |
| Number of cells with HV:LV pairs | 334 | 234 | 515 |
| Frequency that the representative antibody binds to the E protein as detected | 9/10 (90.0%) | 7/8 (87.5%) | 10/13 (76.9%) |

Analysis of antibody profiles in WT, MutB and MutC-induced mice showed that the AdC7-M/E-WT vaccine activated the variable region (V) gene in mice with a preference, in which about 60% of the heavy chains used IGHV9-2-1, IGHV1-22 and IGHV7-3, and about 60% of the light chains used IGKV10-96, IGKV14-111 and IGKV6-23 (FIG. 21). However, for the FL-substituted AdC7-M/E-MutB and AdC7-M/E-MutC vaccines, the BCR profiles showed more diversity and dispersion in both the heavy chain variable region (HV) and light chain variable region (LV) (FIG. 21). In the WT group, several variable region genes with the most significant activation were significantly reduced or even absent in the antibody profiles of the FL-substituted vaccine groups MutB and MutC groups (FIG. 21).

We then analyzed the paired HV and LV results in the antibody profile. The results were shown in FIG. 22, FIG. 23, FIG. 24-1 and FIG. 24-2, respectively.

It can be seen from FIG. 22 that the AdC7-M/E-WT vaccine activated the HV:LV of GC B cell clones in mice with a clear preference, in which IGHV9-2-1:IGKV10-96 (29.9%), IGHV1-22:IGKV14-111 (14.4%) and IGKV1-22: IGKV6-23 (7.5%) had the highest frequency. The sum of these three was about 50%.

As can be seen from FIG. 23 and FIGS. 24-1 and 24-2, HV:LVs of GC B cell clones in mice activated with AdC7-M/E-MutB and AdC7-M/E-MutC vaccines were more diverse and more dispersed in frequency distribution. The highest IGHV9-2-1:IGKV10-96 was detected in the WT group, which was absent in both MutB and MutC groups.

The results of antibody profiling showed that the immunodominant epitopes of the B cell response were transferred after substituting the FL region of the AdC7-M/E-WT vaccine.

Example 16 Identification of Major FLE Antibody Types with ADE Responsive to DENV Infection Most of the antibodies that caused the ADE response to DENV target FLEs of the E protein. Additionally, the antibodies induced by ZIKV infection also led to the ADE response to DENV. Therefore, we identified the binding characteristics of the isolated monoantibodies and detected which one bound with FLE and whether it induced the ADE response to DENV.

According to the similarity classification of GC B cell clones, some representative monoclonal antibody genes were synthesized (Jinweizhi, Suzhou), covering 63.38%, 46.57% and 43.88% of the sum totals of AdC7-M/E-WT, AdC7-M/E-MutB and AdC7-M/E-MutC group, respectively (Table 6). The HV and LV genes were subsequently cloned into murine IgG2A and Igκ expression vectors, respectively. The monoclonal antibodies derived from the AdC7-M/E-WT vaccine group (represented as M/E-WT in Table 6) were named as ZWT.1-10, and the monoclonal antibodies defived from the AdC7-M/E-MutB vaccine group (represented as M/E-MutB in Table 6) and AdC7-M/E-MutC vaccine group (represented as M/E-MutC in Table 6) were named as ZMutB.1-8 and ZMutC.1-13, respectively (Table 6).

TABLE 6

| | | | | | | | | | | | Expression of murine monoclonal antibodies | | |
|---|---|---|---|---|---|---|---|---|---|---|---|---|---|
| mAb ID | Vaccine group | HV gene | HD gene | HJ gene | CDRH3 length | HV simi-larity | LV gene | LJ gene | CDRL3 length | LV simi-larity | Number of clones per group clustered by genetic composition[a] | Fre-quency | Bind-ing to ZIKV sE[b] |
| ZWT.1 | M/E-WT | IGHV9-2-1*01 | IGHD2-1*01 | IGHJ 4*01 | 11 | 98.60% | IGKV10-96*01 | IGKJ 1*01 | 9 | 99.00% | 100 | 29.94% | Yes |
| ZWT.2 | M/E-WT | IGHV9-2-1*01 | IGHD2-13*01 | IGHJ 4*01 | 11 | 99.30% | IGKV10-96*01 | IGKJ 1*01 | 9 | 99.30% | | | |
| ZWT.3 | M/E-WT | IGHV9-2-1*01 | IGHD3-3*01 | IGHJ 4*01 | 11 | 95.60% | IGKV10-96*01 | IGKJ 1*01 | 9 | 97.90% | | | |
| ZWT.4 | M/E-WT | IGHV1-22*01 | IGHD1-1*01 | IGHJ 2*01 | 14 | 94.90% | IGKV14-111*01 | IGKJ 1*01 | 9 | 98.60% | 48 | 14.37% | Yes |
| ZWT.5 | M/E-WT | IGHV1-22*01 | IGHD1-1*02 | IGHJ 4*01 | 11 | 95.20% | IGKV14-111*01 | IGKJ 1*01 | 9 | 98.30% | | | |
| ZWT.6 | M/E-WT | IGHV1-22*01 | IGHD2-14*01 | IGHJ 2*01 | 16 | 95.90% | IGKV6-23*01 | IGKJ 2*01 | 8 | 97.90% | 25 | 7.40% | Yes |
| ZWT.7 | M/E-WT | IGHV3-2*02 | IGHD1-1*01 | IGHJ 2*01 | 12 | 99.00% | IGKV10-96*01 | IGKJ 1*01 | 9 | 99.70% | 13 | 3.89% | No |
| ZWT.8 | M/E-WT | IGHV7-3*02 | IGHD1-3*01 | IGHJ 2*01 | 10 | 97.70% | IGKV3-12*01 | IGKJ 1*01 | 8 | 98.00% | 10 | 2.99% | Yes |
| ZWT.9 | M/E-WT | IGHV9-2-1*01 | IGHD2-1*01 | IGHJ 4*01 | 11 | 99.70% | IGKV3-4*01 | IGKJ 2*01 | 8 | 98.00% | 10 | 2.99% | Yes |

TABLE 6-continued

Expression of murine monoclonal antibodies

| mAb ID | Vaccine group | HV gene | HD gene | HJ gene | CDRH3 length | HV similarity | LV gene | LJ gene | CDRL3 length | LV similarity | Number of clones per group clustered by genetic composition[a] | Frequency | Binding to ZIKV sE[b] |
|---|---|---|---|---|---|---|---|---|---|---|---|---|---|
| ZWT.10 | M/E-WT | IGHV1S34*01 | N/A | IGHJ4*01 | 11 | 97.00% | IGKV10-96*01 | IGKJ1*01 | 8 | 97.90% | 6 | 1.80% | Yes |
| ZMut B.1 | M/E-Mut B | IGHV1S130*01 | IGHD2-2*01 | IGHJ1*01 | 14 | 98.30% | IGKV8-24*01 | IGKJ1*01 | 9 | 99.30% | 38 | 16.23% | No |
| ZMut B.2 | M/E-Mut B | IGHV3-6*02 | IGHD1-3*01 | IGHJ3*01 | 9 | 99.00% | IGKV5-48*01 | IGKJ4*01 | 9 | 98.60% | 15 | 6.41% | Yes |
| ZMut B.3 | M/E-Mut B | IGHV3-2*02 | IGHD5-2*01 | IGHJ1*01 | 14 | 99.70% | IGKV2-109*01 | IGKJ5*01 | 9 | 98.70% | 13 | 5.56% | Yes |
| ZMut B.4 | M/E-Mut B | IGHV1-84*02 | N/A | IGHJ2*01 | 7 | 97.60% | IGKV4-57*01 | IGKJ5*01 | 9 | 97.20% | 12 | 5.12% | Yes |
| ZMut B.5 | M/E-Mut B | IGHV6-6*01 | IGHD3-1*01 | IGHJ2*01 | 12 | 99.30% | IGKV4-55*01 | IGKJ2*01 | 9 | 97.60% | 10 | 4.27% | Yes |
| ZMut B.6 | M/E-Mut B | IGHV1S121*01 | IGHD1-2*01 | IGHJ2*01 | 10 | 96.00% | IGKV12-41*01 | IGKJ1*01 | 8 | 99.60% | 8 | 3.42% | Yes |
| Z.Mut B.7 | M/E-Mut B | IGHV1-26*01 | IGHD2-2*01 | IGHJ1*01 | 17 | 93.50% | IGKV3-5*01 | IGKJ4*01 | 9 | 99.70% | 8 | 3.42% | Yes |
| ZMut B.8 | M/E-Mut B | IGHV9-2-1*01 | IGHD1-1*01 | IGHJ3*01 | 14 | 97.60% | IGKV3-10*01 | IGKJ5*01 | 9 | 98.70% | 5 | 2.14% | Yes |
| ZMut C.1 | M/E-Mut C | IGHV1S127*01 | N/A | IGHJ2*01 | 7 | 90.50% | IGKV8-30*01 | IGKJ2*01 | 9 | 98.70% | 27 | 5.24% | Yes |
| ZMut C.2 | M/E-Mut C | IGHV1-87*01 | N/A | IGHJ2*01 | 7 | 96.90% | IGKV8-30*01 | IGKJ2*01 | 9 | 99.70% | 23 | 4.47% | Yes |
| ZMut C.3 | M/E-Mut C | IGHV3-5*02 | IGHD6-2*01 | IGHJ1*01 | 13 | 98.90% | IGKV12-89*01 | IGKJ2*01 | 9 | 100.00% | 22 | 4.27% | Yes |
| ZMut C.4 | M/E-Mut C | IGHV9-3*02 | IGHD2-2*01 | IGHD2-7*01 | 14 | 99.70% | IGKV3-12*01 | IGKJ4*01 | 9 | 99.70% | 22 | 4.27% | Yes |
| ZMut C.5 | M/E-Mut C | IGHV3-5*02 | IGHD6-2*01 | IGHJ1*01 | 13 | 99.00% | IGKV12-89*01 | IGKJ2*01 | 9 | 100.00% | 22 | 4.27% | No |
| ZMut C.6 | M/E-Mut C | IGHV1-18*01 | IGHD2-14*01 | IGHJ1*01 | 13 | 92.20% | IGKV8-24*01 | IGKJ5*01 | 9 | 99.70% | 20 | 3.88% | No |
| ZMut C.7 | M/E-Mut C | IGHV9-2-1*01 | IGHD4-1*01 | IGHJ2*01 | 11 | 98.00% | IGKV8-30*01 | JGKJ5*01 | 9 | 99.30% | 18 | 3.50% | Yes |
| Z.Mut 0.8 | M/E-Mut C | IGHV6-6*03 | IGHD2-3*01 | IGHJ4*01 | 13 | 98.00% | IGKV4-70*01 | IGKJ5*01 | 9 | 98.60% | 17 | 3.30% | Yes |
| Z.Mut C.9 | ME-Mut C | IGHV9-3*02 | IGHD2-2*01 | IGHD2-7 | 14 | 99.70% | IGKV3-12*01 | IGKJ4*01 | 9 | 99.70% | 16 | 3.11% | Yes |
| ZMut C.10 | M/E-Mut C | IGHV5-17*02 | IGHD2-3*01 | IGHJ4*01 | 13 | 99.00% | IGKV1-110*01 | IGKJ2*01 | 9 | 99.70% | 15 | 2.91% | No |
| ZMut C.11 | M/E-Mut C | IGHV1-18*01 | IGHD2-2*01 | IGHJ2*01 | 10 | 90.10% | IGKV15-103*01 | IGKJ1*01 | 9 | 98.60% | 10 | 1.94% | Yes |
| ZMut C.12 | M/E-Mut C | IGHV3-6*02 | IGHD4-1*01 | IGHJ2*01 | 10 | 99.70% | IGKV4-55*01 | IGKJ1*01 | 9 | 99.30% | 8 | 1.55% | Yes |
| ZMut C.13 | M/E-Mut C | IGHV10S3*01 | IGHD2-2*01 | IGHJ3*01 | 10 | 98.30% | IGKV12-44*01 | IGKJ5*01 | 9 | 98.60% | 6 | 1.17% | Yes |

[a] Considering 7 elements of genes: the length of HV, HD, HJ gene and CDRH3 of the heavy chain, and the length of LV, LJ and CDRL3 of the light chain, when the clone has 4 or more same elements, it was considered to belong to the same gene cluster.
[b] ELISA detects the binding ability of each monoclonal antibody to ZIKV E (monomer or dimer). When the OD450 of the sample was higher than 5 times of the value of the negative control, it was considered to be binding, otherwise it was considered to be non-binding.

We co-transfected 293T cells with plasmids that express heavy chain and light chain of the monoclonal antibody. The supernatant was collected after 3 days. The binding ability of the antibody in the supernatant to ZIKV-E protein was detected by ELISA.

The experimental method of ELISA was as follows: Dilute the protein with ELISA coating solution (sodium carbonate-sodium bicarbonate buffer, pH 9.6) to 3 g/ml, add 100 μl to each well of 96-well ELISA plate, and leave standing overnight at 4° C. The next day, discard the coating solution, and block the ELISA plate with 5% nonfat milk in PBS, and leave at room temperature for 1 hour. Pour off the blocking solution, add 100 μl of the culture supernatant expressing monoclonal antibody to each well of the ELISA plate, incubate at room temperature for 2 hours, and wash 3 times with PBST. Afterwards, add Goat Anti-Mouse HRP (ab6789) secondary antibody diluted 1:2000 in blocking solution, incubate at room temperature for 1.5 hours, and wash 4 times with PBST. Add 50 μl of TMB chromogenic solution to develop color, add 50 μl of 2M hydrochloric acid after 30 minutes to stop the reaction, and detect the OD450 value on a microplate reader.

The ELISA test results were shown in FIG. 25. Most of the monoclonal antibodies could bind to the monomer or dimer form of the ZIKV sE protein. As can be seen from Table 6, the positive rate of binding reached 90% (9/10) in the ME-WT group, 87.5% in ME-MutB group (7/8), 76.9% in ME-MutC group (10/13), respectively.

Further evaluation of 26 positive monoclonal antibodies that bound to ZIKV sE protein was performed. From FIG. 25, we found that all monoclonal antibodies derived from ME-WT group did not react with ZIKV sE-MutC protein, but cross-reacted with the sE protein of DENV serotypes 1 to 4, indicating that the monoclonal antibody derived from the ME-WT group was a monoclonal antibody that binds to FLE; and the monoclonal antibodies derived from the ME-MutB and ME-MutC groups were mainly ZIKV-specific antibodies, and they were almost none of them bound to DENV sE.

Figure 26:
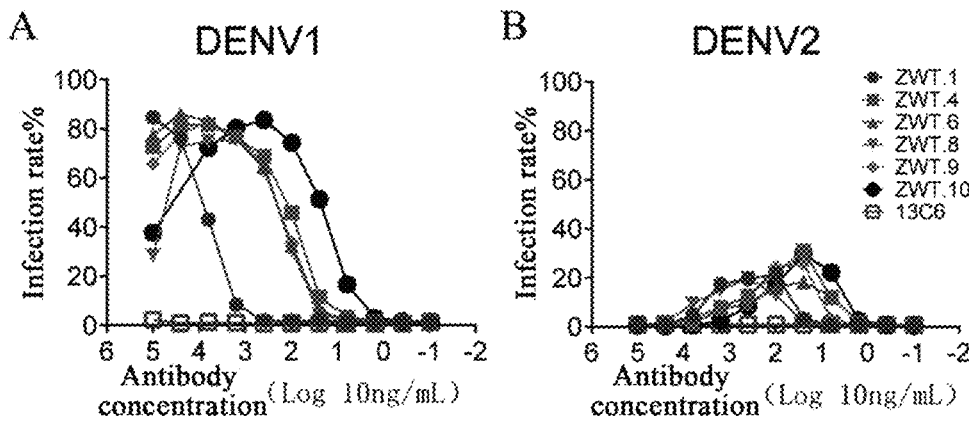
FIG. 26 shows the experimental result of detecting the antibodies induced in mice immunized with a representative AdC7-M/E-WT vaccine that promote the ADE effect of DENV-infected cells.
Figure 27:
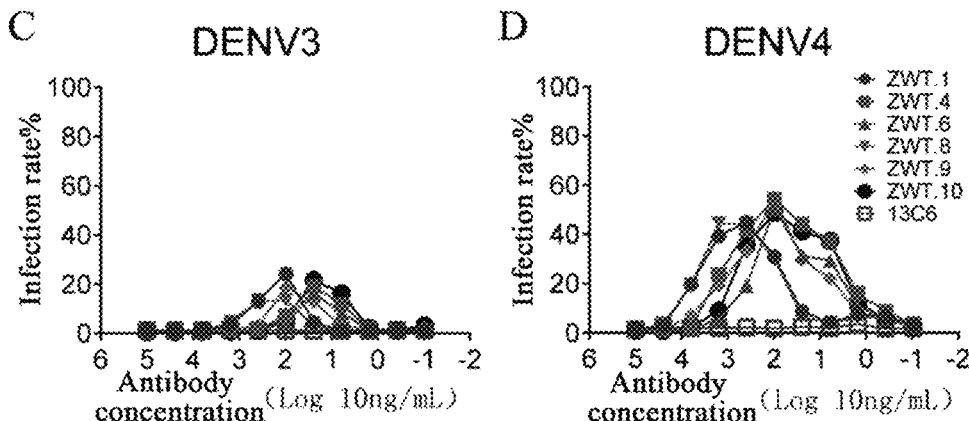
FIG. 27 shows the result of comparison of the monoclonal antibody induced by AdC7-M/E-WT vaccine-immunized mice using V locus with reported FLE monoclonal antibody.

We expressed and purified representative FLE monoclonal antibodies derived from the ME-WT group to further evaluate the ADE effect of these antibodies on DENV on K562 cells. The results were shown in FIG. 26. It can be seen from FIG. 26 that all the tested antibodies derived from the ME-WT group had a certain degree of enhanced infection effect on the four serotypes of DENV. Among them, in FIG. 26, ZWT.1, 4, 6, 8, 9, and 10 were monoclonal antibodies from the M/E-WT group. DENV 1, DENV 2, DENV 3, and DENV 4 were serotypes 1-4 of the DENV virus, respectively. The results of the enhanced infection of K562 cells promoted by the four serotypes of DENV by ZWT.1, 4, 6, 8, 9, 10 antibodies were from A to D.

The FLE monoclonal antibodies derived from the ME-WT group were mainly composed of four types of HV:LV genes. We tried to search the literature and databases for the previously reported *flavivirus* FLE murine monoclonal antibodies, which were then compared with the antibody loci and sequences we isolated. The following four monoclonal antibodies were found:

6B6C-1, which was isolated from tick-borne encephalitis virus (TBEV) after infection (Crill et al, (2004) Journal of Virology, 78.24: 13975-13986.);

both 4G2 and 2A10G6, which were isolated after DENV infection (Bennett et al. (2015), BMC Biotechnology, 15.1: 71-71.; Deng, Yongqiang, et al. (2011), PLOS ONE 6.1);

E53 which was isolated after WNV infection (Oliphant et al. (2006), Journal of Virology 80.24: 12149-12159.).

After analysis, it was found that the FLE monoclonal antibodies we isolated from the ME-WT group were more similar to the loci and sequences of these four reported monoclonal antibodies, as shown in FIG. 27, FIG. 28-1 and FIG. 28-2. It can be seen from FIG. 27 that 6B6C-1 and 4G2 use the same HV:LV gene pair as ZWT.1-3 and ZWT.4-5, respectively, and have a high sequence similarity; 2A10G6 and E53 use the same HV gene as ZWT.6 and ZWT.8, respectively.

Although the LV genes used by 2A10G6 and ZWT.6 were different, the LV sequences of the two antibodies were somewhat similar. As can be seen from FIG. 28-2, the CDRL3 and FR4 of 2A10G6 and ZWT.6 were identical.

From the above analysis, it was found that the FLE monoclonal antibody cloned from the lymph node GC B cells of mice immunized with the AdC7-M/E-WT vaccine had a locus that was close to or even the same as the reported mouse FLE monoclonal antibody, and the sequences were relatively similar. It showed that the locus used to induce antibodies that bound to the FL epitope in mice had a preference, and the characteristics of the produced FLE antibodies were also relatively similar.

Figures 1, 28:
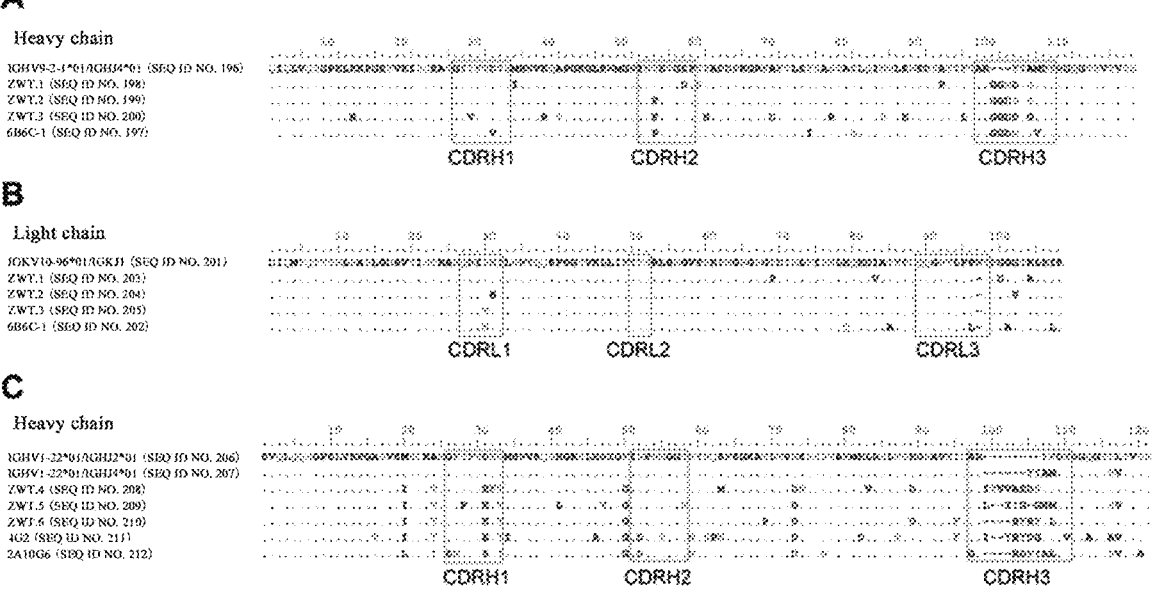
Figures 2, 28:
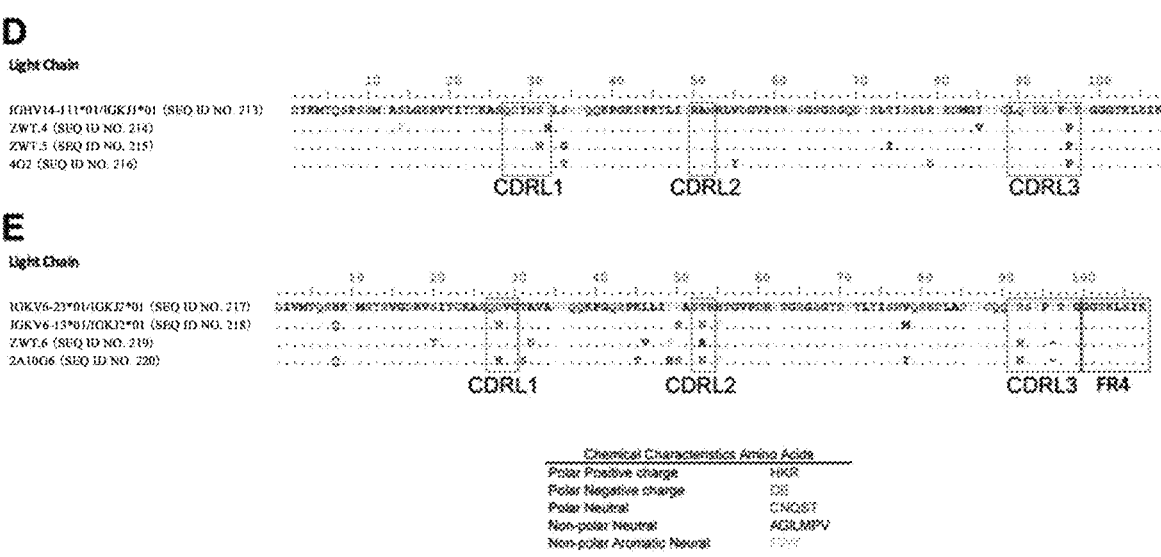

In FIG. 28-1, A showed the sequence alignment analysis of the antibody heavy chains of ZWT.1, ZWT.2, ZWT.3, and 6B6C-1 and the mouse locus, B showed the sequence alignment of the antibody light chain of ZWT.1, ZWT.2, ZWT.3, and 6B6C-1 and the mouse locus, and C showed the sequence alignment of the antibody heavy chain of ZWT.4, ZWT.5, ZWT.6, 4G2, and 2A10G6 and the mouse locus. In FIG. 28-2, D showed the sequence alignment of antibody light chain of ZWT.4, ZWT.5, and 4G2 and the mouse locus, and E showed the sequence alignment of antibody light chain of ZWT.6, and 2A10G6 and the mouse locus.

Example 17 SPR Assay to Detect the Affinity of Wild-Type and Mutant ZIKV E Proteins to ZIKV Antibodies Since the AdC7-M/E-MutB and AdC7-M/E-MutC vaccines were able to provide complete protection in mice while avoiding ADE against DENV, we expressed purified soluble sE-MutC protein as a representative to compare with sE-WT to explain the underlying molecular mechanism.

BIOCORE8000 was based on the principle of Surface Plasmon Resonance (SPR), which can detect the interaction between molecules, reflect the dynamic changes in the process of molecular binding in real time, and obtain the kinetic parameters of the interaction.

The affinity of ZIKV sE-WT protein and ZIKV sE-MutC protein to FLE antibody and non-FLE neutralizing antibody was detected using BIOCORE8000. Using a method of amino coupling, ZIKV sE-WT protein and ZIKV sE-MutC protein were immobilized on CM5 chip, respectively, and then four kinds of antibodies were diluted as mobile phase, which passes through fixed ZIKV sE protein. The corresponding signals were obtained when binding differently. The data was collected, fitted and computed. The results were shown in FIG. 29 and FIG. 30.

Figure 29:
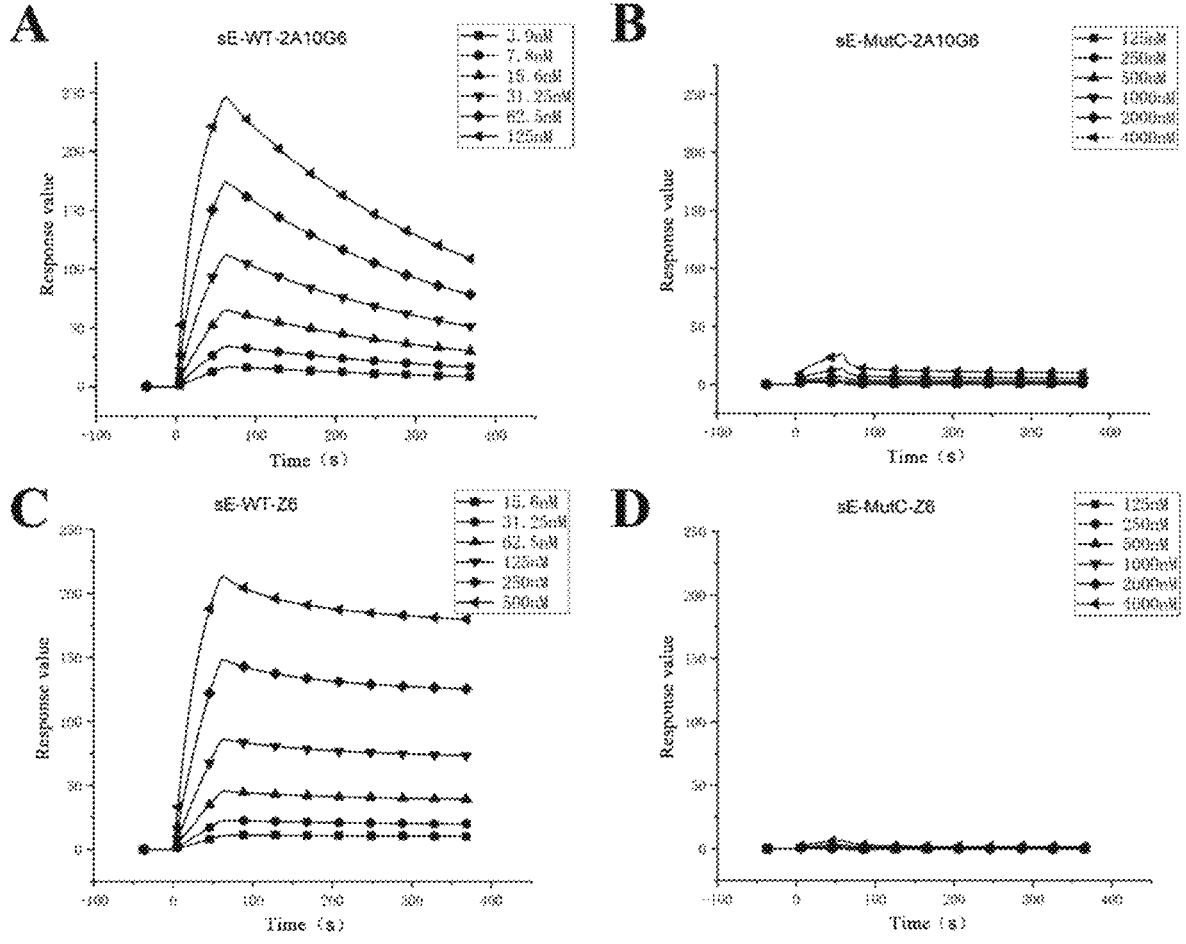
FIG. 29 shows the affinity results of ZIKV sE-WT protein and ZIKV sE-MutC protein with FLE antibody detected by BIAcore.

In FIG. 29, from A to D were the binding results of ZIKV sE-WT protein and 2A10G6 antibody (sE-WT-2A10G6), the binding results of ZIKV sE-MutC protein and 2A10G6 antibody (sE-MutC-2A10G6), binding results of ZIKV sE-WT protein and Z6 antibody (sE-WT-Z6), and binding results of ZIKV sE-MutC protein and Z6 antibody (sE-MutC-Z6), respectively. Among them, it can be seen from panel A in FIG. 29 that the affinity of 2A10G6 antibody binding to ZIKV sE-WT protein was 9.13 nM. From panel C in FIG. 29, it can be seen that the affinity of Z6 antibody binding to ZIKV sE-WT protein was 7.14 nM. From panel B in FIG. 29, it can be seen that ZIKV sE-MutC protein did not bind to 2A10G6 antibody at all. From panel D in FIG. 29, it can be seen that ZIKV sE-MutC protein did not bind to Z6 antibody at all. This result was also consistent with the theoretical analysis.

Figure 30:
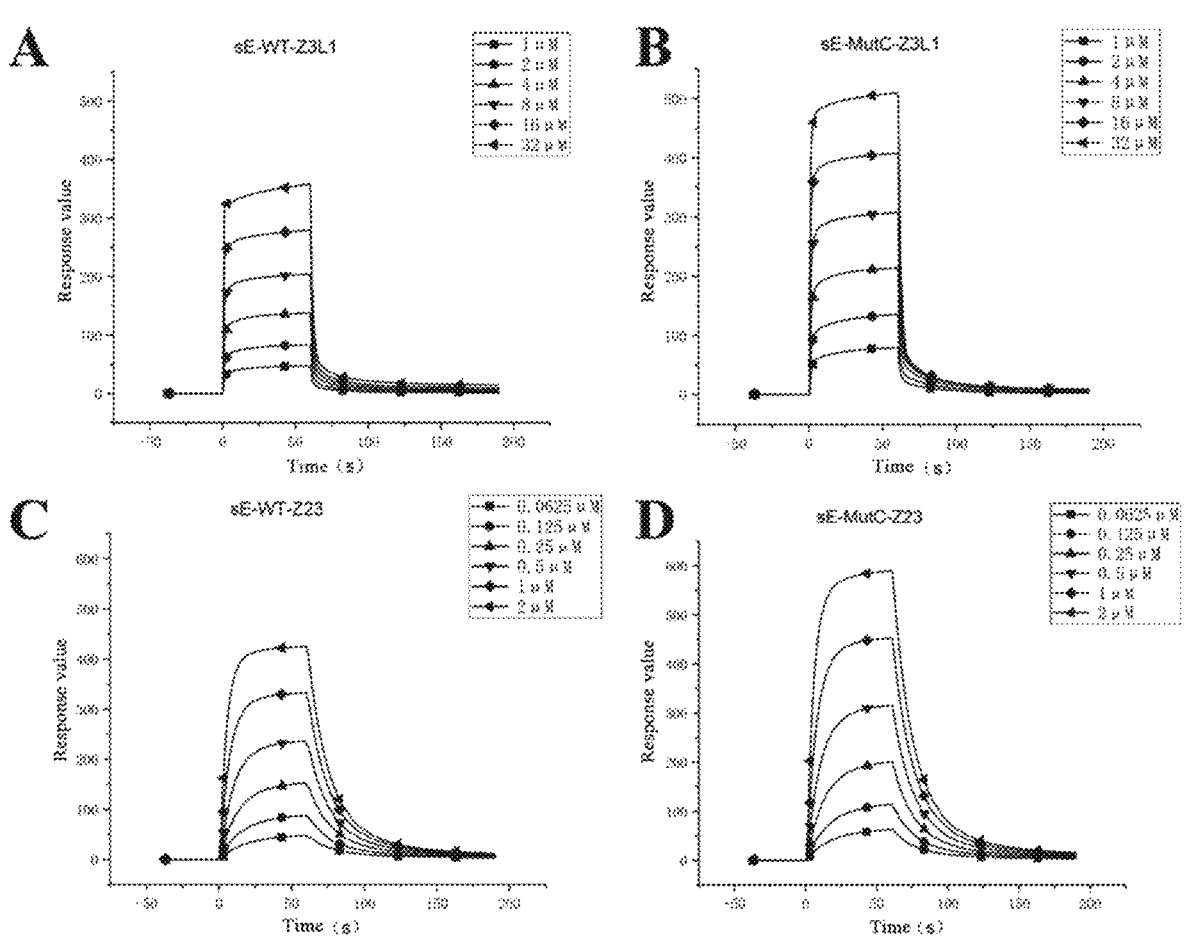
FIG. 30 shows the affinity results of ZIKV sE-WT protein and ZIKV sE-MutC protein with non-FLE neutralizing antibodies detected by BIAcore.

In FIG. 30, from A to D were the binding results of ZIKV sE-WT protein and Z3L1 antibody (sE-WT-Z3L1), the binding results of ZIKV sE-MutC protein and Z3L1 antibody (sE-MutC-Z3L1), binding results of ZIKV sE-WT protein and Z23 antibody (sE-WT-Z23), and binding results of ZIKV sE-MutC protein and Z23 antibody (sE-MutC-Z23), respectively. Among them, from panel A and panel C in FIG. 30, it can be seen that Z3L1 and Z23 antibodies bind to ZIKV E-WT protein with affinities of 9.48 M and 0.625 μM, respectively. From panel B and panel D in FIG. 30, it can be seen that Z3L1 and Z23 antibodies bind to ZIKV sE-MutC protein with affinities of 8.01 μM and 0.701 M, respectively. The affinity of the mutant protein ZIKV sE-MutC to Z23 and Z3L1 was almost unchanged compared with that of the wild-type ZIKV sE-WT protein. This indicated that the designed mutant could maintain the overall conformation of the protein and no change was made to epitopes other than the mutated site.

Figure 31:
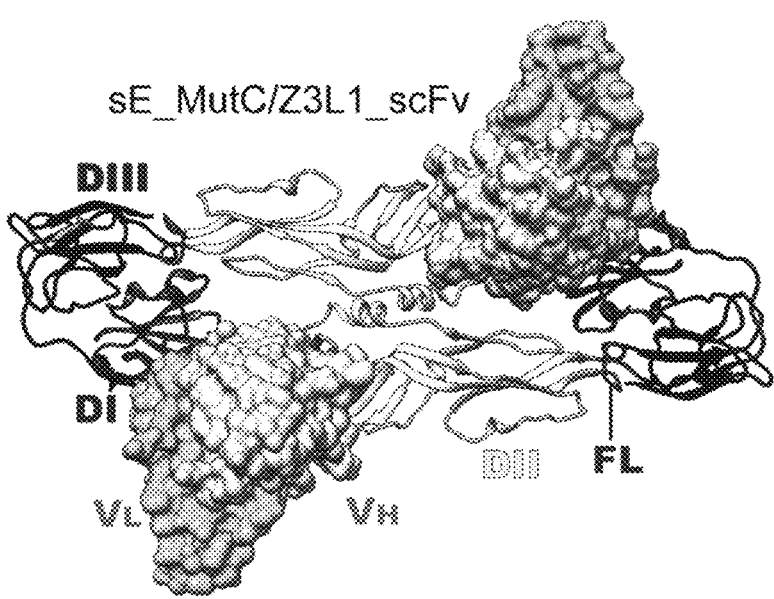
FIG. 31 shows a complex protein structure of ZIKV sE-MutC and Z3L1 single chain variable fragment (scFv).

Example 18 Structure Analysis of Complex of Mutant ZIKV sE-MutC Protein and Z3L1 Antibody To further explain the mechanism of action of the mutant vaccine, we purified the complex protein of ZIKV sE-MutC and Z3L1 single-chain variable fragment (scFv), followed by crystal screening. Through X-ray diffraction analysis and structure analysis, the atomic structure of the complex with a resolution of 3 A was obtained, as shown in FIG. 31. The data collection and optimized parameters of the complex were shown in Table 7.

TABLE 7

Data collection and optimized parameters for ZIKV sE MutC-Z3L1 complexes

| | ZIKV sE-Z3L1 |
| --- | --- |
| Data collection | |
| Space group | P 21 21 21 |
| Wavelength (Å) | 1.03923 |
| Cell parameter | |
| a, b, c(Å) | 78.46, 103.79, 205.82 |
| α, β, γ(°) | 90.00, 90.00, 90.00 |
| Resolution (Å) | 50.00-3.10 (3.21-3.10) |
| Observed reflection | 288956 |
| Integrity (%) | 99.2 (99.9) |
| Redundancy | 9.3 (9.8) |
| Rpim (%) | 5.6 (30.1) |
| I/σ | 12.4 (2.2) |
| Refinement | |
| Rwork/Rfree(%) | 22.23/26.80 |
| No. atoms | |
| Protein | 9754 |
| Ligand | 0 |
| Water | 0 |

TABLE 7-continued

Data collection and optimized parameters for ZIKV sE MutC-Z3L1 complexes

| | ZIKV sE-Z3L1 |
| --- | --- |
| B-factor | |
| Protein | 69.80 |
| Ligand | 0 |
| Water | 0 |
| r.m.s. deviation | |
| Bond length (Å) | 0.002 |
| Bond angle (°) | 0.491 |
| Ramachandran plot | |
| Favoured(%) | 100 |
| Allowed(%) | 0 |
| Outliers(%) | 0 |

Values in the parentheses indicate the highest resolution of the shell

As can be seen from FIG. 31, despite the introduction of 5 point mutations into the ZIKV E protein FL sequence, sE-MutC still bound to the scFV of Z3L1 in a dimer form as the state before fusion. A detailed analysis of the dimer contact interface showed that the mutated FL amino acid residues established a new interaction between two adjacent E protein domain, and generated four and one hydrogen bonds at N98 and W108, respectively, which were beneficial for the stabilization of E protein dimers, as shown in Table 8.

Figure 32:
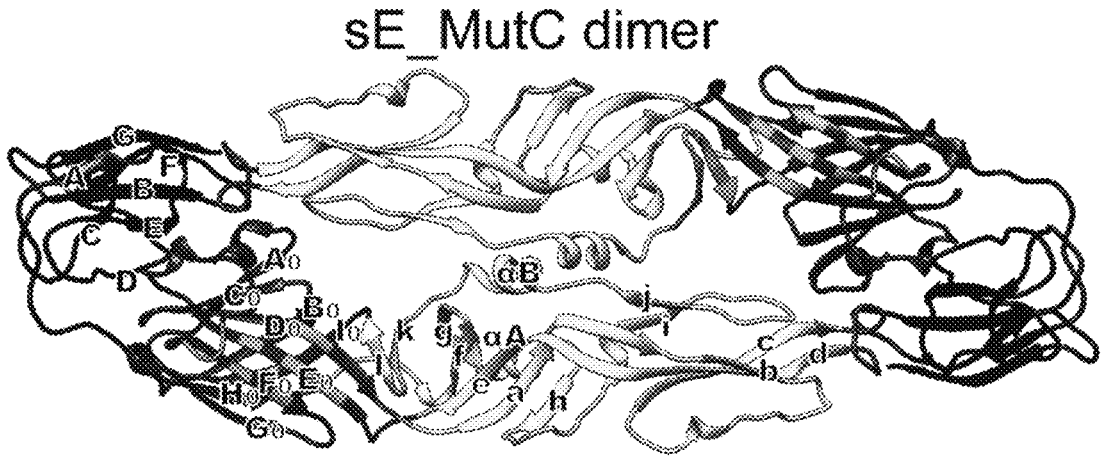
FIG. 32 shows the dimer structure of ZIKV sE-MutC protein.

As can be seen from FIG. 32, the folded form of sE-MutC was very similar to that of the wild-type protein, showing normal secondary, tertiary and quaternary epitope structures.

Figure 33:
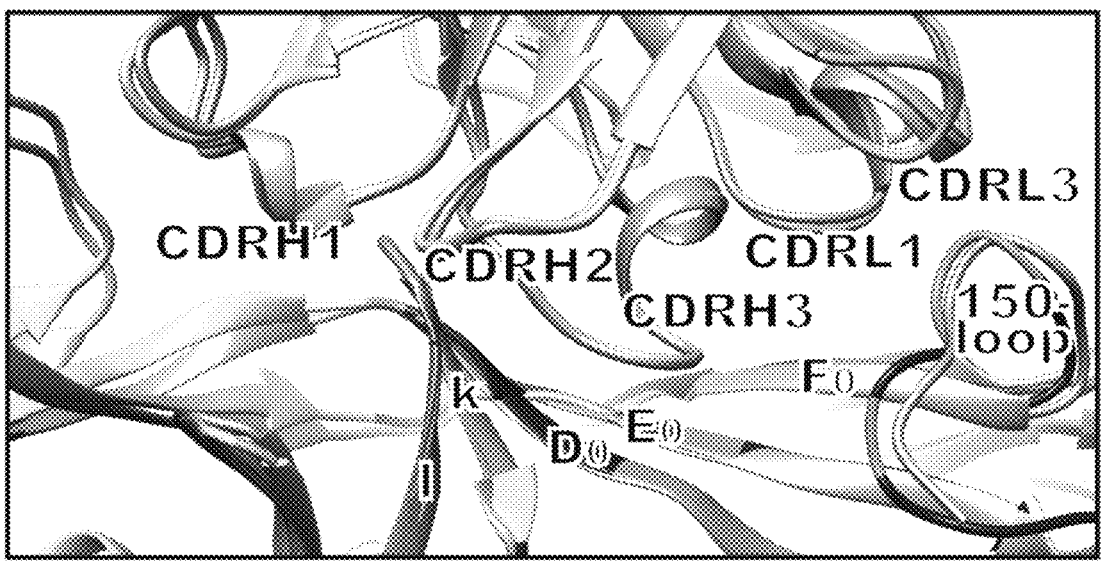
FIG. 33 shows the overlapping comparative analysis of the complex structure of Z3L1/ZIKV sE MutC and Z3L1/ZIKV sE WT (PDB: 5GZN) after.

To analyze the conformation of the neutralizing epitope, we overlapped the complex structures of ZIKV sE-MutC and Z3L1 scFv (Z3L1/ZIKV sE MutC) with the complex structures of Z3L1 and ZIKV sE-WT proteins (Z3L1/ZIKV sE WT, PDB:5GZN). The results were shown in FIG. 33. It can be seen from FIG. 33 that the ZIKV wild-type protein sE-WT and mutant protein sE-MutC have the same binding mode to Z3L1 antibody, and the binding sites were mainly D0, E0 and F0 strands and 150 loop in DI, as well as kl hairpin in DII (Wang, et al. (2016) Science translational medicine 8.369:369ra179.).

The FL region of sE-MutC and sE-WT were overlapped and analyzed for comparison. The results were shown in FIG. 34. It can be seen from FIG. 34 that the conformations of the FL epitopes of both were very similar, and only differs in the side chains of the mutation site.

To analyze the possibility of the mutant antigen sE-MutC inducing FLE antibodies, we overlapped the structures of FLE antibody having a known structure (Z6 antibody, 2A10G6 antibody and E53 antibody) that bound to *flavivirus* E protein with the DII structure of sE-MutC for analysis. The results were shown in FIG. 35.

Figures 34, 35:
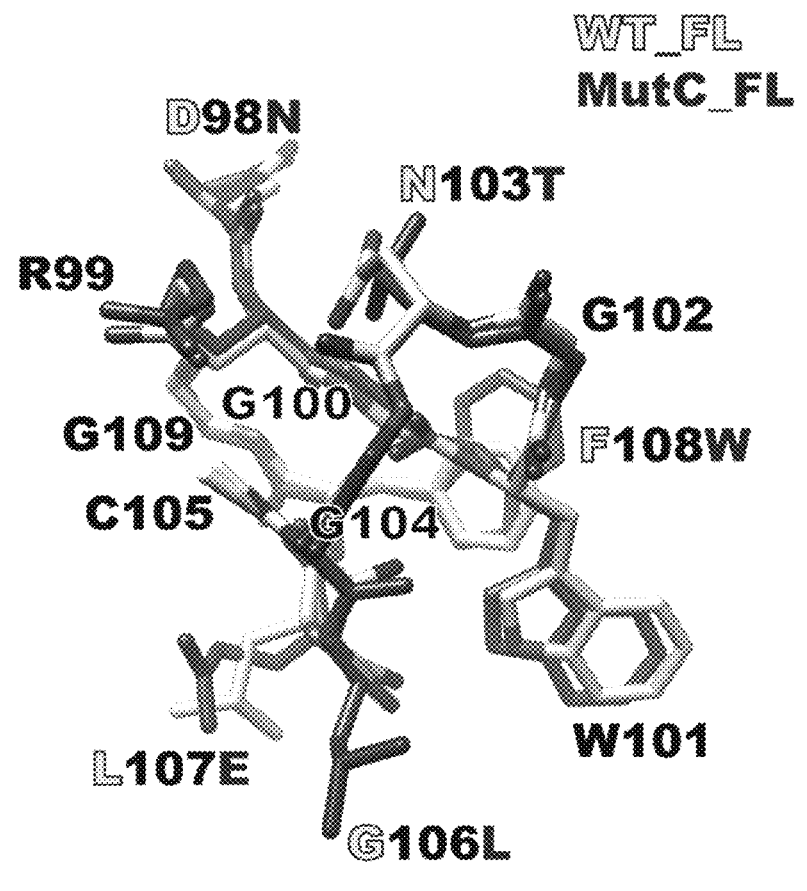
FIG. 34 shows the comparative analysis of the overlapping FL region of ZIKV sE-MutC and ZIKV sE-WT (PDB: 5JHM).
FIG. 35 shows the comparative analysis of the structure of FLE antibodies (Z6 antibody, 2A10G6 antibody and E53 antibody) binding to flavivirus E protein, overlapping with the DII complex structure of E protein.

In FIG. 35, the complex structures of Z6 antibody and ZIKV sE protein, 2A10G6 antibody and ZIKV sE protein (PDB: 5HIL), and E53 antibody and WNV sE protein (PDB: 3I50) were shown in A to C, respectively. It can be seen from FIG. 35 that after the imitated monoclonal antibody binds to sE-MutC, the mutations of G106, L107 and F108 will obviously hinder the binding of antigen and antibody. The protruding long side chain of G106L will lead to conflict with the binding of these FLE antibodies. The L107E mutation allows the formation of charged side chains, which may disrupt the local hydrophobic interactions in the interaction. In addition, the F108W mutation creates a steric hindrance that affects the interaction between the FL epitope of sE-MutC and the 2A10G6 antibody. Therefore, on the FL epitope of ZIKV E protein, the three key amino acid mutations G106, L107 and F108 achieve a synergistic effect, eliminating the induction of FLE antibodies.

First, the signal peptide gene (SEQ ID NO. 17) derived from JEV (Japanese encephalitis virus) and the M/E gene (SEQ ID NO. 18) expressing DENV2 of New Guinea C strain (GenBank: KM204118.1) were constructed into pshuttle vector to obtain plasmid pshuttle-DV2-M/E-WT expressing wild-type DENV2 M/E. The signal peptide gene (SEQ ID NO. 17) derived from JEV and the gene expressing the prM/E protein of DENV2 New Guinea C strain (SEQ ID

TABLE 8

| Analysis of amino acid interactions of two protomers in ZIKV E dimers | | | | |
|---|---|---|---|
| Domain A | | Contact[a] | Domain B | Total contacts |
| FL region | N98 | 5, 3, 7, 4 | G5 (1)[b], L322, S7 (3), V6 | 150 |
| | W101 | 3, 18, 5, 16, 5, 3, 5, 3 | I1, K316, M375, T327, A319, I317, V328, E329 | |
| | G102 | 9 | I1 | |
| | L106 | 1 | A319 | |
| | E107 | 1 | A319 | |
| | W108 | 5, 9, 13, 1, 10, 11, 3, 3 | A319, E320, T321, L322, T327 (1), I4, G5, I1 | |
| | G109 | 5 | L322 | |
| | K110 | 2 | S7 (1) | |
| Non-FL region | I1 | 4, 7, 1 | W108, G102, W101 | 267 |
| | I4 | 11 | W108 | |
| | G5 | 5, 4 | W108, N98 (1) | |
| | V6 | 2 | N98 | |
| | S7 | 7, 3 | N98 (1), K110 (1) | |
| | V153 | 1, 3 | T103, G102 | |
| | K209 | 3, 4 | K246, V256 | |
| | E244 | 2 | K209 | |
| | K246 | 8, 5 | E274, K209 | |
| | V256 | 5 | K209 | |
| | L258 | 2 | H266 | |
| | G259 | 8, 5, 6 | E262, H266, G263 | |
| | S260 | 3, 7, 1, 1 | E262, G263 (1), S260, A264 | |
| | Q261 | 10, 3, 1 | G263 (1), T267, A264 | |
| | E262 | 1, 4 | S260, G259 | |
| | G263 | 7, 4, 9 | G259, S260 (1), Q261 (1) | |
| | A264 | 1, 2, 5 | S260, Q261, A264 | |
| | H266 | 3, 4 | L258, G259 | |
| | T267 | 3 | Q261 | |
| | E274 | 9, 1 | K246 (2), E244 | |
| | K316 | 16, 2, 1 | W101, L106, C105 | |
| | I317 | 2 | W101 | |
| | A319 | 7, 3, 1, 1 | W101, W108, L106, E107 | |
| | E320 | 7 | W108 | |
| | T321 | 9 | W108 | |
| | L322 | 1, 3 | W108, N98 | |
| | T327 | 16, 8 | W101, W108 (1) | |
| | V328 | 6 | W101 | |
| | E329 | 3 | W101 | |
| | M375 | 6 | W101 | |

[a]Numbers represent the number of atom-to-atom contacts between amino acid residues of the two domains, analysed using the CCP4 suite of programs (the threshold for distance is 4.5 Å).
[b]The numbers in parentheses represent the number of possible hydrogen bonds between two amino acid residues.

Example 19 Construction of DENV Vaccines with MutA, MutB and MutC Mutants

How to avoid ADE in the design of DENV vaccine was still an open question (REF). The FL sequence of ZIKV was very conservative with that of DENV The experiments of the above system proved that AdC7-M/E-MutB and AdC7-M/E-MutC adenovirus vaccine could avoid ADE to DENV, and at the same time provided complete protection to mice. Therefore, DENV vaccines with MutA, MutB and MutC mutations were constructed to verify whether the vaccines have similar effects.

NO. 19) were constructed into pshuttle vector to obtain the wild-type DENV2 prM/E plasmid pshuttle-DV2-prM/E-WT.

All mutants were constructed based on M/E-WT antigen. MutA (D98N, N103T, G106F, L107E and F108W), MutB (D98N, N103T, G106F, L107K and F108W) and MutC (D98N, N103T, G106L, L107E and F108W) mutant plasmids were constructed using pshuttle-DV2-M/E-WT plasmid as template. The primer sequences used in the construction process were shown in Table 9.

TABLE 9

Primers used in the construction of pshuttle-DV2-M/E-WT, pshuttle-DV2-prM/E-WT, and pshuttle-DV2-M/E-MutA/B/C

| Plasmid | Name of primer | Primer sequence (5'-3') |
|---|---|---|
| pshuttle-DV2-prM/E-WT | DV2-prM/E-F | AAACGGGCCCTCTAGAGCCACCATGCTCAAC (SEQ ID NO. 20) |
| | DV2-E-R | TTTAACTTAAGCTTGGTACCTTAAGCTTGCACCATGACTCCC (SEQ ID NO. 21) |
| pshuttle-DV2-M/E-WT | DV2-M/E-F1 | AAACGGGCCCTCTAGAGCCACCATGCTCAACATTTTAAACAG AAGGAGGAGAACCGCCGGAATGATCATCATG (SEQ ID NO. 22) |
| | DV2-M/E-F2 | GGAGAACCGCCGGAATGATCATCATGCTGATCCCCACCGTGA TGGCCAGCGTGGCTCTGGTGCCCCATGTC (SEQ ID NO. 23) |
| | DV2-E-R | TTTAACTTAAGCTTGGTACCTTAAGCTTGCACCATGACTCCC (SEQ ID NO. 24) |
| pshuttle-DV2-M/E-MutA | DV2-mutA-R | GTGAACAGAGGCTGGGGCACAGGATGCTTCGAATGGGGAAA GGGAGGCATCGTGACTTG (SEQ ID NO. 25) |
| | DV2-mutA-F | TCCCCATTCGAAGCATCCTGTGCCCCAGCCTCTGTTCACCATG GAGTGCTTGCACACGA (SEQ ID NO. 26) |
| pshuttle-DV2-M/E-MutB | DV2-mutB-R | GTGAACAGAGGCTGGGGCACAGGATGCTTCAAGTGGGGAAA GGGAGGCATCGTGACTTG (SEQ ID NO. 27) |
| | DV2-mutB-F | TCCCCACTTGAAGCATCCTGTGCCCCAGCCTCTGTTCACCATG GAGTGCTTGCACACGA (SEQ ID NO. 28) |
| pshuttle-DV2-M/E-MutC | DV2-mutC-R | GTGAACAGAGGATGGGGCACAGGATGCCTGGAATGGGGCAA GGGCTCTTTAATCACTTG (SEQ ID NO. 29) |
| | DV2-mutC-F | GCCCCATTCCAGGCATCCTGTGCCCCATCCTCTGTTCACGAAG GTCCTACGACACACGA (SEQ ID NO. 30) |

293T cells were transfected with plasmids pshuttle-DV2-M/E-WT and pshuttle-DV2-prM/E-WT expressing wild-type protein, and three mutant plasmids, respectively. After 48 hours, the supernatant was removed. The cells were washed once with PBS, then trypsinized into single cells, centrifuged, resuspended in DMEM medium, and washed again with DMEM medium. Then, the Fixation and Permeabilization solution from BD Company was added, and placing on ice for 20 minutes. Then, the cells were collected by centrifugation at 800 g for 10 minutes and washed twice with 1×Perm/Wash buffer from BD company. Each sample was divided into 5 parts, adding Z6, 2A10G6 and mAb11 antibodies that bound to FL epitopes and mAb513 and D448 antibodies that bound to non-FL epitopes, respectively, and placing in a refrigerator at 4° C. for 1 hour. The cells were harvested by centrifugation and washed twice with 1×Perm/ Wash buffer. Next, Goat Anti-Human FITC (Proteintech, 00003-12) antibody was added, and placing in a refrigerator at 4° C. for 1 hour. The cells were harvested by centrifugation and washed twice with 1×Perm/Wash buffer. The cells were resuspended in PBS (200 μl per well). The positive proportion of the samples was detected by flow cytometry. The experimental results were shown in FIG. 36.

Figure 36:
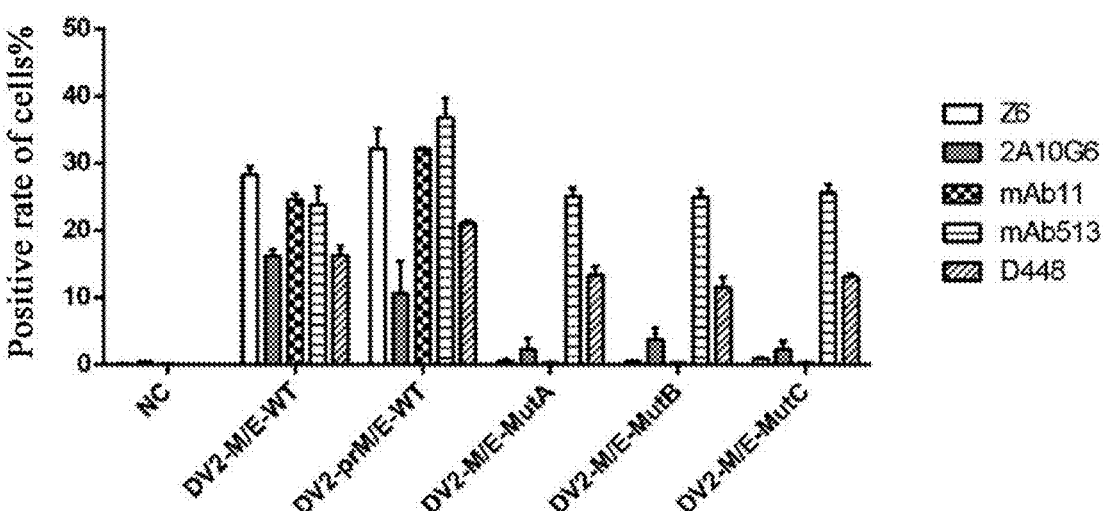
FIG. 36 shows the antigenic activity result of DENV2 wild-type and mutant E proteins using flow cytometry.

It can be seen from FIG. 36 that the antibodies Z6 and 2A10G6 that bound to the FL epitope could recognize the M/E-WT and prM/E-WT proteins of DENV2. However, after the FL epitope of the E protein of DENV2 was introduced with three mutation combinations, the binding ability of Z6 and 2A10G6 antibodies to the M/E-MutA or M/E-MutB or M/E-MutC proteins of DENV2 was greatly reduced or they even did not bind. For mAb513 and D448 antibodies that bound to non-FL epitopes with higher neutralizing activity, they could still bind to the M/E-MutA or M/E-MutB or M/E-MutC proteins of DENV2 introduced with MutA, MutB and MutC mutations, indicating that the mutation of the FL epitope of DENV2 E protein had no significant effect on other epitopes. The above results showed that these three mutation combinations could be used in DENV vaccines, and the vaccine obtained based on the DENV2 E protein antigen with the combination of G106, L107 and F108 site mutations may have reduced ADE effect caused by subsequent DENV virus infection after vaccine immunization.

Example 20 Detection of the Effect of ZIKV E W101 Mutation to Other 19 Amino Acids on Antigenic Activity In the structures of Z6/ZIKV sE and 2A10G6/ZIKV sE, W101 was the amino acid where E protein interacts most with antibodies. It had also been reported in the literature that most FLE antibodies bound to E protein by W101 (Dejnirattisai, W. et al (2015). Nat Immunol 16, 170-177.). Therefore, we tried to mutate W101 into other 19 amino acids, and then detected whether the epitope of the antigen expressed by cells was changed by cytometry to screen out the most suitable mutation.

The signal peptide gene (SEQ ID NO. 17) derived from JEV and the M/E gene (SEQ ID NO. 31) of wild-type ZIKV were constructed into pCAGGS vector (Addgene) to obtain the plasmid pCAGGS-M/E-WT that could express M/E protein of wild-type ZIKV Using this plasmid as a template, tryptophan at position 101 of E protein was mutated into other 19 amino acids. Taking the mutation of tryptophan to alanine as an example, using plasmid pCAGGS-M/E-WT as a template, and using W101-WT-F and W101-1A-R as primers, PCR product W101-1A-1 was obtained. For the primer sequence, see Table 10. Using plasmid pCAGGS-M/E-WT as template and W101-WT-R and W101-1A-F as primers, PCR product W101-1A-2 was obtained. Then, W101-1A-1 and W101-1A-2 were mixed in a molar ratio of 1:1 as a template, and W101-WT-F and W101-WT-R were used as primers for PCR to obtain PCR product W101-1A. The pCAGGS vector was restricted with XhoI (Thermo, FD0694) and EcoRI (Thermo, FD0274) to obtain a linear plasmid with double cohesive ends. The digested linear plasmid was mixed with W101-1A according to a molar ratio of 1:5, and the In-Fusion kit (Takara, 639648) was used for recombination. The recombinant product was transformed into DH5a competent cells, spread on ampicillin-resistant plates, and cultured at 37° C. After that, the clones were picked for PCR identification and sequencing identification.

TABLE 10

| Primer for tryptophan mutation at position 101 of E protein of ZIKV | | |
|---|---|---|
| Mutant form | Name of primer | Primer sequence (5'-3') |
| WT | W101-WT-F | TTTTGGCAAAGAATTCGCCG (SEQ ID NO. 32) |
| | W101-WT-R | GATCTGCTAGCTCGAGTCAAGCGCTCACAGCTGTGGACAGA (SEQ ID NO. 33) |
| W101A | W101-1A-R | CGCAGCCATTTCCGGCGCCCCTGTCCACCAGGGTCC (SEQ ID NO. 34) |
| | W101-1A-F | GGTGGACAGGGGCGCCGGAAATGGCTGCGGCCTGTTTG (SEQ ID NO. 35) |
| W101R | W101-2R-R | CGCAGCCATTTCCCCGGCCCCTGTCCACCAGGGTCC (SEQ ID NO. 36) |
| | W101-2R-F | GGTGGACAGGGGCCGGGGAAATGGCTGCGGCCTGTTTG (SEQ ID NO. 37) |
| W101N | W101-3N-R | CGCAGCCATTTCCGTTOCCCCTGTCCACCAGGGTCC (SEQ ID NO. 38) |
| | W101-3N-F | GGTGGACAGGGGCAACGGAAATGGCTGCGGCCTGTTTG (SEQ ID NO. 39) |
| W101D | W101-4D-R | CGCAGCCATTTCCGTCGCCCCTGTCCACCAGGGTCC (SEQ ID NO. 40) |
| | W101-4D-F | GGTGGACAGGGGCGACGGAAATGGCTGCGGCCTGTTTG (SEQ ID NO. 41) |
| W101C | W101-5C-R | CGCAGCCATTTCCGCAGCCCCTGTCCACCAGGGTCC (SEQ ID NO. 42) |
| | W101-5C-F | GGTGGACAGGGGCTGCGGAAATGGCTGCGGCCTGTTTG (SEQ ID NO. 43) |
| W101Q | W101-6Q-R | CGCAGCCATTTCCCTGGCCCCTGTCCACCAGGGTCC (SEQ ID NO. 44) |
| | W101-6Q-F | GGTGGACAGGGGCCAGGGAAATGGCTGCGGCCTGTTTG (SEQ ID NO. 45) |
| W101E | W101-7E-R | CGCAGCCATTTCCCTCGCCCCTGTCCACCAGGGTCC (SEQ ID NO. 46) |
| | W101-7E-F | GGTGGACAGGGGCGAGGGAAATGGCTGCGGCCTGTTTG (SEQ ID NO. 47) |
| W101G | W101-8G-R | CGCAGCCATTTCCGCCGCCCCTGTCCACCAGGGTCC (SEQ ID NO. 48) |
| | W101-8G-F | GGTGGACAGGGGCGGCGGAAATGGCTGCGGCCTGTTTG (SEQ ID NO. 49) |
| W101H | W101-9H-R | CGCAGCCATTTCCGTGGCCCCTGTCCACCAGGGTCC (SEQ ID NO. 50) |
| | W101-9H-F | GGTGGACAGGGGCCACGGAAATGGCTGCGGCCTGTTTG (SEQ ID NO. 51) |
| W101I | W101-10I-R | CGCAGCCATTTCCGATGCCCCTGTCCACCAGGGTCC (SEQ ID NO. 52) |
| | W101-10I-F | GGTGGACAGGGGCATCGGAAATGGCTGCGGCCTGTTTG (SEQ ID NO. 53) |
| W101L | W101-11L-R | CGCAGCCATTTCCCAGGCCCCTGTCCACCAGGGTCC (SEQ ID NO. 54) |
| | W101-11L-F | GGTGGACAGGGGCCTGGGAAATGGCTGCGGCCTGTTTG (SEQ ID NO. 55) |
| W101K | W101-12K-R | CGCAGCCATTTCCCTTGCCCCTGTCCACCAGGGTCC (SEQ ID NO. 56) |
| | W101-12K-F | GGTGGACAGGGGCAAGGGAAATGGCTGCGGCCTGTTTG (SEQ ID NO. 57) |
| W101M | W101-13M-R | CGCAGCCATTTOCCATGCCCCTGTCCACCAGGGTCC (SEQ ID NO. 58) |
| | W101-13M-F | GGTGGACAGGGGCATGGGAAATGGCTGCGGCCTGTTTG (SEQ ID NO. 59) |

TABLE 10-continued

```
        Primer for tryptophan mutation at position 101 of E protein of ZIKV
```

| Mutant form | Name of primer | Primer sequence (5'-3') |
|---|---|---|
| W101F | W101-14F-R | CGCAGCCATTTCCGAAGCCCCTGTCCACCAGGGTCC (SEQ ID NO. 60) |
| | W101-14F-F | GGTGGACAGGGGCTTCGGAAATGGCTGCGGCCTGTTTG (SEQ ID NO. 61) |
| W101P | W101-15P-R | CGCAGCCATTTCCGGGGCCCCTGTCCACCAGGGTCC (SEQ ID NO. 62) |
| | W101-15P-F | GGTGGACAGGGGCCCCGGAAATGGCTGCGGCCTGTTTG (SEQ ID NO. 63) |
| W101S | W101-16S-R | CGCAGCCATTTCCGCTGCCCCTGTCCACCAGGGTCC (SEQ ID NO. 64) |
| | W101-16S-F | GGTGGACAGGGGCAGCGGAAATGGCTGCGGCCTGTTTG (SEQ ID NO. 65) |
| W10IT | W101-17T-R | CGCAGCCATTTCCGGTGCCCCTGTCCACCAGGGTCC (SEQ ID NO. 66) |
| | W101-17T-F | GGTGGACAGGGGCACCGGAAATGGCTGCGGCCTGTTTG (SEQ ID NO. 67) |
| W101Y | W101-19Y-R | CGCAGCCATTTCCGTAGCCCCTGTCCACCAGGGTCC (SEQ ID NO. 68) |
| | W101-19Y-F | GGTGGACAGGGGCTACGGAAATGGCTGCGGCCTGTTTG (SEQ ID NO. 69) |
| W101V | W101-20V-R | CGCAGCCATTTCCCACGCCCCTGTCCACCAGGGTCC (SEQ ID NO. 70) |
| | W101-20V-F | GGTGGACAGGGGCGTGGGAAATGGCTGCGGCCTGTTTG (SEQ ID NO. 71) |

After extraction of 19 mutant plasmids of W101, 293T cells were transfected with wild-type plasmids and 19 mutant plasmids, respectively. After 48 hours, the supernatant was removed. The cells were washed once with PBS, then trypsinized into single cells, centrifuged, resuspended in DMEM medium, and washed again with DMEM medium. Then, the Fixation and Permeabilization solution from BD Company was added, and placing on ice for 20 minutes. Then, the cells were collected by centrifugation at 800 g for 10 minutes and washed twice with 1×Perm/Wash buffer from BD company. Each sample was divided into 5 parts, adding Z6 and 2A10G6 antibodies respectively, and placing in a refrigerator at 4° C. for 1 hour. The cells were harvested by centrifugation and washed twice with 1×Perm/Wash buffer. Next, Goat Anti-Human FITC (Proteintech, 00003-12) antibody was added, and placing in a refrigerator at 4° C. for 1 hour. The cells were harvested by centrifugation and washed twice with 1×Perm/Wash buffer. The cells were resuspended in PBS (200 µl per well). The positive proportion of the samples was detected by flow cytometry. The experimental results were shown in FIG. 37.

Figure 37:
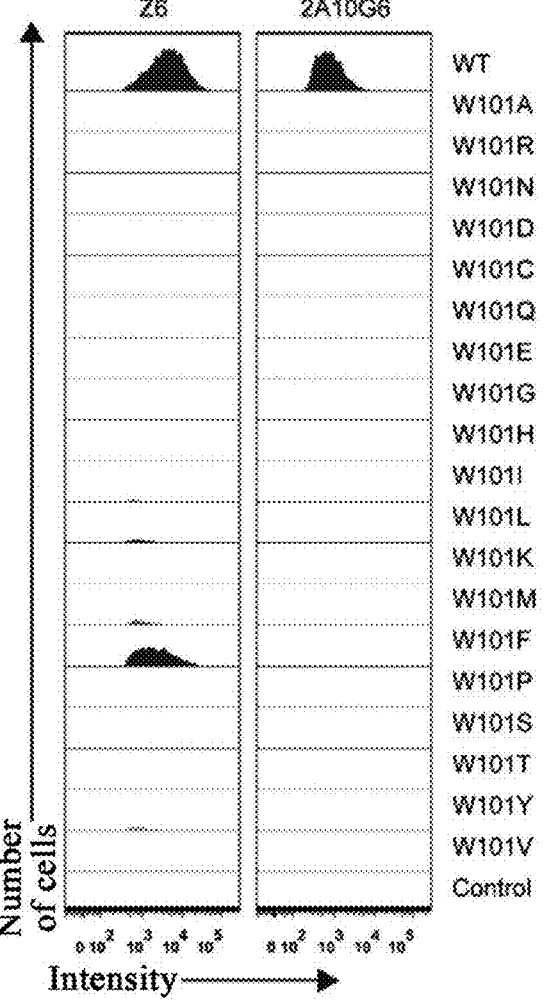
FIG. 37 shows the antigenic activity result of tryptophan at position 101 of ZIKV E protein to other 19 amino acids using flow cytometry.

It can be seen from FIG. 37 that ZIKV wild-type M/E antigen could bind to Z6 and 2A10G6 antibodies, while all 19 mutants can hardly bind to Z6 and 2A10G6 antibodies, indicating that tryptophan at position 101 of ZIKV E protein was important for activating antibodies targeting FL. The vaccine prepared by the W101 site mutation will reduce or avoid the production of FL epitope-induced antibodies, thereby avoiding the ADE effect on DENV after vaccine immunization.

Example 21 Detecting the Binding Ability of ZIKV E Protein with G106, L107 and F108 Site Mutations on FLE Antibody Based on the above-mentioned pCAGGS-ZIKV-M/E expression plasmid, the following single-site and double-site mutations were performed. The construction method of the mutant plasmid referred to Example 20. For the primers used in the construction of the mutant plasmid, see Table 11.

TABLE 11

| Primers used for sites mutation of G106, L107 and F108 of ZIKV E protein | | |
|---|---|---|
| Mutation site | Mutation form | Upstream and downstream primers |
| G106 mutation | G106L | G106L-F: CTGCT GTTTG GAAAG GGCTC CCTGG TGACC TG (SEQ ID NO. 72) <br> G106L-R: AAACAGCAGGCAGCCATTT CCCCAGC CCC TGT (SEQ ID NO. 73) |
| | G106F | G106F-F: TTCCTGTTTGGAAAGGGCTCCCTGGTGAC CT G (SEQ ID NO. 74) <br> G106F-R: AAACAGGAAGCAGCCATTTCCCCAGCCCC TGT (SEQ ID NO. 75) |
| | G106W | G106W-F: TGGCTGTTTGGAAAGGGCTCCCTGGTGACC TG (SEQ ID NO. 76) |

TABLE 11-continued

Primers used for sites mutation of G106, L107 and F108 of ZIKV E protein

| Mutation site | Mutation form | Upstream and downstream primers |
|---|---|---|
| | | G106W-R: AAACAGCCAGCAGCCATTTCCCCAGCCCCT GT (SEQ ID NO. 77) |
| | G106Y | G106Y-F: TACCTGTTTGGAAAGGGCTCCCTGGTGACC TG (SEQ ID NO. 78) |
| | | G106Y-R: AAACAGGTAGCAGCCATTTCCCCAGCCCCT GT (SEQ ID NO. 79) |
| | G106I | G106I-F: ATCCTGTTTGGAAAGGGCTCCCTGGTGACCTG (SEQ ID NO. 80) |
| | | G106I-R: AAACAGGATGCAGCCATTTCCCCAGCCCCTG T (SEQ ID NO. 81) |
| L107 mutation | L107E | L107E-F: GGCGAGTTTGGAAAGGGCTCCCTGGTGACC TG (SEQ ID NO. 82) |
| | | L107E-R: AAACTCGCCGCAGCCATTTCCCCAGCCCCT GT (SEQ ID NO. 83) |
| | L107K | L107K-F: GGCAAGTTTGGAAAGGGCTCCCTGGTGACCT G (SEQ ID NO. 84) |
| | | L107K-R: AAACTTGCCGCAGCCATTTCCCCAGCCCCTG T (SEQ ID NO. 85) |
| | L107R | L107R-F: GGCCGGTTTGGAAAGGGCTCCCTGGTGACCT G (SEQ ID NO. 86) |
| | | L107R-R: AAACCGGCCGCAGCCATTTCCCCAGCCCCTG T (SEQ ID NO. 87) |
| | L107D | L107D-F: GGCGACTTTGGAAAGGGCTCCCTGGTGACC TG (SEQ ID NO. 88) |
| | | LI07D-R: AAAGTCGCCGCAGCCATTTCCCCAGCCCCT GT (SEQ ID NO. 89) |
| | L107T | L107T-F: GGCACCTTTGGAAAGGGCTCCCTGGTGACC TG (SEQ ID NO. 90) |
| | | L107T-R: AAAGGTGCCGCAGCCATTTCCCCAGCCCCT GT (SEQ ID NO. 91) |
| F108 mutation | F108W | F108W-F: GGCCTGTGGGGAAAGGGCTCCCTGGTGA CCTG (SEQ ID NO. 92) |
| | | F108W-R: CCACAGGCCGCAGCCATTTCCCCAGCCCCT GT (SEQ ID NO. 93) |
| | F108H | F108H-F: GGCCTGCACGGAAAGGGCTCCCTGGTGACC TG (SEQ ID NO. 94) |
| | | F108H-R: GTGCAGGCCGCAGCCATTTCCCCAGCCCCTG T (SEQ ID NO. 95) |
| | F108Y | F108Y-F: GGCCTGTACGGAAAGGGCTCCCTGGTGACCT G (SEQ ID NO. 96) |
| | | F108Y-R: GTACAGGCCGCAGCCATTTCCCCAGCCCCTG T (SEQ ID NO. 97) |
| | F108P | F108P-F: GGCCTGCCCGGAAAGGGCTCCCTGGTGACCT G (SEQ ID NO. 98) |
| | | F108P-R: GGGCAGGCCGCAGCCATTTCCCCAGCCCCTG T (SEQ ID NO. 99) |
| | F108A | F108A-F: GGCCTGGCCGGAAAGGGCTCCCTGGTGACCT G (SEQ ID NO. 100) |
| | | F108A-R: GGCCAGGCCGCAGCCATTTCCCCAGCCCCTG T (SEQ ID NO. 101) |
| G106/L107 mutation | G106L/L107E | G106L/L107E-F: CTGGAGTTTGGAAAGGGCTCCCTGGT GACCTG (SEQ ID NO. 102) |
| | | G106L/L107E-R: AAACTCCAGGCAGCCATTTCCCCAGC CCCTGT (SEQ ID NO. 103) |
| | G106L/L107K | G106L/L107K-F: CTGAAGTTTGGAAAGGGCTCCCTGG TGACCTG (SEQ ID NO. 104) |
| | | G106L/L107K-R: AAACTTCAGGCAGCCATTTCCCCAG CCCCTGT (SEQ ID NO. 105) |
| | G106F/L107E | G106F/L107E-F: TTCGAGTTTGGAAAGGGCTCCCTGGTG ACCTG (SEQ ID NO. 106) |
| | | G106F/L107E-R: AAACTCGAAGCAGCCATTTCCCCAGC CCCTGT (SEQ ID NO. 107) |
| | G106F/L107K | G106F/L107K-F: TTCAAGTTTGGAAAGGGCTCCCTGGT GACCTG (SEQ ID NO. 108) |
| | | G106F/L107K-R: AAACTTGAAGCAGCCATTTCCCCAGC CCCTGT (SEQ ID NO. 109) |
| | G106F/L107R | G106F/L107R-F: TTCCGGTTTGGAAAGGGCTCCCTGGTG ACCTG (SEQ ID NO. 110) |
| | | G106F/L107R-R: AAACCGGAAGCAGCCATTTCCCCAGC CCCTGT (SEQ ID NO. 111) |
| G106/F108 mutation | G106F/F108W | G106F/F108W-F: TTCCTGTGGGGAAAGGGCTCCCTGGT GACCTG (SEQ ID NO. 112) |

TABLE 11-continued

Primers used for sites mutation of G106, L107 and F108 of ZIKV E protein

| Mutation site | Mutation form | Upstream and downstream primers |
|---|---|---|
| | | G106F/F108W-R: CCACAGGAAGCAGCCATTTCCCCAG CCCCTGT (SEQ ID NO. 113) |
| | G106L/F108W | G106L/F108W-F: CTGCTGTGGGGAAAGGGCTCCCTGGT GACCTG (SEQ ID NO. 114) |
| | | G106L/F108W-R: CCACAGCAGGCAGCCATTTCCCCAGC CCCTGT (SEQ ID NO. 115) |
| | G106F/F108H | G106F/F108H-F: TTCCTGCACGGAAAGGGCTCCCTGG TGACCTG (SEQ ID NO. 116) |
| | | G106F/F108H-R: GTGCAGGAAGCAGCCATTTCCCCAG CCCCTGT (SEQ ID NO. 117) |
| | G106Y/F108W | G106Y/F108W-F: TACCTGTGGGGAAAGGGCTCCCTGG TGACCTG (SEQ ID NO. 118) |
| | | G106Y/F108W-R: CCACAGGTAGCAGCCATTTCCCCAGC CCCTGT (SEQ ID NO. 119) |
| | G106W/F108Y | G106W-F: TGGCTGTACGGAAAGGGCTCCCTGG TGACCTG (SEQ ID NO. 120) |
| | | G106W-R: GTACAGCCAGCAGCCATTTCCCCAGCCC CTGT (SEQ ID NO. 121) |
| L107/F108 mutation | LI07E/F108W | L107E/F108W-F: GGCGAGTGGGGAAAGGGCTCCCTG GTGACCTG (SEQ ID NO. 122) |
| | | L107E/F108W-R: CCACTCGCCGCAGCCATTTCCCCAG CCCCTGT (SEQ ID NO. 123) |
| | LI07K/F108W | L107K/F108W-F: GGCAAGTGGGGAAAGGGCTCCCTGGT GACCTG (SEQ ID NO. 124) |
| | | L107K/F108W-R: CCACTTGCCGCAGCCATTTCCCCAG CCCCTGT (SEQ ID NO. 125) |
| | L107R/F108W | L107R/F108W-F: GGCCGGTGGGGAAAGGGCTCCCTG GTGACCTG (SEQ ID NO. 126) |
| | | L107R/F108W-R: CCACCGGCCGCAGCCATTTCCCCAG CCCCTGT (SEQ ID NO. 127) |
| | L107D/F108W | L107D/F108W-F: GGCGACTGGGGAAAGGGCTCCCTG GTGACCTG (SEQ ID NO. 128) |
| | | L107D/F108W-R: CCAGTCGCCGCAGCCATTTCCCCA GCCCCTGT (SEQ ID NO. 129) |
| | L107K/F108Y | L107K/F108Y-F: GGCAAGTACGGAAAGGGCTCCCTG GTGACCTG (SEQ ID NO. 130) |
| | | L107K/F108Y-R: GTACTTGCCGCAGCCATTTCCCCAGC CCCTGT (SEQ ID NO. 131) |

The wild-type plasmid pCAGGS-ZIKV-M/E-WT and the successfully constructed mutant plasmid were transfected into 293T cells respectively. After 48 hours, the cells were harvested, digested into single cells, fixed and permeabilized, incubated with FL epitope-binding ADE antibodies Z6 and 2A10G6, and incubated with Goat Anti-Human (mouse) FITC secondary antibody. Finally, the positive proportion of samples was measured by flow cytometry. If the positive proportion was lower than 10% of the wild-type positive rate, it was considered as non-binding, and if 10%-50% of the wild-type positive rate, it was considered as weak binding. The results were shown in Table 12.

It can be seen from Table 12 that the above mutations could basically prevent the binding of the FL epitope representative ADE antibodies (Z6 antibody and 2A10G6 antibody), indicating that the vaccine prepared by the single point or synergistic mutation of G106, L107 and F108 sites represented by these mutations will reduce or avoid the production of the ADE antibodies that was induced by FL epitope, thereby avoiding the ADE effect on DENV after vaccine immunization.

TABLE 12

Results of ZIKV E protein mutants binding to Z6 antibody and 2A10G6 antibody

| Mutation site | Mutation form | FLE antibody | |
|---|---|---|---|
| | | Z6 | 2A10G6 |
| G106 mutation | G106L | — | — |
| | G106F | — | — |
| | G106W | — | — |
| | G106Y | — | — |
| | G106I | — | — |
| L107 mutation | L107E | — | — |
| | L107K | — | — |
| | L107R | — | — |
| | L107D | — | — |
| | L107T | — | — |
| F108 mutation | F108W | Weak binding | — |
| | F108H | — | — |
| | F108Y | — | — |
| | F108P | — | — |
| | F108A | — | — |
| G106/L107 mutation | G106L/L107E | — | — |
| | G106L/L107K | — | — |
| | G106F/L107E | — | — |
| | G106F/L107K | — | — |
| | G106F/L107R | — | — |
| G106/F108 mutation | G106F/F108W | — | — |
| | G106L/F108W | — | — |
| | G106F/F108H | — | — |
| | G106Y/F108W | — | — |
| | G106W/F108Y | — | — |

TABLE 12-continued

Results of ZIKV E protein mutants binding
to Z6 antibody and 2A10G6 antibody

| Mutation site | Mutation form | FLE antibody | |
|---|---|---|---|
| | | Z6 | 2A10G6 |
| L107/F108 mutation | L107E/F108W | — | — |
| | L107K/F108W | — | — |
| | L107R/F108W | — | — |
| | L107D/F108W | — | — |
| | L107K/F108Y | — | — |

Note:
— means no binding.

Example 22 Detecting the Binding Ability of DENV E Protein with G106, L107 and F108 Site Mutations on FLE Antibody Based on the above-mentioned pCAGGS-DENV2-M/E expression plasmid, the following single-site and double-site mutations were performed. The construction method of the mutant plasmid referred to Example 19. For the primers used in the construction of the mutant plasmid, see Table 13.

TABLE 13

Primers used for mutation of G106, L107 and F108 sites of DENV E protein

| Mutation site | Mutation form | Upstream and downstream primers |
|---|---|---|
| G106 mutation | G106L | G106L-F: CTGTTATTCGGAAAGGGAGGCATCGTGACTTG (SEQ ID NO. 132)<br>G106L-R: GAATAACAGGCATCCATTGCCCCAGCCTCTGT (SEQ ID NO. 133) |
| | G106F | G106F-F: TTCTTATTCGGAAAGGGAGGCATCGTGACTTG (SEQ ID NO. 134)<br>G106F-R: GAATAAGAAGCATCCATTGCCCCAGCCTCTGT (SEQ ID NO. 135) |
| | G106W | G106W-F: TGGTTATTCGGAAAGGGAGGCATCGTGACTTG (SEQ ID NO. 136)<br>G106W-R: GAATAACCAGCATCCATTGCCCCAGCCTCTGT (SEQ ID NO. 137) |
| | G106Y | G106Y-F: TACTTATTCGGAAAGGGAGGCATCGTGACTTG (SEQ ID NO. 138)<br>G106Y-R: GAATAAGTAGCATCCATTGCCCCAGCCTCTGT(SEQ ID NO. 139) |
| | G106I | G106I-F: ATCTTATTCGGAAAGGGAGGCATCGTGACTTG(SEQ ID NO. 140)<br>G106I-R: GAATAAGATGCATCCATTGCCCCAGCCTCTGT(SEQ ID NO. 141) |
| L107 mutation | L107E | L107E-F: GGTGAGTTCGGAAAGGGAGGCATCGTGACTTG (SEQ ID NO. 142)<br>L107E-R: GAACTCACCGCATCCATTGCCCCAGCCTCTGT (SEQ ID NO. 143) |
| | L107K | L107K-F: GGTAAGTTCGGAAAGGGAGGCATCGTGACTTG (SEQ ID NO. 144)<br>L107K-R: GAACTTACCGCATCCATTGCCCCAGCCTCTGT(SEQ ID NO. 145) |
| | L107R | L107R-F: GGTCGGTTCGGAAAGGGAGGCATCGTGACTTG (SEQ ID NO. 146)<br>L107R-R: GAACCGACCGCATCCATTGCCCCAGCCTCTGT (SEQ ID NO. 147) |
| | L107D | L107D-F: GGTGACTTCGGAAAGGGAGGCATCGTGACTTG (SEQ ID NO. 148)<br>L107D-R: GAAGTCACCGCATCCATTGCCCCAGCCTCTGT (SEQ ID NO. 149) |
| | L107T | L107T-F: GGTACCTTCGGAAAGGGAGGCATCGTGACTTG (SEQ ID NO. 150)<br>L107T-R: GAAGGTACCGCATCCATTGCCCCAGCCTCTGT(SEQ ID NO. 151) |
| F108 mutation | F108W | F108W-F: GGTTTATGGGGAAAGGGAGGCATCGTGACTTG (SEQ ID NO. 152)<br>F108W-R: CCATAAACCGCATCCATTGCCCCAGCCTCTGT (SEQ ID NO. 153) |
| | F108H | F108H-F: GGTTTACACGGAAAGGGAGGCATCGTGACTTG (SEQ ID NO. 154)<br>F108H-R: GTGTAAACCGCATCCATTGCCCCAGCCTCTGT(SEQ ID NO. 155) |
| | F108Y | F108Y-F: GGTTTATACGGAAAGGGAGGCATCGTGACTTG (SEQ ID NO. 156)<br>F108Y-R: GTATAAACCGCATCCATTGCCCCAGCCTCTGT(SEQ ID NO. 157) |

TABLE 13-continued

Primers used for mutation of G106, L107 and F108 sites of DENV E protein

| Mutation site | Mutation form | Upstream and downstream primers |
|---|---|---|
|  | F108P | F108P-F: GGTTTACCCGGAAAGGGAGGCATCGTGACTTG (SEQ ID NO. 158)<br>F108P-R: GGGTAAACCGCATCCATTGCCCCAGCCTCTGT(SEQ ID NO. 159) |
|  | F108A | F108A-F: GGTTTAGCCGGAAAGGGAGGCATCGTGACTTG (SEQ ID NO. 160)<br>F108A-R: GGCTAAACCGCATCCATTGCCCCAGCCTCTGT (SEQ ID NO. 161) |
| G106/L107 mutation | G106L/L107E | G106L/L107E-F: CTGGAGTTCGGAAAGGGAGGCATCG TGACTTG (SEQ ID NO. 162)<br>G106L/L107E-R: GAACTCCAGGCATCCATTGCCCCAGCCTC TGT (SEQ ID NO. 163) |
|  | G106L/L107K | G106L/L107K-F: CTGAAGTTCGGAAAGGGAGGCATCGTG ACTTG (SEQ ID NO. 164)<br>G106L/L107K-R: GAACTTCAGGCATCCATTGCCCCAGC CTCTGT (SEQ ID NO. 165) |
|  | G106F/L107E | G106F/L107E-F: TTCGAGTTCGGAAAGGGAGGCATC GTGACTTG (SEQ ID NO. 166)<br>G106F/L107E-R: GAACTCGAAGCATCCATTGCCCCAG CCTCTGT (SEQ ID NO. 167) |
|  | G106F/L107K | G106F/L107K-F: TTCAAGTTCGGAAAGGGAGGCATCG TGACTTG (SEQ ID NO. 168)<br>G106F/L107K-R: GAACTTGAAGCATCCATTGCCCCAG CCTCTGT (SEQ ID NO. 169) |
|  | G106F/L107R | G106F/L107R-F: TTCCGGTTCGGAAAGGGAGGCATCG TGACTTG (SEQ ID NO. 170)<br>G106F/L107R-R: GAACCGGAAGCATCCATTGCCCCAG CCTCTGT (SEQ ID NO. 171) |
| G106/F108 mutation | G106F/F108W | G106F/F108W-F: TTCTTATGGGGGAAAGGGAGGCATCGT GACTTG (SEQ ID NO. 172)<br>G106F/F108W-R: CCATAAGAAGCATCCATTGCCCCAGCC TCTGT (SEQ ID NO. 173) |
|  | G106L/F108W | G106L/F108W-F: CTGTTATGGGGGAAAGGGAGGCATC GTGACTTG (SEQ ID NO. 174)<br>G106L/F108W-R: CCATAACAGGCATCCATTGCCCCAG CCTCTGT (SEQ ID NO. 175) |
|  | G106F/F108H | G106F/F108H-F: TTCTTACACGGAAAGGGAGGCATC GTGACTTG (SEQ ID NO. 176)<br>G106F/F108H-R: GTGTAAGAAGCATCCATTGCCCCAG CCTCTGT (SEQ ID NO. 177) |
|  | G106Y/F108W | G106Y/F108W-F: TACTTATGGGGGAAAGGGAGGCATCGTGACTTG (SEQ ID NO. 178)<br>G106Y/F108W-R: CCATAAGTAGCATCCATTGCCCCAGCCT CTGT (SEQ ID NO. 179) |
|  | G106W/F108Y | G106W/F108Y-F: TGGTTATACGGAAAGGGAGGCATCGTG ACTTG (SEQ ID NO. 180)<br>G106W/F108Y-R: GTATAACCAGCATCCATTGCCCCAGCCT CTGT (SEQ ID NO. 181) |
| L107/F108 mutation | L107E/F108W | L107E/F108W-F: GGTGAGTGGGGAAAGGGAGGCATCGT GACTTG (SEQ ID NO. 182)<br>L107E/F108W-R: CCACTCACCGCATCCATTGCCCCAGCC TCTGT (SEQ ID NO. 183) |
|  | L107K/F108W | L107K/F108W-F: GGTAAGTGGGGAAAGGGAGGCATCGTG ACTTG (SEQ ID NO. 184)<br>L107K/F108W-R: CCACTTACCGCATCCATTGCCCCAGCCTC TGT (SEQ ID NO. 185) |
|  | L107R/F108W | L107R/F108W-F: GGTCGGTGGGGAAAGGGAGGCATCGTGA CTTG (SEQ ID NO. 186)<br>L107R/F108W-R: CCACCGACCGCATCCATTGCCCCAGCCTC TGT (SEQ ID NO. 187) |
|  | L107D/F108W | L107D/F108W-F: GGTGACTGGGGAAAGGGAGGCATCGTGA CTTG (SEQ ID NO. 188)<br>L107D/F108W-R: CCAGTCACCGCATCCATTGCCCCAGCCT CTGT (SEQ ID NO. 189) |
|  | L107K/F108Y | L107K/F108Y-F: GGTAAGTACGGAAAGGGAGGCATCGTGA CTTG (SEQ ID NO. 190)<br>L107K/F108Y-R: GTACTTACCGCATCCATTGCCCCAGCCTC TGT (SEQ ID NO. 191) |

293T cells were transfected with the wild-type plasmids pCAGGS-ZIKV-M/E-WT, pCAGGS-DENV2-M/E-WT and the mutant constructs in the above table, respectively. After 48 hours, the cells were harvested, digested into single cells, fixed and permeabilized, incubated with FL epitope-binding ADE antibodies Z6 and 2A10G6, and incubated with Goat Anti-Human (mouse) FITC secondary antibody. Finally, the positive proportion of samples was measured by flow cytometry. If the positive proportion was lower than 10% of the wild-type positive rate, it was considered as non-binding, and if 10%-50% of the wild-type positive rate, it was considered as weak binding. The results were shown in Table 14.

It can be seen from Table 14 that the above mutations could basically prevent the binding of the FL epitope representative ADE antibody, indicating that the vaccine prepared by the single point or synergistic mutation of G106, L107 and F108 represented by these mutations will reduce or avoid the production of the ADE antibodies that was induced by FL epitope, thereby avoiding the ADE effect on DENV after vaccine immunization.

TABLE 14

Results of DENV E protein mutants binding
to Z6 antibody and 2A10G6 antibody

| Mutation site | Mutation form | FLE antibody | |
| | | Z6 | 2A10G6 |
| --- | --- | --- | --- |
| G106 mutation | G106L | — | — |
| | G106F | — | — |
| | G106W | — | — |
| | G106Y | — | — |
| | G106I | — | — |
| L107 mutation | L107E | — | — |
| | L107K | — | — |
| | L107R | — | — |
| | L107D | — | — |
| | L107T | — | — |
| F108 mutation | F108W | Weak binding | — |
| | F108H | — | — |
| | F108Y | — | — |
| | F108P | — | — |
| | F108A | — | — |
| G106/L107 mutation | G106L/L107E | — | — |
| | G106L/L107K | — | — |
| | G106F/L107E | — | — |
| | G106F/L107K | — | — |
| | G106F/L107R | — | — |
| G106/F108 mutation | G106F/F108W | — | — |
| | G106L/F108W | — | — |

TABLE 14-continued

Results of DENV E protein mutants binding
to Z6 antibody and 2A10G6 antibody

| Mutation site | Mutation form | FLE antibody | |
| | | Z6 | 2A10G6 |
| --- | --- | --- | --- |
| | G106F/F108H | — | — |
| | G106Y/F108W | — | — |
| | G106W/F108Y | — | — |
| L107/F108 mutation | L107E/F108W | — | — |
| | L107K/F108W | — | — |
| | L107R/F108W | — | — |
| | L107D/F108W | — | — |
| | L107K/F108Y | — | — |

Note:
— means no binding.

Finally, it should be noted that: the above examples were only used to illustrate the technical solutions of the present disclosure, but not to limit them. Although the present disclosure has been described in detail with reference to the foregoing examples, those of ordinary skill in the art should understand: modifications can still be made to the technical solutions described in the foregoing examples, or some technical features thereof can be equivalently replaced; and these modifications or replacements do not make the essence of the corresponding technical solutions depart from the spirit and scope of the technical solutions of the examples of the present disclosure.

INDUSTRIAL APPLICABILITY

Examples in the present disclosure relates to a Zika/dengue vaccine and its application thereof.

The present application has obtained the epitope information of an antibody that causes ADE effect based on crystal structure analysis and other structural and functional analysis. The present disclosure provides antigens, in which some mutations are introduced into the E-protein FL fusion region of the Zika virus or dengue virus. All antigens with said mutations are unable to bind to antibodies causing ADE (FLE antigen). After immunization with the vaccine of the present disclosure acquired from the said antigens, production of FL epitope-induced antibodies can be prevented, thereby reducing or eliminating the ADE effect.

The invention claimed is:

1. An antigen comprising a Zika virus E protein, wherein an amino acid sequence of the E protein comprises SEQ ID NO. 1 having the mutations D98N, N103T, G106F, L107K and F108W.

2. The antigen according to claim 1, wherein:
the antigen further comprises a full sequence M protein of Zika virus.

3. The antigen according to claim 1, wherein:
the antigen further comprises a full sequence prM protein of Zika virus.

* * * * *

SEQUENCE LISTING

```
<160> NUMBER OF SEQ ID NOS: 220

<210> SEQ ID NO 1
<211> LENGTH: 504
<212> TYPE: PRT
<213> ORGANISM: zika virus

<400> SEQUENCE: 1

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
```

-continued

```
65                70                75                80

Tyr Leu Asp Lys Gln Ser Asp Thr Gln Tyr Val Cys Lys Arg Thr Leu
                85                90                95

Val Asp Arg Gly Trp Gly Asn Gly Cys Gly Leu Phe Gly Lys Gly Ser
            100               105               110

Leu Val Thr Cys Ala Lys Phe Ala Cys Ser Lys Lys Met Thr Gly Lys
            115               120               125

Ser Ile Gln Pro Glu Asn Leu Glu Tyr Arg Ile Met Leu Ser Val His
        130               135               140

Gly Ser Gln His Ser Gly Met Ile Val Asn Asp Thr Gly His Glu Thr
145               150               155               160

Asp Glu Asn Arg Ala Lys Val Glu Ile Thr Pro Asn Ser Pro Arg Ala
                165               170               175

Glu Ala Thr Leu Gly Gly Phe Gly Ser Leu Gly Leu Asp Cys Glu Pro
            180               185               190

Arg Thr Gly Leu Asp Phe Ser Asp Leu Tyr Tyr Leu Thr Met Asn Asn
            195               200               205

Lys His Trp Leu Val His Lys Glu Trp Phe His Asp Ile Pro Leu Pro
        210               215               220

Trp His Ala Gly Ala Asp Thr Gly Thr Pro His Trp Asn Asn Lys Glu
225               230               235               240

Ala Leu Val Glu Phe Lys Asp Ala His Ala Lys Arg Gln Thr Val Val
                245               250               255

Val Leu Gly Ser Gln Glu Gly Ala Val His Thr Ala Leu Ala Gly Ala
            260               265               270

Leu Glu Ala Glu Met Asp Gly Ala Lys Gly Arg Leu Ser Ser Gly His
            275               280               285

Leu Lys Cys Arg Leu Lys Met Asp Lys Leu Arg Leu Lys Gly Val Ser
        290               295               300

Tyr Ser Leu Cys Thr Ala Ala Phe Thr Phe Thr Lys Ile Pro Ala Glu
305               310               315               320

Thr Leu His Gly Thr Val Thr Val Glu Val Gln Tyr Ala Gly Thr Asp
            325               330               335

Gly Pro Cys Lys Val Pro Ala Gln Met Ala Val Asp Met Gln Thr Leu
            340               345               350

Thr Pro Val Gly Arg Leu Ile Thr Ala Asn Pro Val Ile Thr Glu Ser
            355               360               365

Thr Glu Asn Ser Lys Met Met Leu Glu Leu Asp Pro Pro Phe Gly Asp
        370               375               380

Ser Tyr Ile Val Ile Gly Val Gly Glu Lys Lys Ile Thr His His Trp
385               390               395               400

His Arg Ser Gly Ser Thr Ile Gly Lys Ala Phe Glu Ala Thr Val Arg
            405               410               415

Gly Ala Lys Arg Met Ala Val Leu Gly Asp Thr Ala Trp Asp Phe Gly
            420               425               430

Ser Val Gly Gly Ala Leu Asn Ser Leu Gly Lys Gly Ile His Gln Ile
            435               440               445

Phe Gly Ala Ala Phe Lys Ser Leu Phe Gly Gly Met Ser Trp Phe Ser
        450               455               460

Gln Ile Leu Ile Gly Thr Leu Leu Val Trp Leu Gly Leu Asn Thr Lys
465               470               475               480

Asn Gly Ser Ile Ser Leu Met Cys Leu Ala Leu Gly Gly Val Leu Ile
            485               490               495
```

-continued

Phe Leu Ser Thr Ala Val Ser Ala
          500

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
ttttggcaaa gaattcgccg                                            20

<210> SEQ ID NO 3
<211> LENGTH: 41
<212> TYPE: DNA
<213> ORGANISM: Artificial Sequence
<220> FEATURE:
<223> OTHER INFORMATION: Synthetic construct

<400> SEQUENCE: 3
gatctgctag ctcgagtcaa gcgctcacag ctgtggacag a                    41

<210> SEQ ID NO 4
<211> LENGTH: 55
<212> TYPE: DNA
<213> ORGANISM: Artificial Sequence
<220> FEATURE:
<223> OTHER INFORMATION: Synthetic construct

<400> SEQUENCE: 4
gtgtaagagg accctggtga acaggggctg gggaacaggc tgcttcgaat gggga       55

<210> SEQ ID NO 5
<211> LENGTH: 54
<212> TYPE: DNA
<213> ORGANISM: Artificial Sequence
<220> FEATURE:
<223> OTHER INFORMATION: Synthetic construct

<400> SEQUENCE: 5
gtgaacaggg gctggggaac aggctgcttc gaatggggaa agggctccct ggtg        54

<210> SEQ ID NO 6
<211> LENGTH: 55
<212> TYPE: DNA
<213> ORGANISM: Artificial Sequence
<220> FEATURE:
<223> OTHER INFORMATION: Synthetic construct

<400> SEQUENCE: 6
gtgtaagagg accctggtga acaggggctg gggaacaggc tgcttcaagt gggga       55

<210> SEQ ID NO 7
<211> LENGTH: 54
<212> TYPE: DNA
<213> ORGANISM: Artificial Sequence
<220> FEATURE:
<223> OTHER INFORMATION: Synthetic construct

<400> SEQUENCE: 7
gtgaacaggg gctggggaac aggctgcttc aagtggggaa agggctccct ggtg        54

<210> SEQ ID NO 8
<211> LENGTH: 55

-continued

```
<212> TYPE: DNA
<213> ORGANISM: Artificial Sequence
<220> FEATURE:
<223> OTHER INFORMATION: Synthetic construct

<400> SEQUENCE: 8
gtgtaagagg accctggtga acaggggctg gggaacaggc tgcctggaat gggga          55

<210> SEQ ID NO 9
<211> LENGTH: 54
<212> TYPE: DNA
<213> ORGANISM: Artificial Sequence
<220> FEATURE:
<223> OTHER INFORMATION: Synthetic construct

<400> SEQUENCE: 9
gtgaacaggg gctggggaac aggctgcctg gaatggggaa agggctccct ggtg           54

<210> SEQ ID NO 10
<211> LENGTH: 37
<212> TYPE: DNA
<213> ORGANISM: Artificial Sequence
<220> FEATURE:
<223> OTHER INFORMATION: Synthetic construct

<400> SEQUENCE: 10
aaacgggccc tctagagcca ccatgggcaa gaggagc                             37

<210> SEQ ID NO 11
<211> LENGTH: 40
<212> TYPE: DNA
<213> ORGANISM: Artificial Sequence
<220> FEATURE:
<223> OTHER INFORMATION: Synthetic construct

<400> SEQUENCE: 11
tttaacttaa gcttggtacc tcaagcgctc acagctgtgg                          40

<210> SEQ ID NO 12
<211> LENGTH: 30
<212> TYPE: DNA
<213> ORGANISM: Artificial Sequence
<220> FEATURE:
<223> OTHER INFORMATION: Synthetic construct

<400> SEQUENCE: 12
gtataactat aacggtccta aggtagcgaa                                     30

<210> SEQ ID NO 13
<211> LENGTH: 30
<212> TYPE: DNA
<213> ORGANISM: Artificial Sequence
<220> FEATURE:
<223> OTHER INFORMATION: Synthetic construct

<400> SEQUENCE: 13
tcattacctc tttctccgca cccgacatag                                     30

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
```
ccacacctct gccggcacac                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ttggctggcc tatcaggttg                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
cacctcggtt tgagcactct                  20

<210> SEQ ID NO 17
<211> LENGTH: 24
<212> TYPE: PRT
<213> ORGANISM: Japanese encephalitis virus

<400> SEQUENCE: 17

Met Gly Lys Arg Ser Ala Gly Ser Ile Met Trp Leu Ala Ser Leu Ala
1                5                10                15

Val Val Ile Ala Cys Ala Gly Ala
          20

<210> SEQ ID NO 18
<211> LENGTH: 570
<212> TYPE: PRT
<213> ORGANISM: Dengue virus

<400> SEQUENCE: 18

Ser Val Ala Leu Val Pro His Val Gly Met Gly Leu Glu Thr Arg Thr
1                5                10                15

Glu Thr Trp Met Ser Ser Glu Gly Ala Trp Lys His Ala Gln Arg Ile
          20                25                30

Glu Thr Trp Ile Leu Arg His Pro Gly Phe Thr Ile Met Ala Ala Ile
          35                40                45

Leu Ala Tyr Thr Ile Gly Thr Thr His Phe Gln Arg Ala Leu Ile Phe
          50                55                60

Ile Leu Leu Thr Ala Val Ala Pro Ser Met Thr Met Arg Cys Ile Gly
65                70                75                80

Ile Ser Asn Arg Asp Phe Val Glu Gly Val Ser Gly Gly Ser Trp Val
          85                90                95

Asp Ile Val Leu Glu His Gly Ser Cys Val Thr Thr Met Ala Lys Asn
          100             105             110

Lys Pro Thr Leu Asp Phe Glu Leu Ile Lys Thr Glu Ala Lys Gln Pro
          115             120             125

Ala Thr Leu Arg Lys Tyr Cys Ile Glu Ala Lys Leu Thr Asn Thr Thr
          130             135             140

Thr Asp Ser Arg Cys Pro Thr Gln Gly Glu Pro Ser Leu Asn Glu Glu
145                150              155              160

Gln Asp Lys Arg Phe Val Cys Lys His Ser Met Val Asp Arg Gly Trp

-continued

```
                165                 170                 175

Gly Asn Gly Cys Gly Leu Phe Gly Lys Gly Gly Ile Val Thr Cys Ala
            180                 185                 190

Met Phe Thr Cys Lys Lys Asn Met Lys Gly Lys Val Val Gln Pro Glu
            195                 200                 205

Asn Leu Glu Tyr Thr Ile Val Ile Thr Pro His Ser Gly Glu Glu His
            210                 215                 220

Ala Val Gly Asn Asp Thr Gly Lys His Gly Lys Glu Ile Lys Ile Thr
225                 230                 235                 240

Pro Gln Ser Ser Ile Thr Glu Ala Glu Leu Thr Gly Tyr Gly Thr Val
                245                 250                 255

Thr Met Glu Cys Ser Pro Arg Thr Gly Leu Asp Phe Asn Glu Met Val
                260                 265                 270

Leu Leu Gln Met Glu Asn Lys Ala Trp Leu Val His Arg Gln Trp Phe
                275                 280                 285

Leu Asp Leu Pro Leu Pro Trp Leu Pro Gly Ala Asp Thr Gln Gly Ser
                290                 295                 300

Asn Trp Ile Gln Lys Glu Thr Leu Val Thr Phe Lys Asn Pro His Ala
305                 310                 315                 320

Lys Lys Gln Asp Val Val Val Leu Gly Ser Gln Glu Gly Ala Met His
                325                 330                 335

Thr Ala Leu Thr Gly Ala Thr Glu Ile Gln Met Ser Ser Gly Asn Leu
                340                 345                 350

Leu Phe Thr Gly His Leu Lys Cys Arg Leu Arg Met Asp Lys Leu Gln
                355                 360                 365

Leu Lys Gly Met Ser Tyr Ser Met Cys Thr Gly Lys Phe Lys Val Val
                370                 375                 380

Lys Glu Ile Ala Glu Thr Gln His Gly Thr Ile Val Ile Arg Val Gln
385                 390                 395                 400

Tyr Glu Gly Asp Gly Ser Pro Cys Lys Ile Pro Phe Glu Ile Met Asp
                405                 410                 415

Leu Glu Lys Arg His Val Leu Gly Arg Leu Ile Thr Val Asn Pro Ile
                420                 425                 430

Val Thr Glu Lys Asp Ser Pro Val Asn Ile Glu Ala Glu Pro Pro Phe
                435                 440                 445

Gly Asp Ser Tyr Ile Ile Ile Gly Val Glu Pro Gly Gln Leu Lys Leu
            450                 455                 460

Asn Trp Phe Lys Lys Gly Ser Ser Ile Gly Gln Met Ile Glu Thr Thr
465                 470                 475                 480

Met Arg Gly Ala Lys Arg Met Ala Ile Leu Gly Asp Thr Ala Trp Asp
                485                 490                 495

Phe Gly Ser Leu Gly Gly Val Phe Thr Ser Ile Gly Lys Ala Leu His
                500                 505                 510

Gln Val Phe Gly Ala Ile Tyr Gly Ala Ala Phe Ser Gly Val Ser Trp
                515                 520                 525

Thr Met Lys Ile Leu Ile Gly Val Ile Ile Thr Trp Ile Gly Met Asn
                530                 535                 540

Ser Arg Ser Thr Ser Leu Ser Val Ser Leu Val Leu Val Gly Val Val
545                 550                 555                 560

Thr Leu Tyr Leu Gly Val Met Val Gln Ala
                565                 570
```

<210> SEQ ID NO 19

-continued

<211> LENGTH: 661
<212> TYPE: PRT
<213> ORGANISM: Dengue virus
<400> SEQUENCE: 19

```
Phe His Leu Thr Thr Arg Asn Gly Glu Pro His Met Ile Val Ser Arg
1               5                   10                  15

Gln Glu Lys Gly Lys Ser Leu Leu Phe Lys Thr Glu Asp Gly Val Asn
            20                  25                  30

Met Cys Thr Leu Met Ala Met Asp Leu Gly Glu Leu Cys Glu Asp Thr
            35                  40                  45

Ile Thr Tyr Lys Cys Pro Phe Leu Arg Gln Asn Glu Pro Glu Asp Ile
    50                  55                  60

Asp Cys Trp Cys Asn Ser Thr Ser Thr Trp Val Thr Tyr Gly Thr Cys
65                  70                  75                  80

Thr Thr Thr Gly Glu His Arg Arg Glu Lys Arg Ser Val Ala Leu Val
                85                  90                  95

Pro His Val Gly Met Gly Leu Glu Thr Arg Thr Glu Thr Trp Met Ser
            100                 105                 110

Ser Glu Gly Ala Trp Lys His Ala Gln Arg Ile Glu Thr Trp Ile Leu
            115                 120                 125

Arg His Pro Gly Phe Thr Ile Met Ala Ala Ile Leu Ala Tyr Thr Ile
    130                 135                 140

Gly Thr Thr His Phe Gln Arg Ala Leu Ile Phe Ile Leu Leu Thr Ala
145                 150                 155                 160

Val Ala Pro Ser Met Thr Met Arg Cys Ile Gly Ile Ser Asn Arg Asp
                165                 170                 175

Phe Val Glu Gly Val Ser Gly Gly Ser Trp Val Asp Ile Val Leu Glu
            180                 185                 190

His Gly Ser Cys Val Thr Thr Met Ala Lys Asn Lys Pro Thr Leu Asp
            195                 200                 205

Phe Glu Leu Ile Lys Thr Glu Ala Lys Gln Pro Ala Thr Leu Arg Lys
    210                 215                 220

Tyr Cys Ile Glu Ala Lys Leu Thr Asn Thr Thr Thr Asp Ser Arg Cys
225                 230                 235                 240

Pro Thr Gln Gly Glu Pro Ser Leu Asn Glu Glu Gln Asp Lys Arg Phe
                245                 250                 255

Val Cys Lys His Ser Met Val Asp Arg Gly Trp Gly Asn Gly Cys Gly
            260                 265                 270

Leu Phe Gly Lys Gly Gly Ile Val Thr Cys Ala Met Phe Thr Cys Lys
            275                 280                 285

Lys Asn Met Lys Gly Lys Val Val Gln Pro Glu Asn Leu Glu Tyr Thr
    290                 295                 300

Ile Val Ile Thr Pro His Ser Gly Glu Glu His Ala Val Gly Asn Asp
305                 310                 315                 320

Thr Gly Lys His Gly Lys Glu Ile Lys Ile Thr Pro Gln Ser Ser Ile
                325                 330                 335

Thr Glu Ala Glu Leu Thr Gly Tyr Gly Thr Val Thr Met Glu Cys Ser
            340                 345                 350

Pro Arg Thr Gly Leu Asp Phe Asn Glu Met Val Leu Leu Gln Met Glu
            355                 360                 365

Asn Lys Ala Trp Leu Val His Arg Gln Trp Phe Leu Asp Leu Pro Leu
    370                 375                 380

Pro Trp Leu Pro Gly Ala Asp Thr Gln Gly Ser Asn Trp Ile Gln Lys
```

-continued

```
385               390               395               400

Glu Thr Leu Val Thr Phe Lys Asn Pro His Ala Lys Lys Gln Asp Val
            405               410               415

Val Val Leu Gly Ser Gln Glu Gly Ala Met His Thr Ala Leu Thr Gly
            420               425               430

Ala Thr Glu Ile Gln Met Ser Ser Gly Asn Leu Leu Phe Thr Gly His
            435               440               445

Leu Lys Cys Arg Leu Arg Met Asp Lys Leu Gln Leu Lys Gly Met Ser
        450               455               460

Tyr Ser Met Cys Thr Gly Lys Phe Lys Val Val Lys Glu Ile Ala Glu
465               470               475               480

Thr Gln His Gly Thr Ile Val Ile Arg Val Gln Tyr Glu Gly Asp Gly
                485               490               495

Ser Pro Cys Lys Ile Pro Phe Glu Ile Met Asp Leu Glu Lys Arg His
            500               505               510

Val Leu Gly Arg Leu Ile Thr Val Asn Pro Ile Val Thr Glu Lys Asp
            515               520               525

Ser Pro Val Asn Ile Glu Ala Glu Pro Pro Phe Gly Asp Ser Tyr Ile
        530               535               540

Ile Ile Gly Val Glu Pro Gly Gln Leu Lys Leu Asn Trp Phe Lys Lys
545               550               555               560

Gly Ser Ser Ile Gly Gln Met Ile Glu Thr Thr Met Arg Gly Ala Lys
                565               570               575

Arg Met Ala Ile Leu Gly Asp Thr Ala Trp Asp Phe Gly Ser Leu Gly
            580               585               590

Gly Val Phe Thr Ser Ile Gly Lys Ala Leu His Gln Val Phe Gly Ala
            595               600               605

Ile Tyr Gly Ala Ala Phe Ser Gly Val Ser Trp Thr Met Lys Ile Leu
        610               615               620

Ile Gly Val Ile Ile Thr Trp Ile Gly Met Asn Ser Arg Ser Thr Ser
625               630               635               640

Leu Ser Val Ser Leu Val Leu Val Gly Val Val Thr Leu Tyr Leu Gly
                645               650               655

Val Met Val Gln Ala
                660
```

<210> SEQ ID NO 20
<211> LENGTH: 31
<212> TYPE: DNA
<213> ORGANISM: Artificial Sequence
<220> FEATURE:
<223> OTHER INFORMATION: Synthetic construct

<400> SEQUENCE: 20
aaacgggccc tctagagcca ccatgctcaa c                                    31

<210> SEQ ID NO 21
<211> LENGTH: 42
<212> TYPE: DNA
<213> ORGANISM: Artificial Sequence
<220> FEATURE:
<223> OTHER INFORMATION: Synthetic construct

<400> SEQUENCE: 21
tttaacttaa gcttggtacc ttaagcttgc accatgactc cc                        42

<210> SEQ ID NO 22

<211> LENGTH: 73
<212> TYPE: DNA
<213> ORGANISM: Artificial Sequence
<220> FEATURE:
<223> OTHER INFORMATION: Synthetic construct

<400> SEQUENCE: 22
aaacgggccc tctagagcca ccatgctcaa cattttaaac agaaggagga gaaccgccgg        60
aatgatcatc atg                                                          73

<210> SEQ ID NO 23
<211> LENGTH: 71
<212> TYPE: DNA
<213> ORGANISM: Artificial Sequence
<220> FEATURE:
<223> OTHER INFORMATION: Synthetic construct

<400> SEQUENCE: 23
ggagaaccgc cggaatgatc atcatgctga tccccaccgt gatggccagc gtggctctgg        60
tgccccatgt c                                                            71

<210> SEQ ID NO 24
<211> LENGTH: 73
<212> TYPE: DNA
<213> ORGANISM: Artificial Sequence
<220> FEATURE:
<223> OTHER INFORMATION: Synthetic construct

<400> SEQUENCE: 24
aaacgggccc tctagagcca ccatgctcaa cattttaaac agaaggagga gaaccgccgg        60
aatgatcatc atg                                                          73

<210> SEQ ID NO 25
<211> LENGTH: 59
<212> TYPE: DNA
<213> ORGANISM: Artificial Sequence
<220> FEATURE:
<223> OTHER INFORMATION: Synthetic construct

<400> SEQUENCE: 25
gtgaacagag gctggggcac aggatgcttc gaatggggaa agggaggcat cgtgacttg         59

<210> SEQ ID NO 26
<211> LENGTH: 59
<212> TYPE: DNA
<213> ORGANISM: Artificial Sequence
<220> FEATURE:
<223> OTHER INFORMATION: Synthetic construct

<400> SEQUENCE: 26
tccccattcg aagcatcctg tgcccagcc tctgttcacc atggagtgct tgcacacga          59

<210> SEQ ID NO 27
<211> LENGTH: 59
<212> TYPE: DNA
<213> ORGANISM: Artificial Sequence
<220> FEATURE:
<223> OTHER INFORMATION: Synthetic construct

<400> SEQUENCE: 27
gtgaacagag gctggggcac aggatgcttc aagtggggaa agggaggcat cgtgacttg         59

<210> SEQ ID NO 28
<211> LENGTH: 59

```
<212> TYPE: DNA
<213> ORGANISM: Artificial Sequence
<220> FEATURE:
<223> OTHER INFORMATION: Synthetic construct

<400> SEQUENCE: 28
tccccacttg aagcatcctg tgccccagcc tctgttcacc atggagtgct tgcacacga       59

<210> SEQ ID NO 29
<211> LENGTH: 59
<212> TYPE: DNA
<213> ORGANISM: Artificial Sequence
<220> FEATURE:
<223> OTHER INFORMATION: Synthetic construct

<400> SEQUENCE: 29
gtgaacagag gatggggcac aggatgcctg gaatggggca agggctcttt aatcacttg       59

<210> SEQ ID NO 30
<211> LENGTH: 59
<212> TYPE: DNA
<213> ORGANISM: Artificial Sequence
<220> FEATURE:
<223> OTHER INFORMATION: Synthetic construct

<400> SEQUENCE: 30
gccccattcc aggcatcctg tgccccatcc tctgttcacg aaggtcctac gacacacga       59

<210> SEQ ID NO 31
<211> LENGTH: 579
<212> TYPE: PRT
<213> ORGANISM: zika virus

<400> SEQUENCE: 31

Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser Ile Arg Cys Ile Gly
65                  70                  75                  80

Val Ser Asn Arg Asp Phe Val Glu Gly Met Ser Gly Gly Thr Trp Val
                85                  90                  95

Asp Val Val Leu Glu His Gly Gly Cys Val Thr Val Met Ala Gln Asp
            100                 105                 110

Lys Pro Thr Val Asp Ile Glu Leu Val Thr Thr Thr Val Ser Asn Met
        115                 120                 125

Ala Glu Val Arg Ser Tyr Cys Tyr Glu Ala Ser Ile Ser Asp Met Ala
    130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
            180                 185                 190

Lys Phe Ala Cys Ser Lys Lys Met Thr Gly Lys Ser Ile Gln Pro Glu
        195                 200                 205
```

```
Asn Leu Glu Tyr Arg Ile Met Leu Ser Val His Gly Ser Gln His Ser
    210             215             220
Gly Met Ile Val Asn Asp Thr Gly His Glu Thr Asp Glu Asn Arg Ala
225             230             235             240
Lys Val Glu Ile Thr Pro Asn Ser Pro Arg Ala Glu Ala Thr Leu Gly
            245             250             255
Gly Phe Gly Ser Leu Gly Leu Asp Cys Glu Pro Arg Thr Gly Leu Asp
            260             265             270
Phe Ser Asp Leu Tyr Tyr Leu Thr Met Asn Asn Lys His Trp Leu Val
            275             280             285
His Lys Glu Trp Phe His Asp Ile Pro Leu Pro Trp His Ala Gly Ala
    290             295             300
Asp Thr Gly Thr Pro His Trp Asn Asn Lys Glu Ala Leu Val Glu Phe
305             310             315             320
Lys Asp Ala His Ala Lys Arg Gln Thr Val Val Leu Gly Ser Gln
            325             330             335
Glu Gly Ala Val His Thr Ala Leu Ala Gly Ala Leu Glu Ala Glu Met
            340             345             350
Asp Gly Ala Lys Gly Arg Leu Ser Ser Gly His Leu Lys Cys Arg Leu
            355             360             365
Lys Met Asp Lys Leu Arg Leu Lys Gly Val Ser Tyr Ser Leu Cys Thr
    370             375             380
Ala Ala Phe Thr Phe Thr Lys Ile Pro Ala Glu Thr Leu His Gly Thr
385             390             395             400
Val Thr Val Glu Val Gln Tyr Ala Gly Thr Asp Gly Pro Cys Lys Val
            405             410             415
Pro Ala Gln Met Ala Val Asp Met Gln Thr Leu Thr Pro Val Gly Arg
            420             425             430
Leu Ile Thr Ala Asn Pro Val Ile Thr Glu Ser Thr Glu Asn Ser Lys
            435             440             445
Met Met Leu Glu Leu Asp Pro Pro Phe Gly Asp Ser Tyr Ile Val Ile
    450             455             460
Gly Val Gly Glu Lys Lys Ile Thr His His Trp His Arg Ser Gly Ser
465             470             475             480
Thr Ile Gly Lys Ala Phe Glu Ala Thr Val Arg Gly Ala Lys Arg Met
            485             490             495
Ala Val Leu Gly Asp Thr Ala Trp Asp Phe Gly Ser Val Gly Gly Ala
            500             505             510
Leu Asn Ser Leu Gly Lys Gly Ile His Gln Ile Phe Gly Ala Ala Phe
            515             520             525
Lys Ser Leu Phe Gly Gly Met Ser Trp Phe Ser Gln Ile Leu Ile Gly
    530             535             540
Thr Leu Leu Val Trp Leu Gly Leu Asn Thr Lys Asn Gly Ser Ile Ser
545             550             555             560
Leu Met Cys Leu Ala Leu Gly Gly Val Leu Ile Phe Leu Ser Thr Ala
            565             570             575
Val Ser Ala
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic construct
```

<400> SEQUENCE: 32
ttttggcaaa gaattcgccg                                                         20

<210> SEQ ID NO 33
<211> LENGTH: 41
<212> TYPE: DNA
<213> ORGANISM: Artificial Sequence
<220> FEATURE:
<223> OTHER INFORMATION: Synthetic construct

<400> SEQUENCE: 33
gatctgctag ctcgagtcaa gcgctcacag ctgtggacag a                                 41

<210> SEQ ID NO 34
<211> LENGTH: 36
<212> TYPE: DNA
<213> ORGANISM: Artificial Sequence
<220> FEATURE:
<223> OTHER INFORMATION: Synthetic construct

<400> SEQUENCE: 34
cgcagccatt tccggcgccc ctgtccacca gggtcc                                       36

<210> SEQ ID NO 35
<211> LENGTH: 38
<212> TYPE: DNA
<213> ORGANISM: Artificial Sequence
<220> FEATURE:
<223> OTHER INFORMATION: Synthetic construct

<400> SEQUENCE: 35
ggtggacagg ggcgccggaa atggctgcgg cctgtttg                                     38

<210> SEQ ID NO 36
<211> LENGTH: 36
<212> TYPE: DNA
<213> ORGANISM: Artificial Sequence
<220> FEATURE:
<223> OTHER INFORMATION: Synthetic construct

<400> SEQUENCE: 36
cgcagccatt tccccggccc ctgtccacca gggtcc                                       36

<210> SEQ ID NO 37
<211> LENGTH: 38
<212> TYPE: DNA
<213> ORGANISM: Artificial Sequence
<220> FEATURE:
<223> OTHER INFORMATION: Synthetic construct

<400> SEQUENCE: 37
ggtggacagg ggccggggaa atggctgcgg cctgtttg                                     38

<210> SEQ ID NO 38
<211> LENGTH: 36
<212> TYPE: DNA
<213> ORGANISM: Artificial Sequence
<220> FEATURE:
<223> OTHER INFORMATION: Synthetic construct

<400> SEQUENCE: 38
cgcagccatt tccgttgccc ctgtccacca gggtcc                                       36

<210> SEQ ID NO 39

```
<211> LENGTH: 38
<212> TYPE: DNA
<213> ORGANISM: Artificial Sequence
<220> FEATURE:
<223> OTHER INFORMATION: Synthetic construct

<400> SEQUENCE: 39
ggtggacagg ggcaacggaa atggctgcgg cctgtttg                        38

<210> SEQ ID NO 40
<211> LENGTH: 36
<212> TYPE: DNA
<213> ORGANISM: Artificial Sequence
<220> FEATURE:
<223> OTHER INFORMATION: Synthetic construct

<400> SEQUENCE: 40
cgcagccatt tccgtcgccc ctgtccacca gggtcc                          36

<210> SEQ ID NO 41
<211> LENGTH: 38
<212> TYPE: DNA
<213> ORGANISM: Artificial Sequence
<220> FEATURE:
<223> OTHER INFORMATION: Synthetic construct

<400> SEQUENCE: 41
ggtggacagg ggcgacggaa atggctgcgg cctgtttg                        38

<210> SEQ ID NO 42
<211> LENGTH: 36
<212> TYPE: DNA
<213> ORGANISM: Artificial Sequence
<220> FEATURE:
<223> OTHER INFORMATION: Synthetic construct

<400> SEQUENCE: 42
cgcagccatt tccgcagccc ctgtccacca gggtcc                          36

<210> SEQ ID NO 43
<211> LENGTH: 38
<212> TYPE: DNA
<213> ORGANISM: Artificial Sequence
<220> FEATURE:
<223> OTHER INFORMATION: Synthetic construct

<400> SEQUENCE: 43
ggtggacagg ggctgcggaa atggctgcgg cctgtttg                        38

<210> SEQ ID NO 44
<211> LENGTH: 36
<212> TYPE: DNA
<213> ORGANISM: Artificial Sequence
<220> FEATURE:
<223> OTHER INFORMATION: Synthetic construct

<400> SEQUENCE: 44
cgcagccatt tccctggccc ctgtccacca gggtcc                          36

<210> SEQ ID NO 45
<211> LENGTH: 38
<212> TYPE: DNA
<213> ORGANISM: Artificial Sequence
<220> FEATURE:
<223> OTHER INFORMATION: Synthetic construct

<400> SEQUENCE: 45
```

-continued

```
ggtggacagg ggccagggaa atggctgcgg cctgtttg                        38

<210> SEQ ID NO 46
<211> LENGTH: 36
<212> TYPE: DNA
<213> ORGANISM: Artificial Sequence
<220> FEATURE:
<223> OTHER INFORMATION: Synthetic construct

<400> SEQUENCE: 46
cgcagccatt tccctcgccc ctgtccacca gggtcc                          36

<210> SEQ ID NO 47
<211> LENGTH: 38
<212> TYPE: DNA
<213> ORGANISM: Artificial Sequence
<220> FEATURE:
<223> OTHER INFORMATION: Synthetic construct

<400> SEQUENCE: 47
ggtggacagg ggcgagggaa atggctgcgg cctgtttg                        38

<210> SEQ ID NO 48
<211> LENGTH: 36
<212> TYPE: DNA
<213> ORGANISM: Artificial Sequence
<220> FEATURE:
<223> OTHER INFORMATION: Synthetic construct

<400> SEQUENCE: 48
cgcagccatt tccgccgccc ctgtccacca gggtcc                          36

<210> SEQ ID NO 49
<211> LENGTH: 38
<212> TYPE: DNA
<213> ORGANISM: Artificial Sequence
<220> FEATURE:
<223> OTHER INFORMATION: Synthetic construct

<400> SEQUENCE: 49
ggtggacagg ggcggcggaa atggctgcgg cctgtttg                        38

<210> SEQ ID NO 50
<211> LENGTH: 36
<212> TYPE: DNA
<213> ORGANISM: Artificial Sequence
<220> FEATURE:
<223> OTHER INFORMATION: Synthetic construct

<400> SEQUENCE: 50
cgcagccatt tccgtggccc ctgtccacca gggtcc                          36

<210> SEQ ID NO 51
<211> LENGTH: 38
<212> TYPE: DNA
<213> ORGANISM: Artificial Sequence
<220> FEATURE:
<223> OTHER INFORMATION: Synthetic construct

<400> SEQUENCE: 51
ggtggacagg ggccacggaa atggctgcgg cctgtttg                        38

<210> SEQ ID NO 52
<211> LENGTH: 36
<212> TYPE: DNA
```

-continued

<213> ORGANISM: Artificial Sequence
<220> FEATURE:
<223> OTHER INFORMATION: Synthetic construct

<400> SEQUENCE: 52
cgcagccatt tccgatgccc ctgtccacca gggtcc                                36

<210> SEQ ID NO 53
<211> LENGTH: 38
<212> TYPE: DNA
<213> ORGANISM: Artificial Sequence
<220> FEATURE:
<223> OTHER INFORMATION: Synthetic construct

<400> SEQUENCE: 53
ggtggacagg ggcatcggaa atggctgcgg cctgtttg                              38

<210> SEQ ID NO 54
<211> LENGTH: 36
<212> TYPE: DNA
<213> ORGANISM: Artificial Sequence
<220> FEATURE:
<223> OTHER INFORMATION: Synthetic construct

<400> SEQUENCE: 54
cgcagccatt tcccaggccc ctgtccacca gggtcc                                36

<210> SEQ ID NO 55
<211> LENGTH: 38
<212> TYPE: DNA
<213> ORGANISM: Artificial Sequence
<220> FEATURE:
<223> OTHER INFORMATION: Synthetic construct

<400> SEQUENCE: 55
ggtggacagg ggcctgggaa atggctgcgg cctgtttg                              38

<210> SEQ ID NO 56
<211> LENGTH: 36
<212> TYPE: DNA
<213> ORGANISM: Artificial Sequence
<220> FEATURE:
<223> OTHER INFORMATION: Synthetic construct

<400> SEQUENCE: 56
cgcagccatt tcccttgccc ctgtccacca gggtcc                                36

<210> SEQ ID NO 57
<211> LENGTH: 38
<212> TYPE: DNA
<213> ORGANISM: Artificial Sequence
<220> FEATURE:
<223> OTHER INFORMATION: Synthetic construct

<400> SEQUENCE: 57
ggtggacagg ggcaagggaa atggctgcgg cctgtttg                              38

<210> SEQ ID NO 58
<211> LENGTH: 36
<212> TYPE: DNA
<213> ORGANISM: Artificial Sequence
<220> FEATURE:
<223> OTHER INFORMATION: Synthetic construct

<400> SEQUENCE: 58
cgcagccatt tcccatgccc ctgtccacca gggtcc                                36

```
<210> SEQ ID NO 59
<211> LENGTH: 38
<212> TYPE: DNA
<213> ORGANISM: Artificial Sequence
<220> FEATURE:
<223> OTHER INFORMATION: Synthetic construct

<400> SEQUENCE: 59
ggtggacagg ggcatgggaa atggctgcgg cctgtttg                              38

<210> SEQ ID NO 60
<211> LENGTH: 36
<212> TYPE: DNA
<213> ORGANISM: Artificial Sequence
<220> FEATURE:
<223> OTHER INFORMATION: Synthetic construct

<400> SEQUENCE: 60
cgcagccatt tccgaagccc ctgtccacca gggtcc                               36

<210> SEQ ID NO 61
<211> LENGTH: 38
<212> TYPE: DNA
<213> ORGANISM: Artificial Sequence
<220> FEATURE:
<223> OTHER INFORMATION: Synthetic construct

<400> SEQUENCE: 61
ggtggacagg ggcttcggaa atggctgcgg cctgtttg                              38

<210> SEQ ID NO 62
<211> LENGTH: 36
<212> TYPE: DNA
<213> ORGANISM: Artificial Sequence
<220> FEATURE:
<223> OTHER INFORMATION: Synthetic construct

<400> SEQUENCE: 62
cgcagccatt tccggggccc ctgtccacca gggtcc                               36

<210> SEQ ID NO 63
<211> LENGTH: 38
<212> TYPE: DNA
<213> ORGANISM: Artificial Sequence
<220> FEATURE:
<223> OTHER INFORMATION: Synthetic construct

<400> SEQUENCE: 63
ggtggacagg ggccccggaa atggctgcgg cctgtttg                              38

<210> SEQ ID NO 64
<211> LENGTH: 36
<212> TYPE: DNA
<213> ORGANISM: Artificial Sequence
<220> FEATURE:
<223> OTHER INFORMATION: Synthetic construct

<400> SEQUENCE: 64
cgcagccatt tccgctgccc ctgtccacca gggtcc                               36

<210> SEQ ID NO 65
<211> LENGTH: 38
<212> TYPE: DNA
<213> ORGANISM: Artificial Sequence
<220> FEATURE:
```

-continued

<223> OTHER INFORMATION: Synthetic construct

<400> SEQUENCE: 65
ggtggacagg ggcagcggaa atggctgcgg cctgtttg                                    38

<210> SEQ ID NO 66
<211> LENGTH: 36
<212> TYPE: DNA
<213> ORGANISM: Artificial Sequence
<220> FEATURE:
<223> OTHER INFORMATION: Synthetic construct

<400> SEQUENCE: 66
cgcagccatt tccggtgccc ctgtccacca gggtcc                                      36

<210> SEQ ID NO 67
<211> LENGTH: 38
<212> TYPE: DNA
<213> ORGANISM: Artificial Sequence
<220> FEATURE:
<223> OTHER INFORMATION: Synthetic construct

<400> SEQUENCE: 67
ggtggacagg ggcaccggaa atggctgcgg cctgtttg                                    38

<210> SEQ ID NO 68
<211> LENGTH: 36
<212> TYPE: DNA
<213> ORGANISM: Artificial Sequence
<220> FEATURE:
<223> OTHER INFORMATION: Synthetic construct

<400> SEQUENCE: 68
cgcagccatt tccgtagccc ctgtccacca gggtcc                                      36

<210> SEQ ID NO 69
<211> LENGTH: 38
<212> TYPE: DNA
<213> ORGANISM: Artificial Sequence
<220> FEATURE:
<223> OTHER INFORMATION: Synthetic construct

<400> SEQUENCE: 69
ggtggacagg ggctacggaa atggctgcgg cctgtttg                                    38

<210> SEQ ID NO 70
<211> LENGTH: 36
<212> TYPE: DNA
<213> ORGANISM: Artificial Sequence
<220> FEATURE:
<223> OTHER INFORMATION: Synthetic construct

<400> SEQUENCE: 70
cgcagccatt tcccacgccc ctgtccacca gggtcc                                      36

<210> SEQ ID NO 71
<211> LENGTH: 38
<212> TYPE: DNA
<213> ORGANISM: Artificial Sequence
<220> FEATURE:
<223> OTHER INFORMATION: Synthetic construct

<400> SEQUENCE: 71
ggtggacagg ggcgtgggaa atggctgcgg cctgtttg                                    38

<210> SEQ ID NO 72
<211> LENGTH: 32
<212> TYPE: DNA
<213> ORGANISM: Artificial sequence
<220> FEATURE:
<223> OTHER INFORMATION: Synthetic construct

<400> SEQUENCE: 72
ctgctgtttg gaaagggctc cctggtgacc tg                                          32

<210> SEQ ID NO 73
<211> LENGTH: 32
<212> TYPE: DNA
<213> ORGANISM: Artificial Sequence
<220> FEATURE:
<223> OTHER INFORMATION: Synthetic construct

<400> SEQUENCE: 73
aaacagcagg cagccatttc cccagcccct gt                                          32

<210> SEQ ID NO 74
<211> LENGTH: 32
<212> TYPE: DNA
<213> ORGANISM: Artificial Sequence
<220> FEATURE:
<223> OTHER INFORMATION: Synthetic construct

<400> SEQUENCE: 74
ttcctgtttg gaaagggctc cctggtgacc tg                                          32

<210> SEQ ID NO 75
<211> LENGTH: 32
<212> TYPE: DNA
<213> ORGANISM: Artificial Sequence
<220> FEATURE:
<223> OTHER INFORMATION: Synthetic construct

<400> SEQUENCE: 75
aaacaggaag cagccatttc cccagcccct gt                                          32

<210> SEQ ID NO 76
<211> LENGTH: 32
<212> TYPE: DNA
<213> ORGANISM: Artificial Sequence
<220> FEATURE:
<223> OTHER INFORMATION: Synthetic construct

<400> SEQUENCE: 76
tggctgtttg gaaagggctc cctggtgacc tg                                          32

<210> SEQ ID NO 77
<211> LENGTH: 32
<212> TYPE: DNA
<213> ORGANISM: Artificial Sequence
<220> FEATURE:
<223> OTHER INFORMATION: Synthetic construct

<400> SEQUENCE: 77
aaacagccag cagccatttc cccagcccct gt                                          32

<210> SEQ ID NO 78
<211> LENGTH: 32
<212> TYPE: DNA
<213> ORGANISM: Artificial Sequence
<220> FEATURE:
<223> OTHER INFORMATION: Synthetic construct

<400> SEQUENCE: 78
tacctgtttg gaaagggctc cctggtgacc tg                                    32

<210> SEQ ID NO 79
<211> LENGTH: 32
<212> TYPE: DNA
<213> ORGANISM: Artificial Sequence
<220> FEATURE:
<223> OTHER INFORMATION: Synthetic construct

<400> SEQUENCE: 79
aaacaggtag cagccatttc cccagcccct gt                                    32

<210> SEQ ID NO 80
<211> LENGTH: 32
<212> TYPE: DNA
<213> ORGANISM: Artificial Sequence
<220> FEATURE:
<223> OTHER INFORMATION: Synthetic construct

<400> SEQUENCE: 80
atcctgtttg gaaagggctc cctggtgacc tg                                    32

<210> SEQ ID NO 81
<211> LENGTH: 32
<212> TYPE: DNA
<213> ORGANISM: Artificial Sequence
<220> FEATURE:
<223> OTHER INFORMATION: Synthetic construct

<400> SEQUENCE: 81
aaacaggatg cagccatttc cccagcccct gt                                    32

<210> SEQ ID NO 82
<211> LENGTH: 32
<212> TYPE: DNA
<213> ORGANISM: Artificial Sequence
<220> FEATURE:
<223> OTHER INFORMATION: Synthetic construct

<400> SEQUENCE: 82
ggcgagtttg gaaagggctc cctggtgacc tg                                    32

<210> SEQ ID NO 83
<211> LENGTH: 32
<212> TYPE: DNA
<213> ORGANISM: Artificial Sequence
<220> FEATURE:
<223> OTHER INFORMATION: Synthetic construct

<400> SEQUENCE: 83
aaactcgccg cagccatttc cccagcccct gt                                    32

<210> SEQ ID NO 84
<211> LENGTH: 32
<212> TYPE: DNA
<213> ORGANISM: Artificial Sequence
<220> FEATURE:
<223> OTHER INFORMATION: Synthetic construct

<400> SEQUENCE: 84
ggcaagtttg gaaagggctc cctggtgacc tg                                    32

<210> SEQ ID NO 85
<211> LENGTH: 32

```
<212> TYPE: DNA
<213> ORGANISM: Artificial Sequence
<220> FEATURE:
<223> OTHER INFORMATION: Synthetic construct

<400> SEQUENCE: 85
aaacttgccg cagccatttc cccagcccct gt                                   32

<210> SEQ ID NO 86
<211> LENGTH: 32
<212> TYPE: DNA
<213> ORGANISM: Artificial Sequence
<220> FEATURE:
<223> OTHER INFORMATION: Synthetic construct

<400> SEQUENCE: 86
ggccggtttg gaaagggctc cctggtgacc tg                                   32

<210> SEQ ID NO 87
<211> LENGTH: 32
<212> TYPE: DNA
<213> ORGANISM: Artificial Sequence
<220> FEATURE:
<223> OTHER INFORMATION: Synthetic construct

<400> SEQUENCE: 87
aaaccggccg cagccatttc cccagcccct gt                                   32

<210> SEQ ID NO 88
<211> LENGTH: 32
<212> TYPE: DNA
<213> ORGANISM: Artificial Sequence
<220> FEATURE:
<223> OTHER INFORMATION: Synthetic construct

<400> SEQUENCE: 88
ggcgactttg gaaagggctc cctggtgacc tg                                   32

<210> SEQ ID NO 89
<211> LENGTH: 32
<212> TYPE: DNA
<213> ORGANISM: Artificial Sequence
<220> FEATURE:
<223> OTHER INFORMATION: Synthetic construct

<400> SEQUENCE: 89
aaagtcgccg cagccatttc cccagcccct gt                                   32

<210> SEQ ID NO 90
<211> LENGTH: 32
<212> TYPE: DNA
<213> ORGANISM: Artificial Sequence
<220> FEATURE:
<223> OTHER INFORMATION: Synthetic construct

<400> SEQUENCE: 90
ggcacctttg gaaagggctc cctggtgacc tg                                   32

<210> SEQ ID NO 91
<211> LENGTH: 32
<212> TYPE: DNA
<213> ORGANISM: Artificial Sequence
<220> FEATURE:
<223> OTHER INFORMATION: Synthetic construct

<400> SEQUENCE: 91
```
aaaggtgccg cagccatttc cccagccccct gt                                    32

<210> SEQ ID NO 92
<211> LENGTH: 32
<212> TYPE: DNA
<213> ORGANISM: Artificial Sequence
<220> FEATURE:
<223> OTHER INFORMATION: Synthetic construct

<400> SEQUENCE: 92
ggcctgtggg gaaagggctc cctggtgacc tg                                    32

<210> SEQ ID NO 93
<211> LENGTH: 32
<212> TYPE: DNA
<213> ORGANISM: Artificial Sequence
<220> FEATURE:
<223> OTHER INFORMATION: Synthetic construct

<400> SEQUENCE: 93
ccacaggccg cagccatttc cccagccccct gt                                    32

<210> SEQ ID NO 94
<211> LENGTH: 32
<212> TYPE: DNA
<213> ORGANISM: Artificial Sequence
<220> FEATURE:
<223> OTHER INFORMATION: Synthetic construct

<400> SEQUENCE: 94
ggcctgcacg gaaagggctc cctggtgacc tg                                    32

<210> SEQ ID NO 95
<211> LENGTH: 32
<212> TYPE: DNA
<213> ORGANISM: Artificial Sequence
<220> FEATURE:
<223> OTHER INFORMATION: Synthetic construct

<400> SEQUENCE: 95
gtgcaggccg cagccatttc cccagccccct gt                                    32

<210> SEQ ID NO 96
<211> LENGTH: 32
<212> TYPE: DNA
<213> ORGANISM: Artificial Sequence
<220> FEATURE:
<223> OTHER INFORMATION: Synthetic construct

<400> SEQUENCE: 96
ggcctgtacg gaaagggctc cctggtgacc tg                                    32

<210> SEQ ID NO 97
<211> LENGTH: 32
<212> TYPE: DNA
<213> ORGANISM: Artificial Sequence
<220> FEATURE:
<223> OTHER INFORMATION: Synthetic construct

<400> SEQUENCE: 97
gtacaggccg cagccatttc cccagccccct gt                                    32

<210> SEQ ID NO 98
<211> LENGTH: 32
<212> TYPE: DNA
<213> ORGANISM: Artificial Sequence -continued
<220> FEATURE:
<223> OTHER INFORMATION: Synthetic construct

<400> SEQUENCE: 98
ggcctgcccg gaaagggctc cctggtgacc tg                          32

<210> SEQ ID NO 99
<211> LENGTH: 32
<212> TYPE: DNA
<213> ORGANISM: Artificial Sequence
<220> FEATURE:
<223> OTHER INFORMATION: Synthetic construct

<400> SEQUENCE: 99
gggcaggccg cagccatttc cccagcccct gt                          32

<210> SEQ ID NO 100
<211> LENGTH: 32
<212> TYPE: DNA
<213> ORGANISM: Artificial Sequence
<220> FEATURE:
<223> OTHER INFORMATION: Synthetic construct

<400> SEQUENCE: 100
ggcctggccg gaaagggctc cctggtgacc tg                          32

<210> SEQ ID NO 101
<211> LENGTH: 32
<212> TYPE: DNA
<213> ORGANISM: Artificial Sequence
<220> FEATURE:
<223> OTHER INFORMATION: Synthetic construct

<400> SEQUENCE: 101
ggccaggccg cagccatttc cccagcccct gt                          32

<210> SEQ ID NO 102
<211> LENGTH: 32
<212> TYPE: DNA
<213> ORGANISM: Artificial Sequence
<220> FEATURE:
<223> OTHER INFORMATION: Synthetic construct

<400> SEQUENCE: 102
ctggagtttg gaaagggctc cctggtgacc tg                          32

<210> SEQ ID NO 103
<211> LENGTH: 32
<212> TYPE: DNA
<213> ORGANISM: Artificial Sequence
<220> FEATURE:
<223> OTHER INFORMATION: Synthetic construct

<400> SEQUENCE: 103
aaactccagg cagccatttc cccagcccct gt                          32

<210> SEQ ID NO 104
<211> LENGTH: 32
<212> TYPE: DNA
<213> ORGANISM: Artificial Sequence
<220> FEATURE:
<223> OTHER INFORMATION: Synthetic construct

<400> SEQUENCE: 104
ctgaagtttg gaaagggctc cctggtgacc tg                          32

-continued

```
<210> SEQ ID NO 105
<211> LENGTH: 32
<212> TYPE: DNA
<213> ORGANISM: Artificial Sequence
<220> FEATURE:
<223> OTHER INFORMATION: Synthetic construct

<400> SEQUENCE: 105
aaacttcagg cagccatttc cccagcccct gt                                      32

<210> SEQ ID NO 106
<211> LENGTH: 32
<212> TYPE: DNA
<213> ORGANISM: Artificial Sequence
<220> FEATURE:
<223> OTHER INFORMATION: Synthetic construct

<400> SEQUENCE: 106
ttcgagtttg gaaagggctc cctggtgacc tg                                      32

<210> SEQ ID NO 107
<211> LENGTH: 32
<212> TYPE: DNA
<213> ORGANISM: Artificial Sequence
<220> FEATURE:
<223> OTHER INFORMATION: Synthetic construct

<400> SEQUENCE: 107
aaactcgaag cagccatttc cccagcccct gt                                      32

<210> SEQ ID NO 108
<211> LENGTH: 32
<212> TYPE: DNA
<213> ORGANISM: Artificial Sequence
<220> FEATURE:
<223> OTHER INFORMATION: Synthetic construct

<400> SEQUENCE: 108
ttcaagtttg gaaagggctc cctggtgacc tg                                      32

<210> SEQ ID NO 109
<211> LENGTH: 32
<212> TYPE: DNA
<213> ORGANISM: Artificial sequence
<220> FEATURE:
<223> OTHER INFORMATION: Synthetic construct

<400> SEQUENCE: 109
aaacttgaag cagccatttc cccagcccct gt                                      32

<210> SEQ ID NO 110
<211> LENGTH: 32
<212> TYPE: DNA
<213> ORGANISM: Artificial Sequence
<220> FEATURE:
<223> OTHER INFORMATION: Synthetic construct

<400> SEQUENCE: 110
ttccggtttg gaaagggctc cctggtgacc tg                                      32

<210> SEQ ID NO 111
<211> LENGTH: 32
<212> TYPE: DNA
<213> ORGANISM: Artificial Sequence
<220> FEATURE:
<223> OTHER INFORMATION: Synthetic construct
```

-continued

```
<400> SEQUENCE: 111
aaaccggaag cagccatttc cccagccccct gt                                    32

<210> SEQ ID NO 112
<211> LENGTH: 32
<212> TYPE: DNA
<213> ORGANISM: Artificial Sequence
<220> FEATURE:
<223> OTHER INFORMATION: Synthetic construct

<400> SEQUENCE: 112
ttcctgtggg gaaagggctc cctggtgacc tg                                     32

<210> SEQ ID NO 113
<211> LENGTH: 32
<212> TYPE: DNA
<213> ORGANISM: Artificial Sequence
<220> FEATURE:
<223> OTHER INFORMATION: Synthetic construct

<400> SEQUENCE: 113
ccacaggaag cagccatttc cccagccccct gt                                    32

<210> SEQ ID NO 114
<211> LENGTH: 32
<212> TYPE: DNA
<213> ORGANISM: Artificial Sequence
<220> FEATURE:
<223> OTHER INFORMATION: Synthetic construct

<400> SEQUENCE: 114
ctgctgtggg gaaagggctc cctggtgacc tg                                     32

<210> SEQ ID NO 115
<211> LENGTH: 32
<212> TYPE: DNA
<213> ORGANISM: Artificial Sequence
<220> FEATURE:
<223> OTHER INFORMATION: Synthetic construct

<400> SEQUENCE: 115
ccacagcagg cagccatttc cccagccccct gt                                    32

<210> SEQ ID NO 116
<211> LENGTH: 32
<212> TYPE: DNA
<213> ORGANISM: Artificial Sequence
<220> FEATURE:
<223> OTHER INFORMATION: Synthetic construct

<400> SEQUENCE: 116
ttcctgcacg gaaagggctc cctggtgacc tg                                     32

<210> SEQ ID NO 117
<211> LENGTH: 32
<212> TYPE: DNA
<213> ORGANISM: Artificial Sequence
<220> FEATURE:
<223> OTHER INFORMATION: Synthetic construct

<400> SEQUENCE: 117
gtgcaggaag cagccatttc cccagccccct gt                                    32

<210> SEQ ID NO 118
```

```
<211> LENGTH: 32
<212> TYPE: DNA
<213> ORGANISM: Artificial Sequence
<220> FEATURE:
<223> OTHER INFORMATION: Synthetic construct

<400> SEQUENCE: 118
tacctgtggg gaaagggctc cctggtgacc tg                               32

<210> SEQ ID NO 119
<211> LENGTH: 32
<212> TYPE: DNA
<213> ORGANISM: Artificial Sequence
<220> FEATURE:
<223> OTHER INFORMATION: Synthetic construct

<400> SEQUENCE: 119
ccacaggtag cagccatttc cccagcccct gt                               32

<210> SEQ ID NO 120
<211> LENGTH: 32
<212> TYPE: DNA
<213> ORGANISM: Artificial Sequence
<220> FEATURE:
<223> OTHER INFORMATION: Synthetic construct

<400> SEQUENCE: 120
tggctgtacg gaaagggctc cctggtgacc tg                               32

<210> SEQ ID NO 121
<211> LENGTH: 32
<212> TYPE: DNA
<213> ORGANISM: Artificial Sequence
<220> FEATURE:
<223> OTHER INFORMATION: Synthetic construct

<400> SEQUENCE: 121
gtacagccag cagccatttc cccagcccct gt                               32

<210> SEQ ID NO 122
<211> LENGTH: 32
<212> TYPE: DNA
<213> ORGANISM: Artificial Sequence
<220> FEATURE:
<223> OTHER INFORMATION: Synthetic construct

<400> SEQUENCE: 122
ggcgagtggg gaaagggctc cctggtgacc tg                               32

<210> SEQ ID NO 123
<211> LENGTH: 32
<212> TYPE: DNA
<213> ORGANISM: Artificial Sequence
<220> FEATURE:
<223> OTHER INFORMATION: Synthetic construct

<400> SEQUENCE: 123
ccactcgccg cagccatttc cccagcccct gt                               32

<210> SEQ ID NO 124
<211> LENGTH: 32
<212> TYPE: DNA
<213> ORGANISM: Artificial Sequence
<220> FEATURE:
<223> OTHER INFORMATION: Synthetic construct

<400> SEQUENCE: 124
```
ggcaagtggg gaaagggctc cctggtgacc tg                                    32

<210> SEQ ID NO 125
<211> LENGTH: 32
<212> TYPE: DNA
<213> ORGANISM: Artificial Sequence
<220> FEATURE:
<223> OTHER INFORMATION: Synthetic construct

<400> SEQUENCE: 125
ccacttgccg cagccatttc cccagcccct gt                                    32

<210> SEQ ID NO 126
<211> LENGTH: 32
<212> TYPE: DNA
<213> ORGANISM: Artificial Sequence
<220> FEATURE:
<223> OTHER INFORMATION: Synthetic construct

<400> SEQUENCE: 126
ggccggtggg gaaagggctc cctggtgacc tg                                    32

<210> SEQ ID NO 127
<211> LENGTH: 32
<212> TYPE: DNA
<213> ORGANISM: Artificial Sequence
<220> FEATURE:
<223> OTHER INFORMATION: Synthetic construct

<400> SEQUENCE: 127
ccaccggccg cagccatttc cccagcccct gt                                    32

<210> SEQ ID NO 128
<211> LENGTH: 32
<212> TYPE: DNA
<213> ORGANISM: Artificial Sequence
<220> FEATURE:
<223> OTHER INFORMATION: Synthetic construct

<400> SEQUENCE: 128
ggcgactggg gaaagggctc cctggtgacc tg                                    32

<210> SEQ ID NO 129
<211> LENGTH: 32
<212> TYPE: DNA
<213> ORGANISM: Artificial Sequence
<220> FEATURE:
<223> OTHER INFORMATION: Synthetic construct

<400> SEQUENCE: 129
ccagtcgccg cagccatttc cccagcccct gt                                    32

<210> SEQ ID NO 130
<211> LENGTH: 32
<212> TYPE: DNA
<213> ORGANISM: Artificial Sequence
<220> FEATURE:
<223> OTHER INFORMATION: Synthetic construct

<400> SEQUENCE: 130
ggcaagtacg gaaagggctc cctggtgacc tg                                    32

<210> SEQ ID NO 131
<211> LENGTH: 32
<212> TYPE: DNA

-continued

```
<213> ORGANISM: Artificial Sequence
<220> FEATURE:
<223> OTHER INFORMATION: Synthetic construct

<400> SEQUENCE: 131
gtacttgccg cagccatttc cccagcccct gt                                    32

<210> SEQ ID NO 132
<211> LENGTH: 32
<212> TYPE: DNA
<213> ORGANISM: Artificial Sequence
<220> FEATURE:
<223> OTHER INFORMATION: Synthetic construct

<400> SEQUENCE: 132
ctgttattcg gaaagggagg catcgtgact tg                                    32

<210> SEQ ID NO 133
<211> LENGTH: 32
<212> TYPE: DNA
<213> ORGANISM: Artificial Sequence
<220> FEATURE:
<223> OTHER INFORMATION: Synthetic construct

<400> SEQUENCE: 133
gaataacagg catccattgc cccagcctct gt                                    32

<210> SEQ ID NO 134
<211> LENGTH: 32
<212> TYPE: DNA
<213> ORGANISM: Artificial Sequence
<220> FEATURE:
<223> OTHER INFORMATION: Synthetic construct

<400> SEQUENCE: 134
ttcttattcg gaaagggagg catcgtgact tg                                    32

<210> SEQ ID NO 135
<211> LENGTH: 32
<212> TYPE: DNA
<213> ORGANISM: Artificial Sequence
<220> FEATURE:
<223> OTHER INFORMATION: Synthetic construct

<400> SEQUENCE: 135
gaataagaag catccattgc cccagcctct gt                                    32

<210> SEQ ID NO 136
<211> LENGTH: 32
<212> TYPE: DNA
<213> ORGANISM: Artificial Sequence
<220> FEATURE:
<223> OTHER INFORMATION: Synthetic construct

<400> SEQUENCE: 136
tggttattcg gaaagggagg catcgtgact tg                                    32

<210> SEQ ID NO 137
<211> LENGTH: 32
<212> TYPE: DNA
<213> ORGANISM: Artificial Sequence
<220> FEATURE:
<223> OTHER INFORMATION: Synthetic construct

<400> SEQUENCE: 137
gaataaccag catccattgc cccagcctct gt                                    32
```

-continued

```
<210> SEQ ID NO 138
<211> LENGTH: 32
<212> TYPE: DNA
<213> ORGANISM: Artificial Sequence
<220> FEATURE:
<223> OTHER INFORMATION: Synthetic construct

<400> SEQUENCE: 138
tacttattcg gaaagggagg catcgtgact tg                          32

<210> SEQ ID NO 139
<211> LENGTH: 32
<212> TYPE: DNA
<213> ORGANISM: Artificial Sequence
<220> FEATURE:
<223> OTHER INFORMATION: Synthetic construct

<400> SEQUENCE: 139
gaataagtag catccattgc cccagcctct gt                          32

<210> SEQ ID NO 140
<211> LENGTH: 32
<212> TYPE: DNA
<213> ORGANISM: Artificial Sequence
<220> FEATURE:
<223> OTHER INFORMATION: Synthetic construct

<400> SEQUENCE: 140
atcttattcg gaaagggagg catcgtgact tg                          32

<210> SEQ ID NO 141
<211> LENGTH: 32
<212> TYPE: DNA
<213> ORGANISM: Artificial Sequence
<220> FEATURE:
<223> OTHER INFORMATION: Synthetic construct

<400> SEQUENCE: 141
gaataagatg catccattgc cccagcctct gt                          32

<210> SEQ ID NO 142
<211> LENGTH: 32
<212> TYPE: DNA
<213> ORGANISM: Artificial Sequence
<220> FEATURE:
<223> OTHER INFORMATION: Synthetic construct

<400> SEQUENCE: 142
ggtgagttcg gaaagggagg catcgtgact tg                          32

<210> SEQ ID NO 143
<211> LENGTH: 32
<212> TYPE: DNA
<213> ORGANISM: Artificial Sequence
<220> FEATURE:
<223> OTHER INFORMATION: Synthetic construct

<400> SEQUENCE: 143
gaactcaccg catccattgc cccagcctct gt                          32

<210> SEQ ID NO 144
<211> LENGTH: 32
<212> TYPE: DNA
<213> ORGANISM: Artificial Sequence
<220> FEATURE:
```

-continued

<223> OTHER INFORMATION: Synthetic construct

<400> SEQUENCE: 144
ggtaagttcg gaaagggagg catcgtgact tg                                    32

<210> SEQ ID NO 145
<211> LENGTH: 32
<212> TYPE: DNA
<213> ORGANISM: Artificial Sequence
<220> FEATURE:
<223> OTHER INFORMATION: Synthetic construct

<400> SEQUENCE: 145
gaacttaccg catccattgc cccagcctct gt                                    32

<210> SEQ ID NO 146
<211> LENGTH: 32
<212> TYPE: DNA
<213> ORGANISM: Artificial Sequence
<220> FEATURE:
<223> OTHER INFORMATION: Synthetic construct

<400> SEQUENCE: 146
ggtcggttcg gaaagggagg catcgtgact tg                                    32

<210> SEQ ID NO 147
<211> LENGTH: 32
<212> TYPE: DNA
<213> ORGANISM: Artificial Sequence
<220> FEATURE:
<223> OTHER INFORMATION: Synthetic construct

<400> SEQUENCE: 147
gaaccgaccg catccattgc cccagcctct gt                                    32

<210> SEQ ID NO 148
<211> LENGTH: 32
<212> TYPE: DNA
<213> ORGANISM: Artificial Sequence
<220> FEATURE:
<223> OTHER INFORMATION: Synthetic construct

<400> SEQUENCE: 148
ggtgacttcg gaaagggagg catcgtgact tg                                    32

<210> SEQ ID NO 149
<211> LENGTH: 32
<212> TYPE: DNA
<213> ORGANISM: Artificial Sequence
<220> FEATURE:
<223> OTHER INFORMATION: Synthetic construct

<400> SEQUENCE: 149
gaagtcaccg catccattgc cccagcctct gt                                    32

<210> SEQ ID NO 150
<211> LENGTH: 32
<212> TYPE: DNA
<213> ORGANISM: Artificial Sequence
<220> FEATURE:
<223> OTHER INFORMATION: Synthetic construct

<400> SEQUENCE: 150
ggtaccttcg gaaagggagg catcgtgact tg                                    32

-continued

```
<210> SEQ ID NO 151
<211> LENGTH: 32
<212> TYPE: DNA
<213> ORGANISM: Artificial Sequence
<220> FEATURE:
<223> OTHER INFORMATION: Synthetic construct

<400> SEQUENCE: 151
gaaggtaccg catccattgc cccagcctct gt                                      32

<210> SEQ ID NO 152
<211> LENGTH: 32
<212> TYPE: DNA
<213> ORGANISM: Artificial Sequence
<220> FEATURE:
<223> OTHER INFORMATION: Synthetic construct

<400> SEQUENCE: 152
ggtttatggg gaaagggagg catcgtgact tg                                      32

<210> SEQ ID NO 153
<211> LENGTH: 32
<212> TYPE: DNA
<213> ORGANISM: Artificial Sequence
<220> FEATURE:
<223> OTHER INFORMATION: Synthetic construct

<400> SEQUENCE: 153
ccataaaccg catccattgc cccagcctct gt                                      32

<210> SEQ ID NO 154
<211> LENGTH: 32
<212> TYPE: DNA
<213> ORGANISM: Artificial Sequence
<220> FEATURE:
<223> OTHER INFORMATION: Synthetic construct

<400> SEQUENCE: 154
ggtttacacg gaaagggagg catcgtgact tg                                      32

<210> SEQ ID NO 155
<211> LENGTH: 32
<212> TYPE: DNA
<213> ORGANISM: Artificial Sequence
<220> FEATURE:
<223> OTHER INFORMATION: Synthetic construct

<400> SEQUENCE: 155
gtgtaaaccg catccattgc cccagcctct gt                                      32

<210> SEQ ID NO 156
<211> LENGTH: 32
<212> TYPE: DNA
<213> ORGANISM: Artificial Sequence
<220> FEATURE:
<223> OTHER INFORMATION: Synthetic construct

<400> SEQUENCE: 156
ggtttatacg gaaagggagg catcgtgact tg                                      32

<210> SEQ ID NO 157
<211> LENGTH: 32
<212> TYPE: DNA
<213> ORGANISM: Artificial Sequence
<220> FEATURE:
<223> OTHER INFORMATION: Synthetic construct
```

-continued

<400> SEQUENCE: 157
gtataaaccg catccattgc cccagcctct gt                                    32

<210> SEQ ID NO 158
<211> LENGTH: 32
<212> TYPE: DNA
<213> ORGANISM: Artificial Sequence
<220> FEATURE:
<223> OTHER INFORMATION: Synthetic construct

<400> SEQUENCE: 158
ggtttacccg gaaagggagg catcgtgact tg                                    32

<210> SEQ ID NO 159
<211> LENGTH: 32
<212> TYPE: DNA
<213> ORGANISM: Artificial Sequence
<220> FEATURE:
<223> OTHER INFORMATION: Synthetic construct

<400> SEQUENCE: 159
gggtaaaccg catccattgc cccagcctct gt                                    32

<210> SEQ ID NO 160
<211> LENGTH: 32
<212> TYPE: DNA
<213> ORGANISM: Artificial Sequence
<220> FEATURE:
<223> OTHER INFORMATION: Synthetic construct

<400> SEQUENCE: 160
ggtttagccg gaaagggagg catcgtgact tg                                    32

<210> SEQ ID NO 161
<211> LENGTH: 32
<212> TYPE: DNA
<213> ORGANISM: Artificial Sequence
<220> FEATURE:
<223> OTHER INFORMATION: Synthetic construct

<400> SEQUENCE: 161
ggctaaaccg catccattgc cccagcctct gt                                    32

<210> SEQ ID NO 162
<211> LENGTH: 32
<212> TYPE: DNA
<213> ORGANISM: Artificial Sequence
<220> FEATURE:
<223> OTHER INFORMATION: Synthetic construct

<400> SEQUENCE: 162
ctggagttcg gaaagggagg catcgtgact tg                                    32

<210> SEQ ID NO 163
<211> LENGTH: 32
<212> TYPE: DNA
<213> ORGANISM: Artificial Sequence
<220> FEATURE:
<223> OTHER INFORMATION: Synthetic construct

<400> SEQUENCE: 163
gaactccagg catccattgc cccagcctct gt                                    32

<210> SEQ ID NO 164
<211> LENGTH: 32

```
<212> TYPE: DNA
<213> ORGANISM: Artificial Sequence
<220> FEATURE:
<223> OTHER INFORMATION: Synthetic construct

<400> SEQUENCE: 164
ctgaagttcg gaaagggagg catcgtgact tg                                      32

<210> SEQ ID NO 165
<211> LENGTH: 32
<212> TYPE: DNA
<213> ORGANISM: Artificial sequence
<220> FEATURE:
<223> OTHER INFORMATION: Synthetic construct

<400> SEQUENCE: 165
gaacttcagg catccattgc cccagcctct gt                                      32

<210> SEQ ID NO 166
<211> LENGTH: 32
<212> TYPE: DNA
<213> ORGANISM: Artificial Sequence
<220> FEATURE:
<223> OTHER INFORMATION: Synthetic construct

<400> SEQUENCE: 166
ttcgagttcg gaaagggagg catcgtgact tg                                      32

<210> SEQ ID NO 167
<211> LENGTH: 32
<212> TYPE: DNA
<213> ORGANISM: Artificial Sequence
<220> FEATURE:
<223> OTHER INFORMATION: Synthetic construct

<400> SEQUENCE: 167
gaactcgaag catccattgc cccagcctct gt                                      32

<210> SEQ ID NO 168
<211> LENGTH: 32
<212> TYPE: DNA
<213> ORGANISM: Artificial Sequence
<220> FEATURE:
<223> OTHER INFORMATION: Synthetic construct

<400> SEQUENCE: 168
ttcaagttcg gaaagggagg catcgtgact tg                                      32

<210> SEQ ID NO 169
<211> LENGTH: 32
<212> TYPE: DNA
<213> ORGANISM: Artificial sequence
<220> FEATURE:
<223> OTHER INFORMATION: Synthetic construct

<400> SEQUENCE: 169
gaacttgaag catccattgc cccagcctct gt                                      32

<210> SEQ ID NO 170
<211> LENGTH: 32
<212> TYPE: DNA
<213> ORGANISM: Artificial Sequence
<220> FEATURE:
<223> OTHER INFORMATION: Synthetic construct

<400> SEQUENCE: 170
```

-continued

```
ttccggttcg gaaagggagg catcgtgact tg                               32

<210> SEQ ID NO 171
<211> LENGTH: 32
<212> TYPE: DNA
<213> ORGANISM: Artificial Sequence
<220> FEATURE:
<223> OTHER INFORMATION: Synthetic construct

<400> SEQUENCE: 171
gaaccggaag catccattgc cccagcctct gt                               32

<210> SEQ ID NO 172
<211> LENGTH: 32
<212> TYPE: DNA
<213> ORGANISM: Artificial Sequence
<220> FEATURE:
<223> OTHER INFORMATION: Synthetic construct

<400> SEQUENCE: 172
ttcttatggg gaaagggagg catcgtgact tg                               32

<210> SEQ ID NO 173
<211> LENGTH: 32
<212> TYPE: DNA
<213> ORGANISM: Artificial Sequence
<220> FEATURE:
<223> OTHER INFORMATION: Synthetic construct

<400> SEQUENCE: 173
ccataagaag catccattgc cccagcctct gt                               32

<210> SEQ ID NO 174
<211> LENGTH: 32
<212> TYPE: DNA
<213> ORGANISM: Artificial Sequence
<220> FEATURE:
<223> OTHER INFORMATION: Synthetic construct

<400> SEQUENCE: 174
ctgttatggg gaaagggagg catcgtgact tg                               32

<210> SEQ ID NO 175
<211> LENGTH: 32
<212> TYPE: DNA
<213> ORGANISM: Artificial Sequence
<220> FEATURE:
<223> OTHER INFORMATION: Synthetic construct

<400> SEQUENCE: 175
ccataacagg catccattgc cccagcctct gt                               32

<210> SEQ ID NO 176
<211> LENGTH: 32
<212> TYPE: DNA
<213> ORGANISM: Artificial Sequence
<220> FEATURE:
<223> OTHER INFORMATION: Synthetic construct

<400> SEQUENCE: 176
ttcttacacg gaaagggagg catcgtgact tg                               32

<210> SEQ ID NO 177
<211> LENGTH: 32
<212> TYPE: DNA
<213> ORGANISM: Artificial Sequence
```

-continued

```
<220> FEATURE:
<223> OTHER INFORMATION: Synthetic construct

<400> SEQUENCE: 177
gtgtaagaag catccattgc cccagcctct gt                                        32

<210> SEQ ID NO 178
<211> LENGTH: 32
<212> TYPE: DNA
<213> ORGANISM: Artificial Sequence
<220> FEATURE:
<223> OTHER INFORMATION: Synthetic construct

<400> SEQUENCE: 178
tacttatggg gaaagggagg catcgtgact tg                                        32

<210> SEQ ID NO 179
<211> LENGTH: 32
<212> TYPE: DNA
<213> ORGANISM: Artificial Sequence
<220> FEATURE:
<223> OTHER INFORMATION: Synthetic construct

<400> SEQUENCE: 179
ccataagtag catccattgc cccagcctct gt                                        32

<210> SEQ ID NO 180
<211> LENGTH: 32
<212> TYPE: DNA
<213> ORGANISM: Artificial Sequence
<220> FEATURE:
<223> OTHER INFORMATION: Synthetic construct

<400> SEQUENCE: 180
tggttatacg gaaagggagg catcgtgact tg                                        32

<210> SEQ ID NO 181
<211> LENGTH: 32
<212> TYPE: DNA
<213> ORGANISM: Artificial Sequence
<220> FEATURE:
<223> OTHER INFORMATION: Synthetic construct

<400> SEQUENCE: 181
gtataaccag catccattgc cccagcctct gt                                        32

<210> SEQ ID NO 182
<211> LENGTH: 32
<212> TYPE: DNA
<213> ORGANISM: Artificial Sequence
<220> FEATURE:
<223> OTHER INFORMATION: Synthetic construct

<400> SEQUENCE: 182
ggtgagtggg gaaagggagg catcgtgact tg                                        32

<210> SEQ ID NO 183
<211> LENGTH: 32
<212> TYPE: DNA
<213> ORGANISM: Artificial Sequence
<220> FEATURE:
<223> OTHER INFORMATION: Synthetic construct

<400> SEQUENCE: 183
ccactcaccg catccattgc cccagcctct gt                                        32
```

```
<210> SEQ ID NO 184
<211> LENGTH: 32
<212> TYPE: DNA
<213> ORGANISM: Artificial Sequence
<220> FEATURE:
<223> OTHER INFORMATION: Synthetic construct

<400> SEQUENCE: 184
ggtaagtggg gaaagggagg catcgtgact tg                               32

<210> SEQ ID NO 185
<211> LENGTH: 32
<212> TYPE: DNA
<213> ORGANISM: Artificial Sequence
<220> FEATURE:
<223> OTHER INFORMATION: Synthetic construct

<400> SEQUENCE: 185
ccacttaccg catccattgc cccagcctct gt                               32

<210> SEQ ID NO 186
<211> LENGTH: 32
<212> TYPE: DNA
<213> ORGANISM: Artificial Sequence
<220> FEATURE:
<223> OTHER INFORMATION: Synthetic construct

<400> SEQUENCE: 186
ggtcggtggg gaaagggagg catcgtgact tg                               32

<210> SEQ ID NO 187
<211> LENGTH: 32
<212> TYPE: DNA
<213> ORGANISM: Artificial Sequence
<220> FEATURE:
<223> OTHER INFORMATION: Synthetic construct

<400> SEQUENCE: 187
ccaccgaccg catccattgc cccagcctct gt                               32

<210> SEQ ID NO 188
<211> LENGTH: 32
<212> TYPE: DNA
<213> ORGANISM: Artificial Sequence
<220> FEATURE:
<223> OTHER INFORMATION: Synthetic construct

<400> SEQUENCE: 188
ggtgactggg gaaagggagg catcgtgact tg                               32

<210> SEQ ID NO 189
<211> LENGTH: 32
<212> TYPE: DNA
<213> ORGANISM: Artificial Sequence
<220> FEATURE:
<223> OTHER INFORMATION: Synthetic construct

<400> SEQUENCE: 189
ccagtcaccg catccattgc cccagcctct gt                               32

<210> SEQ ID NO 190
<211> LENGTH: 32
<212> TYPE: DNA
<213> ORGANISM: Artificial Sequence
<220> FEATURE:
<223> OTHER INFORMATION: Synthetic construct
```

-continued

<400> SEQUENCE: 190
ggtaagtacg gaaagggagg catcgtgact tg                                        32

<210> SEQ ID NO 191
<211> LENGTH: 32
<212> TYPE: DNA
<213> ORGANISM: Artificial Sequence
<220> FEATURE:
<223> OTHER INFORMATION: Synthetic construct

<400> SEQUENCE: 191
gtacttaccg catccattgc cccagcctct gt                                        32

<210> SEQ ID NO 192
<211> LENGTH: 12
<212> TYPE: PRT
<213> ORGANISM: Artificial Sequence
<220> FEATURE:
<223> OTHER INFORMATION: Synthetic construct

<400> SEQUENCE: 192

Asp Arg Gly Trp Gly Asn Gly Cys Gly Leu Phe Gly
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Synthetic construct

<400> SEQUENCE: 193

Asn Arg Gly Trp Gly Thr Gly Cys Phe Glu Trp Gly
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Synthetic construct

<400> SEQUENCE: 194

Asn Arg Gly Trp Gly Thr Gly Cys Phe Lys Trp Gly
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Synthetic construct

<400> SEQUENCE: 195

Asn Arg Gly Trp Gly Thr Gly Cys Leu Glu Trp Gly
1               5                   10

<210> SEQ ID NO 196
<211> LENGTH: 115
<212> TYPE: PRT
<213> ORGANISM: Artificial Sequence
<220> FEATURE:
<223> OTHER INFORMATION: Synthetic construct

<400> SEQUENCE: 196

-continued

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Tyr Tyr Ala Met Asp Tyr Trp Gly Gln Gly Thr Ser Val Thr
            100                 105                 110

Val Ser Ser
        115
```

```
<210> SEQ ID NO 197
<211> LENGTH: 118
<212> TYPE: PRT
<213> ORGANISM: Artificial Sequence
<220> FEATURE:
<223> OTHER INFORMATION: Synthetic construct

<400> SEQUENCE: 197
```

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Val Tyr
            20                  25                  30

Ser Met His Trp Val Lys Gln Ala Pro Gly Lys Gly Leu Lys Trp Met
        35                  40                  45

Gly Trp Ile Asn Pro Glu Thr Gly Glu Pro Thr Tyr Ala Asp Asp Phe
    50                  55                  60

Lys Gly Arg Phe Ala Phe Ser Leu Glu Ile Ser Ala Ser Thr Ala Ser
65                  70                  75                  80

Leu Gln Ile Asn Asn Leu Lys Asn Glu Asp Thr Ala Thr Tyr Phe Cys
                85                  90                  95

Ala Arg Gly Gly Asp Asn Tyr Ala Val Asp Tyr Trp Gly Gln Gly Thr
            100                 105                 110

Ser Val Thr Val Ser Ser
        115
```

```
<210> SEQ ID NO 198
<211> LENGTH: 118
<212> TYPE: PRT
<213> ORGANISM: Artificial Sequence
<220> FEATURE:
<223> OTHER INFORMATION: Synthetic construct

<400> SEQUENCE: 198
```

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Asp Pro Ser Tyr Ala Asp Asp Phe
    50                  55                  60
```

-continued

```
Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Pro Thr Tyr Phe Cys
                85                  90                  95

Ala Arg Gly Gly Asn Asp Tyr Ser Met Asp Tyr Trp Gly Gln Gly Thr
            100                 105                 110

Ser Val Thr Val Ser Ser
        115

<210> SEQ ID NO 199
<211> LENGTH: 118
<212> TYPE: PRT
<213> ORGANISM: Artificial Sequence
<220> FEATURE:
<223> OTHER INFORMATION: Synthetic construct

<400> SEQUENCE: 199

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
        35                  40                  45

Gly Trp Ile Asn Pro Glu Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Gly Asp Ser Tyr Ser Met Asp Tyr Trp Gly Gln Gly Thr
            100                 105                 110

Ser Val Thr Val Ser Ser
        115

<210> SEQ ID NO 200
<211> LENGTH: 118
<212> TYPE: PRT
<213> ORGANISM: Artificial Sequence
<220> FEATURE:
<223> OTHER INFORMATION: Synthetic construct

<400> SEQUENCE: 200

Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Val Phe Thr Asp Tyr
                20                  25                  30

Ser Met His Trp Val Arg Gln Ser Pro Gly Lys Gly Leu Lys Trp Met
        35                  40                  45

Gly Trp Ile Asn Pro Glu Thr Gly Glu Pro Thr His Ala Asp Asp Phe
        50                  55                  60

Lys Gly Arg Phe Asp Phe Ser Leu Glu Thr Ser Ala Arg Thr Ala Tyr
65                  70                  75                  80

Leu Gln Ile Ser Asn Leu Glu Asn Glu Asp Thr Ala Thr Tyr Leu Cys
                85                  90                  95

Ala Arg Gly Gly Asp Asp Tyr Gly Met Asp Tyr Trp Gly Gln Gly Thr
            100                 105                 110

Ser Val Thr Val Ser Ser
```

115

<210> SEQ ID NO 201
<211> LENGTH: 108
<212> TYPE: PRT
<213> ORGANISM: Artificial Sequence
<220> FEATURE:
<223> OTHER INFORMATION: Synthetic construct

<400> SEQUENCE: 201

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Trp Thr Phe Gly Gly Gly Thr Lys Leu Glu Ile Lys
            100                 105

<210> SEQ ID NO 202
<211> LENGTH: 107
<212> TYPE: PRT
<213> ORGANISM: Artificial Sequence
<220> FEATURE:
<223> OTHER INFORMATION: Synthetic construct

<400> SEQUENCE: 202

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Gln Gln
65                  70                  75                  80

Glu Asp Ile Ala Ala Tyr Phe Cys Gln Gln Gly Asn Thr Leu Pro Leu
                85                  90                  95

Thr Phe Gly Ala Gly Thr Lys Leu Glu Leu Lys
            100                 105

<210> SEQ ID NO 203
<211> LENGTH: 107
<212> TYPE: PRT
<213> ORGANISM: Artificial Sequence
<220> FEATURE:
<223> OTHER INFORMATION: Synthetic construct

<400> SEQUENCE: 203

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

-continued

```
Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Pro Asp Tyr Ser Leu Thr Ile Ser Asn Leu Glu Gln
65                  70                  75                  80

Glu Asp Val Ala Thr Tyr Phe Cys Gln Gln Gly Asn Thr Leu Pro Pro
                85                  90                  95

Thr Phe Asp Gly Gly Thr Arg Leu Glu Ile Lys
            100                 105
```

```
<210> SEQ ID NO 204
<211> LENGTH: 107
<212> TYPE: PRT
<213> ORGANISM: Artificial Sequence
<220> FEATURE:
<223> OTHER INFORMATION: Synthetic construct

<400> SEQUENCE: 204

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser His Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Val Thr Lys Leu Glu Ile Lys
            100                 105
```

```
<210> SEQ ID NO 205
<211> LENGTH: 107
<212> TYPE: PRT
<213> ORGANISM: Artificial Sequence
<220> FEATURE:
<223> OTHER INFORMATION: Synthetic construct

<400> SEQUENCE: 205

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105
```

```
<210> SEQ ID NO 206
<211> LENGTH: 113
<212> TYPE: PRT
<213> ORGANISM: Artificial Sequence
<220> FEATURE:
<223> OTHER INFORMATION: Synthetic construct

<400> SEQUENCE: 206

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Tyr Phe Asp Tyr Trp Gly Gln Gly Thr Thr Leu Thr Val Ser
            100                 105                 110

Ser

<210> SEQ ID NO 207
<211> LENGTH: 115
<212> TYPE: PRT
<213> ORGANISM: Artificial Sequence
<220> FEATURE:
<223> OTHER INFORMATION: Synthetic construct

<400> SEQUENCE: 207

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Tyr Tyr Ala Met Asp Tyr Trp Gly Gln Gly Thr Ser Val Thr
            100                 105                 110

Val Ser Ser
        115

<210> SEQ ID NO 208
<211> LENGTH: 121
<212> TYPE: PRT
<213> ORGANISM: Artificial Sequence
<220> FEATURE:
<223> OTHER INFORMATION: Synthetic construct

<400> SEQUENCE: 208

Glu Val Gln Leu Gln Gln Ser Gly Pro Glu Leu Val Lys Pro Gly Ala
1               5                   10                  15
```

```
Ser Val Lys Ile Ser Cys Lys Thr Ser Gly Tyr Thr Phe Thr Glu Phe
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Met Phe
    50                  55                  60

Lys Gly Lys Ala Thr Leu Thr Val Asp Asn Ser Ser Thr Ala Tyr
65                  70                  75                  80

Met Glu Val Arg Ser Leu Thr Ser Asp Asp Ser Ala Val Tyr Tyr Cys
                85                  90                  95

Ala Arg Ile Thr Val Val Ala Glu Asp Ser Tyr Phe Asp Tyr Trp Gly
            100                 105                 110

Gln Gly Thr Thr Leu Thr Val Ser Ser
        115                 120
```

```
<210> SEQ ID NO 209
<211> LENGTH: 118
<212> TYPE: PRT
<213> ORGANISM: Artificial Sequence
<220> FEATURE:
<223> OTHER INFORMATION: Synthetic construct

<400> SEQUENCE: 209
```

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Pro Phe Thr Glu Tyr
            20                  25                  30

Thr Met His Trp Val Lys Gln Ser Leu Gly Lys Ser Leu Glu Tyr Ile
        35                  40                  45

Gly Gly Ile Asn Pro Asn Asn Gly Gly Ser Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Ile Tyr Gly Gly His Met Asp Tyr Trp Gly Gln Gly Thr
            100                 105                 110

Ser Val Thr Val Ser Ser
        115
```

```
<210> SEQ ID NO 210
<211> LENGTH: 117
<212> TYPE: PRT
<213> ORGANISM: Artificial Sequence
<220> FEATURE:
<223> OTHER INFORMATION: Synthetic construct

<400> SEQUENCE: 210
```

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Pro Leu Thr Val Asp Lys Ser Ser Ser Thr Ala Tyr
65                  70                  75                  80
```

-continued

```
Met Glu Leu Arg Ser Leu Thr Ser Asp Asp Ser Ala Val Tyr Phe Cys
                85                  90                  95

Ala Arg His Tyr Arg Tyr Tyr Leu Asp Tyr Trp Gly Gln Gly Thr Thr
            100                 105                 110

Leu Thr Val Ser Ser
        115

<210> SEQ ID NO 211
<211> LENGTH: 119
<212> TYPE: PRT
<213> ORGANISM: Artificial Sequence
<220> FEATURE:
<223> OTHER INFORMATION: Synthetic construct

<400> SEQUENCE: 211

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Ala Trp Ile
        35                  40                  45

Gly Gly Ile Asp Pro Asn Ser Gly Gly Thr Asn Tyr Ser Pro Asn Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Ser Ser Glu Asp Ser Ala Val Tyr Phe Cys
                85                  90                  95

Ala Arg Ile Tyr His Tyr Asp Gly Tyr Phe Asp Val Trp Gly Ala Gly
            100                 105                 110

Thr Ala Val Thr Val Ser Ser
        115

<210> SEQ ID NO 212
<211> LENGTH: 117
<212> TYPE: PRT
<213> ORGANISM: Artificial Sequence
<220> FEATURE:
<223> OTHER INFORMATION: Synthetic construct

<400> SEQUENCE: 212

Glu Val Gln Leu Gln Gln Ser Gly Pro Glu Leu Val Lys Pro Gly Ala
1               5                   10                  15

Ser Val Lys Leu Ser Cys Lys Thr Ser Glu Asn Thr Phe Thr Glu Tyr
            20                  25                  30

Thr Met His Trp Val Lys Gln Ser His Gly Lys Ser Leu Glu Trp Ile
        35                  40                  45

Gly Gly Ile Asp Pro Asn Asn Gly Gly Thr Asn Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Gly Arg Arg Asp Tyr Tyr Ala Leu Asp Tyr Trp Gly Gln Gly Thr Ser
            100                 105                 110

Val Thr Val Ala Ser
        115
```

-continued

```
<210> SEQ ID NO 213
<211> LENGTH: 107
<212> TYPE: PRT
<213> ORGANISM: Artificial Sequence
<220> FEATURE:
<223> OTHER INFORMATION: Synthetic construct

<400> SEQUENCE: 213

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Trp
                85                  90                  95

Thr Phe Gly Gly Gly Thr Lys Leu Glu Ile Lys
            100                 105

<210> SEQ ID NO 214
<211> LENGTH: 107
<212> TYPE: PRT
<213> ORGANISM: Artificial Sequence
<220> FEATURE:
<223> OTHER INFORMATION: Synthetic construct

<400> SEQUENCE: 214

Asp Ile Lys Met Thr Gln Ser Pro Ser Ser Met Tyr Ala Phe Leu Gly
1               5                   10                  15

Glu Arg Val Thr Ile Thr Cys Lys Ala Ser Gln Asp Ile Asn Ser His
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Val Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 215
<211> LENGTH: 107
<212> TYPE: PRT
<213> ORGANISM: Artificial Sequence
<220> FEATURE:
<223> OTHER INFORMATION: Synthetic construct

<400> SEQUENCE: 215

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
                20                  25                  30

Leu Gly Trp Phe Gln Gln Lys Pro Gly Lys Ser Pro Lys Thr Leu Ile
            35                  40                  45
```

-continued

```
Tyr Arg Ala Asn Arg Leu Val Asp Gly Val Pro Ser Arg Phe Ser Gly
    50                  55                  60

Ser Gly Ser Gly Gln Asp Tyr Ser Leu Ile Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 216
<211> LENGTH: 107
<212> TYPE: PRT
<213> ORGANISM: Artificial Sequence
<220> FEATURE:
<223> OTHER INFORMATION: Synthetic construct

<400> SEQUENCE: 216

Asp Ile Lys Met Thr Gln Ser Pro Ser Ser Met Tyr Ala Ser Leu Gly
1                   5                   10                  15

Glu Arg Val Thr Ile Thr Cys Lys Ala Ser Gln Asp Ile Asn Ser Tyr
                20                  25                  30

Leu Thr Trp Phe Gln Gln Lys Pro Gly Lys Ser Pro Lys Thr Leu Ile
            35                  40                  45

Tyr Arg Ala Asn Arg Leu Ile Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 217
<211> LENGTH: 107
<212> TYPE: PRT
<213> ORGANISM: Artificial Sequence
<220> FEATURE:
<223> OTHER INFORMATION: Synthetic construct

<400> SEQUENCE: 217

Asp Ile Val Met Thr Gln Ser His Lys Phe Met Ser Thr Ser Val Gly
1                   5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 218
<211> LENGTH: 107
<212> TYPE: PRT
```

-continued

```
<213> ORGANISM: Artificial Sequence
<220> FEATURE:
<223> OTHER INFORMATION: Synthetic construct

<400> SEQUENCE: 218

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 219
<211> LENGTH: 106
<212> TYPE: PRT
<213> ORGANISM: Artificial Sequence
<220> FEATURE:
<223> OTHER INFORMATION: Synthetic construct

<400> SEQUENCE: 219

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Gly Thr Asp
            20                  25                  30

Val Ala Trp Tyr Gln Gln Lys Pro Gly Gln Ser Pro Lys Val Leu Ile
        35                  40                  45

Phe Trp Ala Ser Ala Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Thr
                85                  90                  95

Phe Gly Gly Gly Thr Lys Leu Glu Ile Lys
            100                 105

<210> SEQ ID NO 220
<211> LENGTH: 106
<212> TYPE: PRT
<213> ORGANISM: Artificial Sequence
<220> FEATURE:
<223> OTHER INFORMATION: Synthetic construct

<400> SEQUENCE: 220

Asp Ile Val Met Thr Gln Ser Gln Lys Phe Met Ser Thr Ser Val Gly
1               5                   10                  15

Asp Arg Val Ser Ile Thr Cys Lys Ala Ser Gln His Val Gly Ser Ala
            20                  25                  30

Val Ala Trp Tyr Gln Gln Lys Pro Gly Gln Ser Pro Thr Leu Leu Ile
        35                  40                  45

His Ser Ala Ser Asn Arg Tyr Thr Gly Val Pro Asp Arg Phe Thr Gly
    50                  55                  60
```

-continued

```
Ser Gly Ser Gly Thr Asp Phe Thr Leu Thr Ile Ser Asn Ile Gln Ser
65                  70                  75                  80

Glu Asp Leu Ala Asp Tyr Phe Cys Gln Gln Tyr Asn Ser Tyr Pro Thr
                85                  90                  95

Phe Gly Gly Gly Thr Lys Leu Glu Ile Lys
            100                 105
```